US009587244B2

(12) United States Patent
Li

(10) Patent No.: US 9,587,244 B2
(45) Date of Patent: Mar. 7, 2017

(54) SOYBEAN AGB1 PROMOTER AND ITS USE IN TISSUE-SPECIFIC EXPRESSION OF TRANSGENIC GENES IN PLANTS

(71) Applicant: E. I. DU PONT DE NEMOURS AND COMPANY, Wilmington, DE (US)

(72) Inventor: Zhongsen Li, Hockessin, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/772,729

(22) PCT Filed: Mar. 12, 2014

(86) PCT No.: PCT/US2014/024071

§ 371 (c)(1),
(2) Date: Sep. 3, 2015

(87) PCT Pub. No.: WO2014/150721

PCT Pub. Date: Sep. 25, 2014

(65) Prior Publication Data

US 2016/0017346 A1 Jan. 21, 2016

Related U.S. Application Data

(60) Provisional application No. 61/787,095, filed on Mar. 15, 2013.

(51) Int. Cl.
*C12N 15/82* (2006.01)
*C07K 14/415* (2006.01)

(52) U.S. Cl.
CPC .......... *C12N 15/823* (2013.01); *C07K 14/415* (2013.01)

(58) Field of Classification Search
None
See application file for complete search history.

(56) References Cited

U.S. PATENT DOCUMENTS

2010/0017918 A1 1/2010 Brown et al.

FOREIGN PATENT DOCUMENTS

| | | | |
|---|---|---|---|
| WO | 01/68887 | A2 | 9/2001 |
| WO | 2004/071178 | A2 | 8/2004 |
| WO | 2006/053169 | A2 | 5/2006 |
| WO | 2009/099899 | A2 | 8/2009 |

OTHER PUBLICATIONS

Schmutz et al. Genome sequence of the palaeopolyploid soybean. (2010) Nature; vol. 463; pp. 178-283.*

Tomiko Asakura et al., Global gene expression profiles in developing soybean seeds, Plant Physiology and Biochemistry, 2012, pp. 147-153, vol. 52.

Srinivas Belide et al., Rapid expression and validation of seed-specific constructs in transgenic LEC2 induced somatic embryos of Brassica napus, Plant Cell Tiss Organ Cult, 2013, pp. 543-553, vol. 113.

Zhang-Liang Chen et al., Functional analysis of regulatory elements in a plant embryo-specific gene, Proc. Natl, Acad. Sci, Nov. 1986, pp. 8560-8564, vol. 83.

Meijuan Duan et al., Profiling the expression of genes controlling rice grain quality, Plant Molecular Biology, 2005, pp. 165-178, vol. 59.

NCBI Accession No. AB046874.2, Glycine max mRNA for allergen Gly m Bd 28K, complete cds, Oct. 26, 2012, GI:410067728.

Le Qing Qu et al,, Evaluation of tissue specificity and expression strength of rice seed component gene promoters in transgenic rice, Plant Biotechnology Journal, 2004, pp. 113-125, vol. 2.

Jeremy Schmutz et al., Genome sequence of the palaeoplyploid soybean, Nature, Jan. 14, 2010, pp. 178-183, vol. 463.

A. Wenck et al., Reef-coral proteins as visual, non-destructive reporters for plant transformation, Plant Cell Rep., 2003, pp. 244-251, vol. 22 (XP-002459243).

International Search Report/Written Opinion—PCT/US2014/024071—mailed Jun. 23, 2014.

* cited by examiner

*Primary Examiner* — Cathy Kingdon Worley

(57) ABSTRACT

The invention relates to gene expression regulatory sequences from soybean, specifically to the promoter of a soybean predicted allergen Gly m Bd 28K peptide gene and fragments thereof and their use in promoting the expression of one or more heterologous nucleic acid fragments in a tissue-specific manner in plants. The invention further discloses compositions, polynucleotide constructs, transformed host cells, transgenic plants and seeds containing the recombinant construct with the promoter, and methods for preparing and using the same.

22 Claims, 9 Drawing Sheets

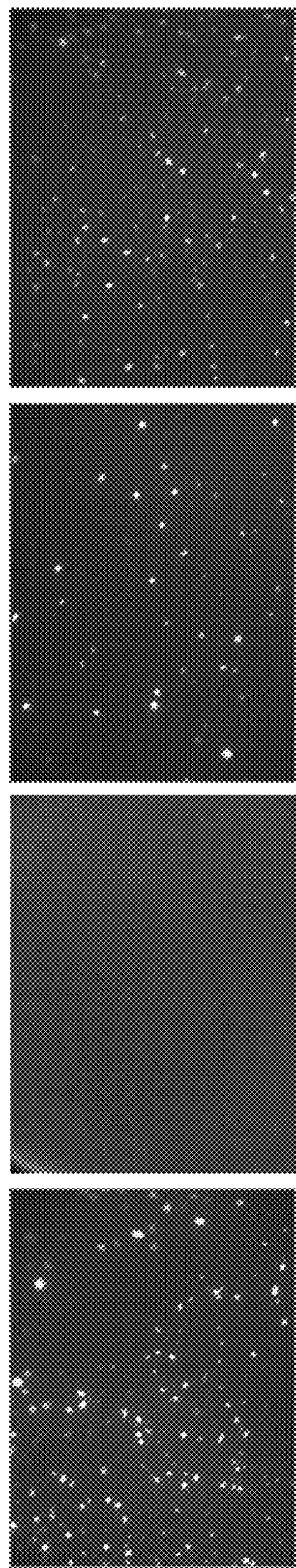
pZSL90
FIG. 6A
QC330-Y
FIG. 6B
QC642
FIG. 6C
QC642-1Y
FIG. 6D
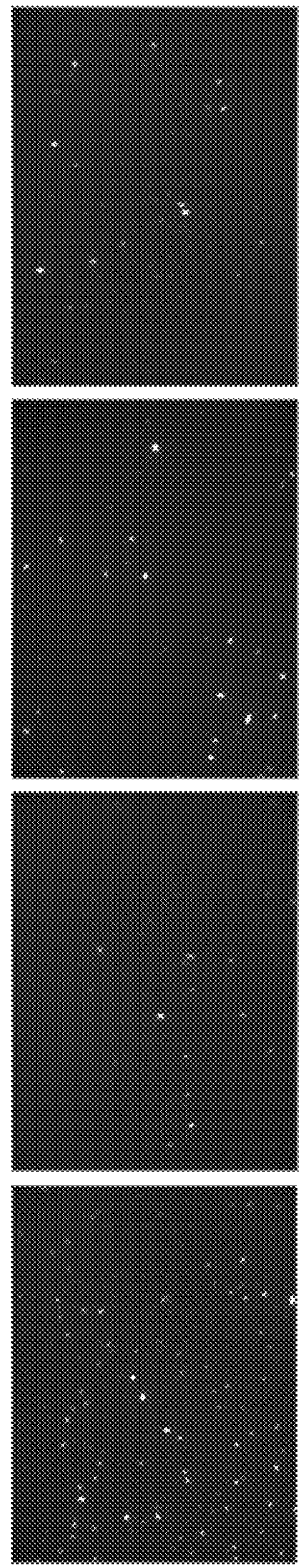
QC642-2Y
FIG. 6E
QC642-3Y
FIG. 6F
QC642-4Y
FIG. 6G
QC642-5Y
FIG. 6H

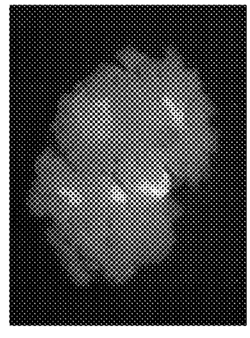
FIG. 7A
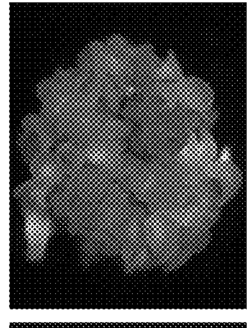
FIG. 7B
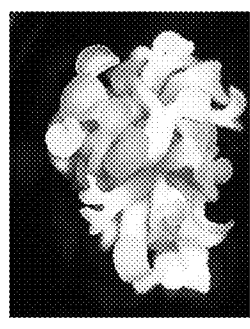
FIG. 7C
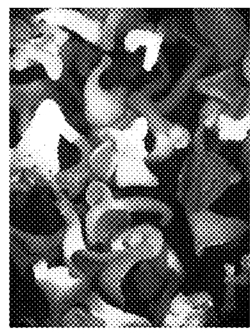
FIG. 7D
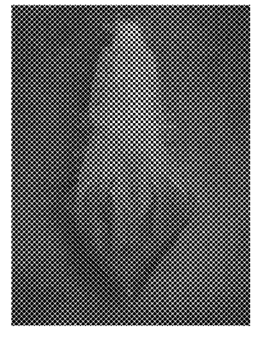
FIG. 7E
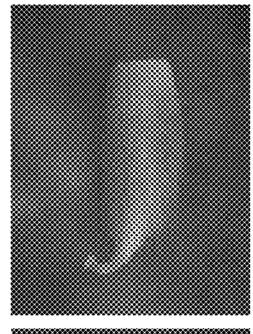
FIG. 7F
FIG. 7G
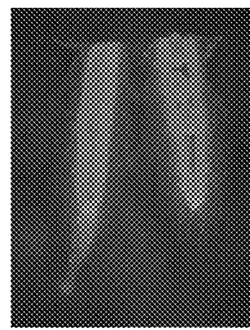
FIG. 7H
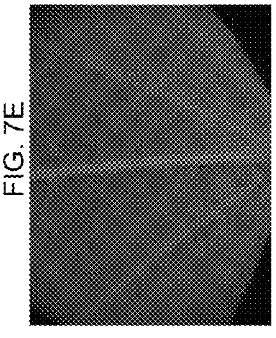
FIG. 7I
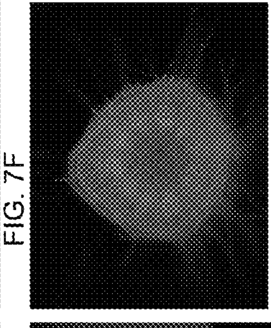
FIG. 7J
FIG. 7K
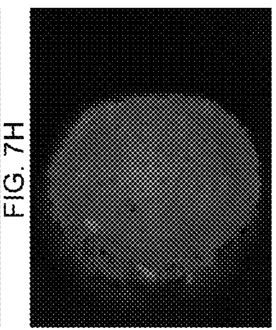
FIG. 7L
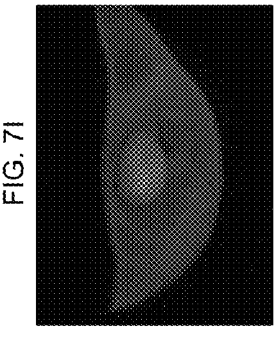
FIG. 7M
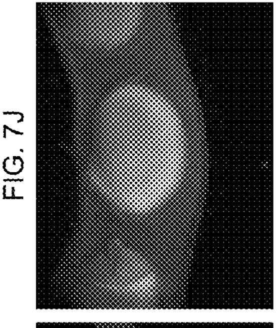
FIG. 7N
FIG. 7O
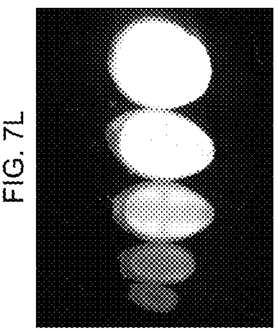
FIG. 7P

FIG. 8

```
                                  1                                                                                                    100
Gm11:11529579-11531009     (1)    TGGGGGTTGCGATTGCTTCGCGTCTTGTTCAACCTTCACACACACAGATTCAAACACGCATCTCTTGCTCTTCACAGAGACACGATCTTCTTTTCTTTTT
           GM-AGB1 PRO     (1)    CCCGGGTTGCGATTGCTTCGCGTCTTGTTCAACCTTCACACACACAGATTCAAACACGCATCTCTTGCTCTTCACAGAGACACGATCTTCTTTTCTTTTT
                                  101                                                                                                  200
Gm11:11529579-11531009   (101)    CGCATAGGCAAAATCTTGGTTGGGATAATCGAATAAATTAAATCAAAATAATATGGATTACATATTTTAATGTTAAAGAATCTGACCGTTTGACGTCTCT
           GM-AGB1 PRO   (101)    CGCATAGGCAAAATCTTGGTTGGGATAATCGAATAAATTAAATCAAAATAATATGGATTACATATTTTAATGTTAAAGAATCTGACCGTTTGACGTCTCT
                                  201                                                                                                  300
Gm11:11529579-11531009   (201)    AATCTGCTATAATTAACTTTCAAAAATTAACTCTGCATAATGTGTAAAAGCCACTCAAAAAACTAAGGTAACAATAAAATGCATATAGGACTAATATACT
           GM-AGB1 PRO   (201)    AATCTGCTATAATTAACTTTCAAAAATTAACTCTGCATAATGTGTAAAAGCCACTCAAAAAACTAAGGTAACAATAAAATGCATATAGGACTAATATACT
                                  301                                                                                                  400
Gm11:11529579-11531009   (301)    AACATTAATTGAAACAATTGATAGTGATTTTTGTCTTTTAAACAAGTGTTTCAGTTTTTCAATCATGTCTTAGGTATGAAGCAGATTATAAATCATATTG
           GM-AGB1 PRO   (301)    AACATTAATTGAAACAATTGATAGTGATTTTTGTCTTTTAAACAAGTGTTTCAGTTTTTCAATCATGTCTTAGGTATGAAGCAGATTATAAATCATATTG
                                  401                                                                                                  500
Gm11:11529579-11531009   (401)    GATAAAAAATATTCAAATTTATTAATTCACGAAGGAGATTTAGTCACAGTTATATGGAACTTTGTTAATTTTGCTCATAATTTTAACATTAAACTTCTTT
           GM-AGB1 PRO   (401)    GATAAAAAATATTCAAATTTATTAATTCACGAAGGAGATTTAGTCACAGTTATATGGAACTTTGTTAATTTTGCTCATAATTTTAACATTAAACTTCTTT
                                  501                                                                                                  600
Gm11:11529579-11531009   (501)    AGAGGGAGGGGGTTAATTAAATGCAAGAGTATCTTTTGTGTTAATTGATTTTACTCTCCAGTATACTTATACTACTATTATATACGATTATGCAATATAA
           GM-AGB1 PRO   (501)    AGAGGGAGGGGGTTAATTAAATGCAAGAGTATCTTTTGTGTTAATTGATTTTACTCTCCAGTATACTTATACTACTATTATATACGATTATGCAATATAA
                                  601                                                                                                  700
Gm11:11529579-11531009   (601)    TTAATTTTTAATTAACAGATAAAAATTCATTTAAGAATTATCAAACATCGTGTAAATAGTTTTTCTTTTTCGCAAGTATACTTTATAGGAAGTAACTCTA
           GM-AGB1 PRO   (601)    TTAATTTTTAATTAACAGATAAAAATTCATTTAAGAATTATCAAACATCGTGTAAATAGTTTTTCTTTTTCGCAAGTATACTTTATAGGAAGTAACTCTA
                                  701                                                                                                  800
Gm11:11529579-11531009   (701)    TTTTTCTTAAAATAACATAAAAAGAAAAGAAACTCATTTTATAAGATAATAAGATGCTAAATGTGAGTAGCTTTAGACATCCACGAAATTTGAACCTTGA
           GM-AGB1 PRO   (701)    TTTTTCTTAAAATAACATAAAAAGAAAAGAAACTCATTTTATAAGATAATAAGATGCTAAATGTGAGTAGCTTTAGACATCCACGAAATTTGAACCTTGA
                                  801                                                                                                  900
Gm11:11529579-11531009   (801)    TTCTCTATTTCACAGTAAATTAGTCTATTAAATTCAACACTATTAATATGTGAGAGGATTTAAATCTTTCTCTATTTTATTTTCATTTTTTAAATGGAAT
           GM-AGB1 PRO   (801)    TTCTCTATTTCACAGTAAATTAGTCTATTAAATTCAACACTATTAATATGTGAGAGGATTTAAATCTTTCTCTATTTTATTTTCATTTTTTAAATGGAAT
                                  901                                                                                                  1000
Gm11:11529579-11531009   (901)    ATTATTTTGCATTTAAAATGAAAAATATATATGGTGGATTTGAGTGTGTGCACACATGTATCTTTCTTAAGTTGACAGGTAGCATAGTTTTAAATAAGTT
           GM-AGB1 PRO   (901)    ATTATTTTGCATTTAAAATGAAAAATATATATGGTGGATTTGAGTGTGTGCACACATGTATCTTTCTTAAGTTGACAGGTAGCATAGTTTTAAATAAGTT
                                  1001                                                                                                 1100
Gm11:11529579-11531009  (1001)    TTTGTCTTTTATAACAAATAATTTTCCGTCTACACAACTATTATATTCAACAAAAAATAAAATTAACACAGTTCCACATATAAACGTTAAAAATTTAACT
           GM-AGB1 PRO  (1001)    TTTGTCTTTTATAACAAATAATTTTCCGTCTACACAACTATTATATTCAACAAAAAATAAAATTAACACAGTTCCACATATAAACGTTAAAAATTTAACT
                                  1101                                                                                                 1200
Gm11:11529579-11531009  (1101)    AAAGAAAGAAAATCATAAACGTTACGTTACATTCCTATTGGAATTGATATGATAAGCCTAGCCCAAGAGAAAAGGGAAAATTTCCAAAATTTAAAGGGAA
           GM-AGB1 PRO  (1101)    AAAGAAAGAAAATCATAAACGTTACGTTACATTCCTATTGGAATTGATATGATAAGCCTAGCCCAAGAGAAAAGGGAAAATTTCCAAAATTTAAAGGGAA
                                  1201                                                                                                 1300
Gm11:11529579-11531009  (1201)    GAAGATAAGAAGACGCTGATGTTAGAGAATTTCAAGCAGACTTTGAATGTGTCACTGTGTTTGTGTCTTTGATCCGAAGTTTCTCACTGAACCTCAACAT
           GM-AGB1 PRO  (1201)    GAAGATAAGAAGACGCTGATGTTAGAGAATTTCAAGCAGACTTTGAATGTGTCACTGTGTTTGTGTCTTTGATCCGAAGTTTCTCACTGAACCTCAACAT
                                  1301                                                                                                 1400
Gm11:11529579-11531009  (1301)    GTCTACACATTACATCGCCAGCAAACCCCTCAAGCTCTACATGCACGACACGTGTCTCTACATTCTCTTCACACTCCCTTCATAAATAAACCACCCTTTC
           GM-AGB1 PRO  (1301)    GTCTACACATTACATCGCCAGCAAACCCCTCAAGCTCTACATGCACGACACGTGTCTCTACATTCTCTTCACACTCCCTTCATAAATAAACCACCCTTTC
                                  1401                          1431
Gm11:11529579-11531009  (1401)    TTCCATCCTCATCCCTCAAACACAGTCATGG
           GM-AGB1 PRO  (1401)    TTCCATCCTCATCCCTCAAACACAGCCATGG
```

SOYBEAN AGB1 PROMOTER AND ITS USE IN TISSUE-SPECIFIC EXPRESSION OF TRANSGENIC GENES IN PLANTS

This application claims the benefit of U.S. Patent Application Ser. No. 61/787,095, filed Mar. 15, 2013, which is herein incorporated by reference in its entirety.

FIELD OF THE INVENTION

This invention relates to a plant promoter GM-AGB1 and fragments thereof and their use in altering expression of at least one heterologous nucleotide sequence in plants in a tissue-specific manner.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities can be incorporated properly into the plant's genome. The newly integrated gene (or genes) coding sequence can then be expressed in the plant cell to exhibit the desired new trait or characteristic. It is important that appropriate regulatory signals be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters", if the promoters direct RNA synthesis preferentially in certain tissues (RNA synthesis may occur in other tissues at reduced levels). Since patterns of expression of a chimeric gene (or genes) introduced into a plant are controlled using promoters, there is an ongoing interest in the isolation of novel promoters that are capable of controlling the expression of a chimeric gene (or genes) at certain levels in specific tissue types or at specific plant developmental stages.

Although advances in technology provide greater success in transforming plants with chimeric genes, there is still a need for specific expression of such genes in desired plants. Often times it is desired to selectively express target genes in a specific tissue because of toxicity or efficacy concerns. For example, embryo tissue is a type of tissue where specific expression is desirable and there remains a need for promoters that preferably initiate transcription in embryo tissue. Promoters that initiate transcription preferably in embryo tissue control genes involved in embryo and seed development.

SUMMARY OF THE INVENTION

This invention concerns a recombinant DNA construct comprising a promoter wherein said promoter comprises the nucleotide sequence set forth in SEQ ID NOs: 1, 2, 3, 4, 5, 6, or 41 or said promoter comprises a functional fragment of the nucleotide sequence set forth in SEQ ID NOs: 1, 2, 3, 4, 5, 6, or 41, or wherein said promoter comprises a nucleotide sequence having at least 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NOs: 1, 2, 3, 4, 5, 6, or 41, operably linked to at least one heterologous sequence.

In a second embodiment, the invention concerns a recombinant DNA construct comprising an isolated polynucleotide comprising a promoter region of the plasma membrane intrinsic protein (AGB1) *Glycine max* gene as set forth in SEQ ID NO: 1, wherein said promoter comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 100 6, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, or 1224 consecutive nucleotides, wherein the first nucleotide deleted is the cytosine nucleotide [C] at position 1 of SEQ ID NO: 1, operably linked to at least one heterologous sequence. This invention also concerns a recombinant DNA construct comprising an isolated polynucleotide of the embodiments disclosed herein, wherein the polynucleotide is a tissue-specific promoter.

In a third embodiment, this invention concerns a recombinant DNA construct comprising at least one heterologous nucleotide sequence operably linked to the promoter of the disclosure.

In a fourth embodiment, this invention concerns a cell, plant, or seed comprising a recombinant DNA construct of the present disclosure.

In a fifth embodiment, this invention concerns plants comprising this recombinant DNA construct and seeds obtained from such plants.

In a sixth embodiment, this invention concerns a method of altering (increasing or decreasing) expression of at least one heterologous nucleic acid fragment in a plant cell which comprises:

(a) transforming a plant cell with the recombinant expression construct described above;

(b) growing fertile mature plants from the transformed plant cell of step (a);

(c) selecting plants containing the transformed plant cell wherein the expression of the heterologous nucleic acid fragment is increased or decreased.

In a seventh embodiment, this invention concerns a method for expressing a yellow fluorescent protein ZS-GREEN1 (GFP) in a host cell comprising:

(a) transforming a host cell with a recombinant expression construct comprising at least one ZS-GREEN1 nucleic acid fragment operably linked to a promoter wherein said promoter consists essentially of the nucleotide sequence set forth in SEQ ID NOs: 1, 2, 3, 4, 5, 6, or 41; and (b) growing the transformed host cell under conditions that are suitable for expression of the recombinant DNA construct, wherein expression of the recombinant DNA construct results in production of increased levels of ZS-GREEN1 protein in the transformed host cell when compared to a corresponding nontransformed host cell.

In an eighth embodiment, this invention concerns an isolated nucleic acid fragment comprising a plant predicted allergen Gly m Bd 28K peptide (AGB1) gene promoter.

In a ninth embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In a tenth embodiment, this invention concerns a recombinant DNA construct comprising an isolated polynucleotide linked to a heterologous nucleotide sequence. The heterologous nucleotide sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

BRIEF DESCRIPTION OF THE DRAWINGS AND SEQUENCE LISTINGS

The invention can be more fully understood from the following detailed description and the accompanying drawings and Sequence Listing that form a part of this application.

FIG. 1 is the relative expression of a soybean predicted allergen Gly m Bd 28K peptide (AGB1) gene (PSO417572, Glyma11g15870.1) in twenty-one soybean tissues by Illumina (Solexa) digital gene expression dual-tag-based mRNA profiling. The gene expression profile indicates that the AGB1 gene is expressed specifically in fully developing seeds.

FIG. 2A is AGB1 promoter copy number analysis by Southern. FIG. 2A is the image of a Southern blot hybridized with a 628 bp AGB1 promoter probe made with primers QC642-S3 and PSO360340Nco by PCR. FIG. 2B shows restriction enzyme recognitions sites in the AGB1 probe region.

FIG. 4A-4B shows the maps of plasmids pCR2.1-TOPO, QC642-1, QC330, and QC642-1Y containing a truncated 1075 bp AGB1 promoter. Other promoter deletion constructs QC642-2Y, QC642-3Y, QC642-4Y, and QC642-5Y containing the 816, 628, 417 and 207 bp truncated AGB1 promoters, respectively, have the same map configuration, except for the truncated promoter sequences.

Figure 1:
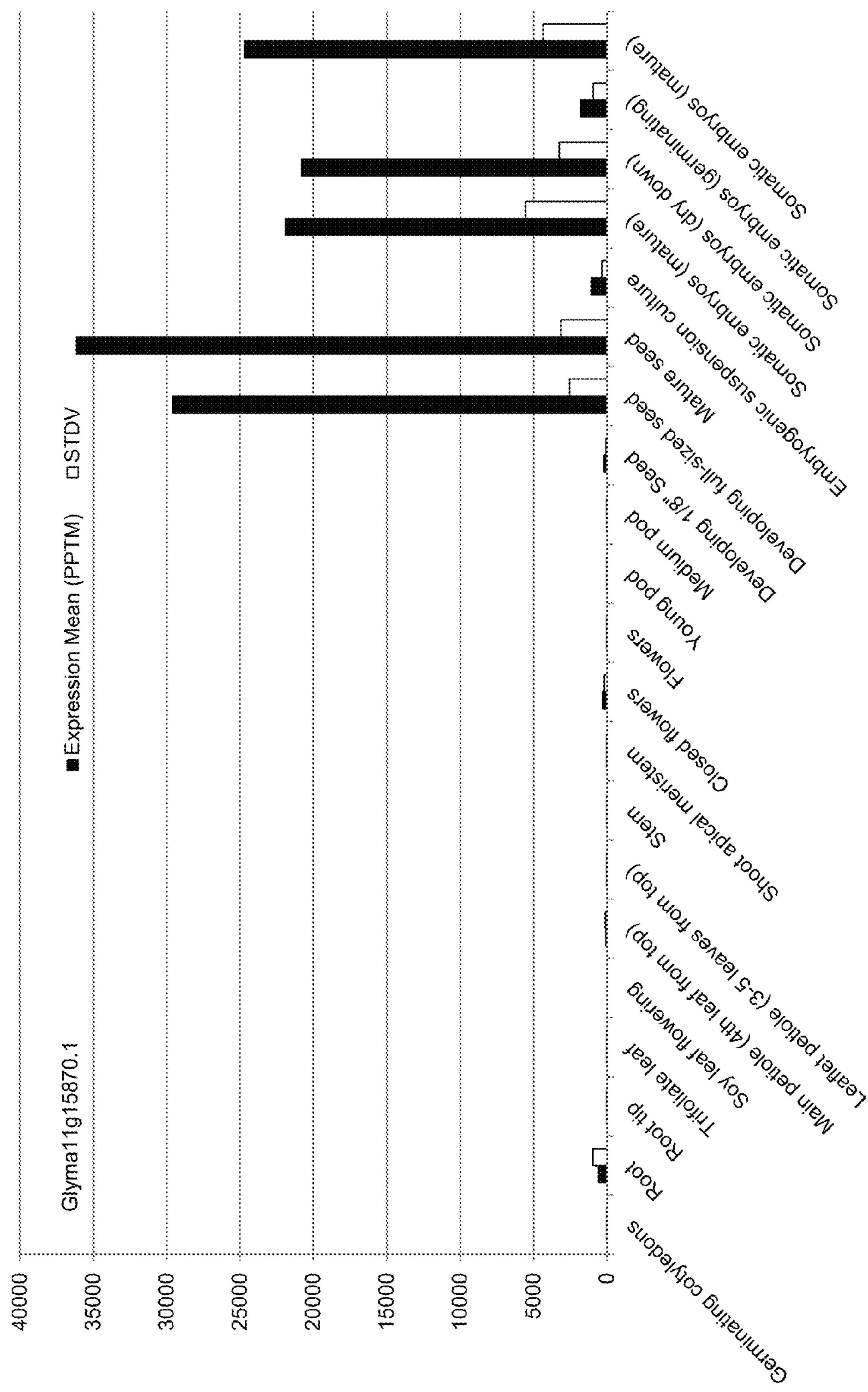

FIG. 6 is the transient expression of the fluorescent protein reporter gene ZS-GREEN1 (GFP) or ZS-YELLOW N1 (YFP) in the cotyledons of germinating soybean seeds. The reporter gene is driven by the full length AGB1 promoter in QC642 or by progressively truncated AGB1 promoters in the transient expression constructs QC642-1Y, QC642-2Y, QC642-3Y, QC642-4Y, and QC642-5Y. DNA construct pZSL90 used as a positive control has a strong constitutive promoter SCP1 driving ZS-YELLOW N1 gene and DNA construct QC330-Y used as a negative control contains a promoter-less YFP gene.

FIG. 7A-7P shows the stable expression of the fluorescent protein reporter gene ZS-GREEN1 in different tissues of transgenic soybean plants containing a single copy of AGB1:GFP DNA of construct QC651, comprising the 1431 bp AGB1 promoter of SEQ ID NO: 1. A: Embryonic callus, B-D: Developing somatic embryos, E: Opening flower, F: Pistil, G: Stamen, H: Pistil, longitudinal section showing ovules of an open flower, I: Leaf, J: Stem cross section, K: Leaf petiole, cross section, L: Root cross section, M-N: Developing pods showing developing seeds, P: Developing seeds cross sections.

FIG. 8 shows a nucleotide alignment of SEQ ID NO: 1, comprising the AGB1 promoter of the disclosure, and SEQ ID NO: 41, comprising a 1431 bp native soybean genomic DNA from Gm11:11529579-11531009 (Schmutz J. et al., Genome sequence of the palaeopolyploid soybean, Nature 463:178-183, 2010). Discrepant positions are underlined. The percent sequence identity between the two sequences based on the Clustal V method of alignment with pairwise alignment default parameters (KTUPLE=2, GAP PENALTY=5, WINDOW=4 and DIAGONALS SAVED=4) is given on the top right.

The sequence descriptions summarize the Sequence Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219 (2):345-373 (1984).

SEQ ID NO: 1 is a 1431 bp (base pair) DNA sequence comprising the full length soybean AGB1 promoter flanked by Xma1 (cccggg) and NcoI (ccatgg) restriction sites. Nucleotides 1411-1427 is a part of the 5' UTR (Un-Translated Region) sequence.

SEQ ID NO: 2 is a 1075 bp 5' end truncated form of the AGB1 promoter shown in SEQ ID NO: 1 including a 3' end NcoI cloning site.

SEQ ID NO: 3 is a 816 bp 5' end truncated form of the AGB1 promoter shown in SEQ ID NO: 1 including a 3' end NcoI cloning site.

SEQ ID NO: 4 is a 628 bp 5' end truncated form of the AGB1 promoter shown in SEQ ID NO: 1 including a 3' end NcoI cloning site.

SEQ ID NO: 5 is a 417 bp 5' end truncated form of the AGB1 promoter shown in SEQ ID NO: 1 including a 3' end NcoI cloning site.

SEQ ID NO: 6 is a 207 bp 5' end truncated form of the AGB1 promoter shown in SEQ ID NO: 1 including a 3' end NcoI cloning site.

SEQ ID NO: 7 is an oligonucleotide primer used as a gene-specific sense primer in the PCR amplification of the full length AGB1 promoter in SEQ ID NO: 1 when paired with SEQ ID NO: 8. A restriction enzyme XmaI recognition site CCCGGG is included for subsequent cloning.

SEQ ID NO: 8 is an oligonucleotide primer used as a gene-specific antisense primer in the PCR amplification of the full length AGB1 promoter in SEQ ID NO: 1 when paired with SEQ ID NO: 7. A restriction enzyme NcoI recognition site CCATGG is included for subsequent cloning.

SEQ ID NO: 9 is an oligonucleotide primer used as a gene-specific antisense primer in the PCR amplifications of the truncated AGB1 promoters in SEQ ID NOs: 2, 3, 4, 5, or 6 when paired with SEQ ID NOs: 10, 11, 12, 13, or 14, respectively SEQ ID NO: 7 is an oligonucleotide primer used as a sense primer in the PCR amplification of the truncated AGB1 promoter in SEQ ID NO: 2 when paired with SEQ ID NO: 9.

SEQ ID NO: 8 is an oligonucleotide primer used as a sense primer in the PCR amplification of the truncated AGB1 promoter in SEQ ID NO: 3 when paired with SEQ ID NO: 9.

SEQ ID NO: 12 is an oligonucleotide primer used as a sense primer in the PCR amplification of the truncated AGB1 promoter in SEQ ID NO: 4 when paired with SEQ ID NO: 9.

SEQ ID NO: 13 is an oligonucleotide primer used as a sense primer in the PCR amplification of the truncated AGB1 promoter in SEQ ID NO: 5 when paired with SEQ ID NO: 9.

SEQ ID NO: 14 is an oligonucleotide primer used as a sense primer in the PCR amplification of the truncated AGB1 promoter in SEQ ID NO: 6 when paired with SEQ ID NO: 9.

SEQ ID NO: 15 is the 1594 bp nucleotide sequence of the putative soybean predicted allergen Gly m Bd 28K peptide AGB1 cDNA (PSO360340 renamed as PSO417572 corresponding to Glyma11g15870.1). Nucleotides 1 to 17 are a part of the 5' untranslated sequence, nucleotides 18 to 20 are the translation initiation codon, nucleotides 18 to 1445 are the polypeptide coding region, nucleotides 1446 to 1448 are the termination codon, and nucleotides 1449 to 1594 are the 3' untranslated sequence.

SEQ ID NO: 12 is the predicted 476 aa (amino acid) long peptide sequence translated from the coding region of the putative soybean predicted allergen Gly m Bd 28K peptide AGB1 nucleotide sequence SEQ ID NO: 15.

SEQ ID NO: 17 is the 4774 bp sequence of plasmid QC642.

SEQ ID NO: 18 is the 8482 bp sequence of plasmid QC478i.

SEQ ID NO: 19 is the 9373 bp sequence of plasmid QC651.

SEQ ID NO: 15 is the 3887 bp sequence of plasmid QC642-1.

SEQ ID NO: 12 is the 5286 bp sequence of plasmid QC330.

SEQ ID NO: 17 is the 4728 bp sequence of plasmid QC642-1Y.

SEQ ID NO: 18 is the 4157 bp sequence of plasmid pZSL90.

SEQ ID NO: 19 is the 3640 bp sequence of plasmid QC330-Y.

SEQ ID NO: 20 is a sense primer used in quantitative PCR analysis of SAMS:HRA transgene copy numbers.

SEQ ID NO: 26 is a FAM labeled fluorescent DNA oligo probe used in quantitative PCR analysis of SAMS:HRA transgene copy numbers.

SEQ ID NO: 27 is an antisense primer used in quantitative PCR analysis of SAMS:HRA transgene copy numbers.

SEQ ID NO: 28 is a sense primer used in quantitative PCR analysis of GM-AGB1:GFP transgene copy numbers.

SEQ ID NO: 29 is a FAM labeled fluorescent DNA oligo probe used in quantitative PCR analysis of GM-AGB1:GFP transgene copy numbers.

SEQ ID NO: 30 is an antisense primer used in quantitative PCR analysis of GM-AGB1:GFP transgene copy numbers.

SEQ ID NO: 31 is a sense primer used as an endogenous control gene primer in quantitative PCR analysis of transgene copy numbers.

SEQ ID NO: 32 is a VIC labeled DNA oligo probe used as an endogenous control gene probe in quantitative PCR analysis of transgene copy numbers.

SEQ ID NO: 33 is an antisense primer used as an endogenous control gene primer in quantitative PCR analysis of transgene copy numbers.

SEQ ID NO: 34 is the recombination site attL1 sequence in the GATEWAY® cloning system (Invitrogen, Carlsbad, Calif.).

SEQ ID NO: 35 is the recombination site attL2 sequence in the GATEWAY® cloning system (Invitrogen).

SEQ ID NO: 36 is the recombination site attR1 sequence in the GATEWAY® cloning system (Invitrogen).

SEQ ID NO: 37 is the recombination site attR2 sequence in the GATEWAY® cloning system (Invitrogen).

SEQ ID NO: 38 is the recombination site attB1 sequence in the GATEWAY® cloning system (Invitrogen).

SEQ ID NO: 39 is the recombination site attB2 sequence in the GATEWAY® cloning system (Invitrogen).

SEQ ID NO: 40 is the 1267 bp nucleotide sequence of the *Glycine max* predicted allergen Gly m Bd 28K peptide 1-like gene (NCBI accession XM_003537998 or AB046874) similar to the AGB1 gene (PSO417572) sequence SEQ ID NO: 15.

SEQ ID NO: 41 is a 1431 bp fragment of native soybean genomic DNA Gm11:11529579-11531009 complementary strand sequence from cultivar "Williams82" (Schmutz J. et al. Nature 463: 178-183, 2010).

SEQ ID NO: 42 is a 17 bp fragment of the 5' end untranslated region (5' UTR) of the GM-AGB1 gene PSO417572 contained in GM-AGB1 promoter.

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

In the context of this disclosure, a number of terms shall be utilized.

An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "soybean AGB1 promoter", "GM-AGB1 promoter" or "AGB1 promoter" are used interchangeably herein, and refer to the promoter of a putative *Glycine max* gene with significant homology to predicted allergen Gly m Bd 28K peptide (AGB1) genes of soybean that are deposited in National Center for Biotechnology Information (NCBI) database. The term "soybean AGB1 promoter" encompasses both a native soybean promoter and an engineered sequence comprising a fragment of the native soybean promoter with a DNA linker attached to facilitate cloning. A DNA linker may comprise a restriction enzyme site.

"Promoter" refers to a nucleic acid fragment capable of controlling transcription of another nucleic acid fragment. A promoter is capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Embryo-specific promoter" and "embryo-preferred promoter" are used interchangeably to refer to a promoter that is active during embryo development or expressed predominantly but not necessarily exclusively in embryo tissue.

"Developmentally regulated promoter" refers to a promoter whose activity is determined by developmental events.

"Constitutive promoter" refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

The AGB1 promoter nucleotide sequences and methods disclosed herein are useful in regulating tissue-specific expression of any heterologous nucleotide sequences in a host plant in order to alter the phenotype of a plant. The tissues in which the AGB1 promoter is specifically expressed include developing embryos.

A "heterologous nucleotide sequence" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The present invention encompasses functional fragments of the promoter sequences disclosed herein.

A "functional fragment" refer to a portion or subsequence of the promoter sequence of the present invention in which the ability to initiate transcription or drive gene expression (such as to produce a certain phenotype) is retained. Fragments can be obtained via methods such as site-directed mutagenesis and synthetic construction. As with the provided promoter sequences described herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant. Recombinant DNA constructs can be designed for use in co-suppression or antisense by linking a promoter fragment in the appropriate orientation relative to a heterologous nucleotide sequence.

A nucleic acid fragment that is functionally equivalent to the promoter of the present invention is any nucleic acid fragment that is capable of controlling the expression of a coding sequence or functional RNA in a similar manner to the promoter of the present invention.

In an embodiment of the present invention, the promoters disclosed herein can be modified. Those skilled in the art can create promoters that have variations in the polynucleotide sequence. The polynucleotide sequence of the promoters of the present invention as shown in SEQ ID NOs: 1-6, may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Methods for construction of chimeric and variant promoters of the present invention include, but are not limited to, combining control elements of different promoters or duplicating portions or regions of a promoter (see for example, U.S. Pat. No. 4,990,607; U.S. Pat. No. 5,110,732; and U.S.

Pat. No. 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In some aspects of the present invention, the promoter fragments can comprise a deletion at the 5'-terminus of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 100 6, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223 or 1224 contiguous nucleotides of SEQ ID NO:1. In other embodiment, the promoter fragments can comprise at least about 20, or at least about 50 contiguous nucleotides, or at least about 75 contiguous nucleotides, or at least about 100 contiguous nucleotides, or at least about 150 contiguous nucleotides, or at least about 200 contiguous nucleotides of SEQ ID NO: 1, SEQ ID NO: 2, SEQ ID NO: 3, SEQ ID NO: 4, SEQ ID NO: 5, SEQ ID NO: 6, or SEQ ID NO: 41. In another aspect of the present invention, the promoter fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides, or at least about 1100 contiguous nucleotides, or at least about 1150 contiguous nucleotides, or at least about 1200 contiguous nucleotides of SEQ ID NO: 1. In another aspect, a promoter fragment is the nucleotide sequence set forth in SEQ ID NO: 2, SEQ ID NO: 3, SEQ ID NO: 4, SEQ ID NO: 5, SEQ ID NO: 6, or SEQ ID NO: 41. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "full complement" and "full-length complement" are used interchangeably herein, and refer to a complement of a given nucleotide sequence, wherein the complement and the nucleotide sequence consist of the same number of nucleotides and are 100% complementary.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The isolated promoter sequence of the present invention can be modified to provide a range of tissue-specific expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-specific nature of expression may be changed.

Modifications of the isolated promoter sequences of the present invention can provide for a range of tissue-specific expression of the heterologous nucleotide sequence. Thus, they may be modified to be weak tissue-specific promoters or strong tissue-specific promoters. Generally, by "weak promoter" is intended a promoter that drives expression of a coding sequence at a low level. By "low level" is intended at levels about 1/10,000 transcripts to about 1/100,000 transcripts to about 1/500,000 transcripts. Conversely, a strong promoter drives expression of a coding sequence at high level, or at about 1/10 transcripts to about 1/100 transcripts to about 1/1,000 transcripts.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U. K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 72% to 100%, such as 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In one embodiment, this invention concerns a recombinant DNA construct comprising a promoter wherein said promoter comprises a nucleotide sequence having at least 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4) when compared to the nucleotide sequence of SEQ ID NO: 1. As described in Example 2, comparison of SEQ ID NO: 1 to a soybean cDNA library revealed that SEQ ID NOs: 1, 2, 3, 4, 5, 6, and 41 comprise a 5' untranslated region (5'UTR) of at least 17 base pairs (SEQ ID NO: 42). It is known to one of skilled in the art that a 5' UTR region can be altered (deletion or substitutions of bases) or replaced by an alternative 5'UTR while maintaining promoter activity.

This 5'UTR region represents (17/1431)*100=1.2% of SEQ ID NO: 1, (17/1075)*100=1.6% of SEQ ID NO: 2, (17/816)*100=2.1% of SEQ ID NO: 3, (17/628)*100=2.7% of SEQ ID NO: 4, (17/417)*100=6.4% of SEQ ID NO: 5, (17/207)*100=8.2% of SEQ ID NO: 6, respectively, indicating that an isolated polynucleotide of 98.8% sequence identity to SEQ ID NO: 1, or 98.4% sequence identity to SEQ ID NO: 2, or 97.9% sequence identity to SEQ ID NO: 3, or 97.3% sequence identity to SEQ ID NO: 4, or 93.6% sequence identity to SEQ ID NO: 5, or 91.8% sequence identity to SEQ ID NO: 6, can be generated while maintaining promoter activity.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the tissue-specific expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., *Comput. Appl. Biosci.* 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid).

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product e.g., an mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at posttranscriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41(2):113-123 (2005); Pickford et al, Cell. Mol. Life Sci. 60(5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Transient expression" refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; 2$^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen.

Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, *Arabidopsis*, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr. Opin. Cell Biol. 5, 242-246 (1993); Roberts et al. Annu. Rev. Plant Mol. Biol. 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Down regulation of the expression of the enzymes involved in raffinose saccharide synthesis, such as galactinol synthase for example, would be a desirable trait.

In certain embodiments, the present invention contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode), or drought resistance, oil quantity and quality, or those increasing yield or nutritional quality may be employed as desired.

A cDNA clone (NCBI accession AB046874) was identified as the soybean allergen Gly m Bd 28K gene since it encodes the same amino acid sequence as determined chemically from allergen Gly m Bd 28K peptide (Tsuji et al., Biochim. Biophys. Acta 1518:178-182 (2001)). Another almost identical sequence (NCBI accession XM_003537998) and several identical but apparently partial sequences all from soybean are deposited in NCBI database. However, BLAST search of the soybean genome sequence with the full length AB046874 sequence identified only one locus in chromosome 11 and another one with homology similar to the 3' end third with many mismatches in chromosome 12, suggesting that there is indeed only one allergen Gly m Bd 28K in soybean. The allergen Gly m Bd 28K protein sequence contains the conserved barrel domain of the 'cupin' superfamily ('cupa' is the Latin term for a small barrel) that includes 11S and 7S plant seed storage proteins, and germins. Several genes encoding vicilin-like antimicrobial peptides from soybean, *Medicago truncatula, Vitis vinifera*, etc. sharing similar sequences with allergen Gly m Bd 28K protein are identified from genome sequencing projects. It is demonstrated herein that the soybean predicted allergen Gly m Bd 28K peptide gene promoter GM-AGB1 can, in fact, be used as a tissue-specific promoter to drive expression of transgenes in plants, and that such promoter can be isolated and used by one skilled in the art.

This invention concerns a recombinant DNA construct comprising an isolated nucleic acid fragment comprising a tissue-specific predicted allergen Gly m Bd 28K peptide gene AGB1 promoter. This invention also concerns an isolated nucleic acid fragment comprising a promoter wherein said promoter consists essentially of the nucleotide sequence set forth in SEQ ID NO: 1, or a recombinant DNA construct comprising an isolated polynucleotide comprising a promoter wherein said promoter comprises the nucleotide sequence set forth in SEQ ID NOs: 1, 2, 3, 4, 5, 6, or 41 or a functional fragment of SEQ ID NOs: 1, 2, 3, 4, 5, 6, or 41.

The expression patterns of AGB1 gene and its promoter are set forth in Examples 1-7.

The promoter activity of the soybean genomic DNA fragment SEQ ID NO: 1 upstream of the AGB1 protein coding sequence was assessed by linking the fragment to a green fluorescence reporter gene, ZS-GREEN1 (GFP) (Tsien, Annu. Rev. Biochem. 67:509-544 (1998); Matz et al., Nat. Biotechnol. 17:969-973 (1999)), transforming the promoter:GFP expression cassette into soybean, and analyzing GFP expression in various cell types of the transgenic plants (see Example 6 and 7). GFP expression was detected specifically in certain tissues of the transgenic plants. These results indicated that the nucleic acid fragment contained a tissue-specific promoter.

It is clear from the disclosure set forth herein that one of ordinary skill in the art could perform the following procedure:

1) operably linking the nucleic acid fragment containing the AGB1 promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric AGB1 promoter:reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm.

3) testing for expression of the AGB1 promoter in various cell types of transgenic plant tissues, e.g., leaves, roots, flowers, seeds, transformed with the chimeric AGB1 promoter:reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention AGB1 promoter or a fragment that is substantially similar and functionally equivalent to any portion of the nucleotide sequence set forth in SEQ ID NOs: 1, 2, 3, 4, 5, 6, or 41 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one acetolactate synthase (ALS) nucleic acid fragment operably linked to AGB1 promoter, or combination of promoter elements, of the present invention. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. No. 5,605,011, U.S. Pat. No. 5,378,824). The mutated acetolactate synthase gene is also widely used in plant transformation to select transgenic plants.

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; 2$^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

Tissue-specific expression of chimeric genes in developing embryos makes the AGB1 promoter of the instant invention especially useful when such tissue-specific specific expression of a target heterologous nucleic acid fragment is required.

Another general application of the AGB1 promoter of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the AGB1 promoter of the present invention. (See U.S. Pat. No. 5,231,020, and PCT Publication No. WO 99/53050 published on Oct. 21, 1999, PCT Publication No. WO 02/00904 published on Jan. 3, 2002, and PCT Publication No. WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the AGB1 promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:

(a) transforming a plant cell with the recombinant expression construct described herein;

(b) growing fertile mature plants from the transformed plant cell of step (a);

(c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

Non-limiting examples of methods and compositions disclosed herein are as follows:

1. A recombinant DNA construct comprising:

(a) a nucleotide sequence comprising any one of the sequences set forth in SEQ ID NO: 1, SEQ ID NO: 2, SEQ ID NO: 3, SEQ ID NO: 4, SEQ ID NO: 5, SEQ ID NO: 6, or SEQ ID NO: 41; or, (b) a full-length complement of (a); or, (c) a nucleotide sequence comprising a sequence having at least 72% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of (a);

operably linked to at least one heterologous sequence, wherein said nucleotide sequence is a promoter.

2. The recombinant DNA construct of embodiment 1, wherein the promoter is a tissue-specific promoter.

3. The recombinant DNA construct of embodiment 1, wherein the nucleotide sequence of (c) has at least 95% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO: 1.

4. The recombinant DNA construct of embodiment 1, wherein the nucleotide sequence is SEQ ID NO: 41.

5. A recombinant DNA construct comprising a promoter region of the AGB1 *Glycine max* gene as set forth in SEQ ID NO: 1, wherein said promoter region comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 100 6, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 11311, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, or 1224 consecutive nucleotides, wherein the first nucleotide deleted is the cytosine nucleotide [C] at position 1 of SEQ ID NO: 1, operably linked to at least one heterologous sequence.

6. A vector comprising the recombinant DNA construct of embodiment 1.

7. A cell comprising the recombinant DNA construct of embodiment 1.

8. The cell of embodiment 8, wherein the cell is a plant cell.

9. A transgenic plant having stably incorporated into its genome the recombinant DNA construct of embodiment 1.

10. The transgenic plant of embodiment 9 wherein said plant is a dicot plant.

11. The transgenic plant of embodiment 10 wherein the plant is soybean.

12. A transgenic seed produced by the transgenic plant of embodiment 9, wherein the transgenic seed comprises the recombinant DNA construct of embodiment 1.

13. The recombinant DNA construct according to embodiment 1, wherein the at least one heterologous nucleotide sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.

14. The recombinant DNA construct according to embodiment 1, wherein the at least one heterologous nucleotide sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

15. A method of expressing a coding sequence or a functional RNA in a plant comprising:

a) introducing the recombinant DNA construct of embodiment 1 into the plant, wherein the at least one heterologous nucleotide sequence comprises a coding sequence or encodes a functional RNA;

b) growing the plant of step a); and c) selecting a plant displaying expression of the coding sequence or the functional RNA of the recombinant DNA construct.

16. A method of transgenically altering a marketable plant trait, comprising:

a) introducing a recombinant DNA construct of embodiment 6 into the plant;

b) growing a fertile, mature plant resulting from step a); and c) selecting a plant expressing the at least one heterologous nucleotide sequence in at least one plant tissue based on the altered marketable trait.

17. The method of embodiment 16 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

18. A method for altering expression of at least one heterologous nucleic acid fragment in plant comprising:

(a) transforming a plant cell with the recombinant DNA construct of embodiment 6;

(b) growing fertile mature plants from transformed plant cell of step (a); and (c) selecting plants containing the transformed plant cell wherein the expression of the heterologous nucleic acid fragment is increased or decreased.

19. The method of Embodiment 18 wherein the plant is a soybean plant.

20. A method for expressing a green fluorescent protein ZS-GREEN1 in a host cell comprising:

(a) transforming a host cell with the recombinant DNA construct of embodiment 1; and, (b) growing the transformed host cell under conditions that are suitable for expression of the recombinant DNA construct, wherein expression of the recombinant DNA construct results in production of increased levels of ZS-GREEN1 protein in the transformed host cell when compared to a corresponding non-transformed host cell.

21. A plant stably transformed with a recombinant DNA construct comprising a soybean tissue-specific promoter and a heterologous nucleic acid fragment operably linked to said tissue-specific promoter, wherein said tissue-specific promoter is a capable of controlling expression of said heterologous nucleic acid fragment in a plant cell, and further wherein said tissue-specific promoter comprises any one of the sequences set forth in SEQ ID NO: 1, SEQ ID NO: 2, SEQ ID NO: 3, SEQ ID NO: 4, SEQ ID NO: 5, SEQ ID NO: 6, or SEQ ID NO: 41.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean Tissue-Specific Promoter Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. If more EST sequences representing the same gene are frequently found from a tissue-specific cDNA library such as a flower library than from a leaf library, there is a possibility that the represented gene could be a flower preferred gene candidate. Likewise, if similar numbers of ESTs for the same gene were found in various libraries constructed from different tissues, the represented gene could be a constitutively expressed gene. Multiple EST sequences representing the same soybean gene were compiled electronically based on their overlapping sequence homology into a unique full length sequence representing the gene. These assembled unique gene sequences were accumulatively collected in Pioneer Hi-Bred Intl proprietary searchable databases.

To identify Tissue-specific promoter candidate genes, searches were performed to look for gene sequences that were found exclusively or at much higher frequencies in a tissue of interest than in other tissues. For example, a gene frequently found in flower but not in other tissues such as leaf, root, embryo, pod, may be flower promoter candidate. One unique gene PSO417572 (also known as PSO360340 in an earlier version database of assembled unique gene sequences) was identified in the search to be a moderate developing seed-specific promoter gene candidate. PSO417572 cDNA sequence (SEQ ID NO: 15) as well as its putative translated protein sequence (SEQ ID NO: 12) were used to search National Center for Biotechnology Information (NCBI) databases. Both PSO417572 nucleotide and amino acid sequences were found to have high homology to a soybean predicted allergen Gly m Bd 28K peptide 1-like (NCBI accession XM_003537998 OR AB046874).

Solexa digital gene expression dual-tag-based mRNA profiling using the Illumina (Genome Analyzer) GA2 machine is a restriction enzyme site anchored tag-based technology, in this regard similar to Mass Parallel Signature Sequence transcript profiling technique (MPSS), but with two key differences (Morrissy et al., Genome Res. 19:1825-1835 (2009); Brenner et al., Proc. Natl. Acad. Sci. USA 97:1665-70 (2000)). Firstly, not one but two restriction enzymes were used, DpnII and NlaI, the combination of which increases gene representation and helps moderate expression variances. The aggregate occurrences of all the resulting sequence reads emanating from these DpnII and NlaI sites, with some repetitive tags removed computationally were used to determine the overall gene expression levels. Secondly, the tag read length used here is 21 nucleotides, giving the Solexa tag data higher gene match fidelity than the shorter 17-mers used in MPSS. Soybean mRNA global gene expression profiles are stored in a Pioneer proprietary database TDExpress (Tissue Development Expression Browser). Candidate genes with different expression patterns can be searched, retrieved, and further evaluated.

The predicted allergen Gly m Bd 28K peptide gene PSO417572 (AGB1) corresponds to predicted gene Glyma11g15870.1 in the soybean genome, sequenced by the DOE-JGI Community Sequencing Program consortium (Schmutz J, et al., Nature 463:178-183 (2010)). The AGB1 expression profiles in twenty one tissues were retrieved from the TDExpress database using the gene ID Glyma11g15870.1 and presented as parts per ten millions (PPTM) averages of three experimental repeats (FIG. 1). The AGB1 gene is expressed the highest in young developing seeds and several folds lower in older developing seeds, flowers, young and medium pods. No AGB1 expression is detected in root, leaf, stem, or somatic embryos. AGB1 was thus selected as a young developing seed-specific candidate gene from which to clone a moderate embryo-specific promoter.

Example 2

Isolation of Soybean AGB1 Promoter

The PSO417572 cDNA sequence was BLAST searched against the soybean genome sequence database sequence (Schmutz J, et al., Nature 463:178-183 (2010)) to identify corresponding genomic DNA. The ~1.5 kb sequence upstream of the PSO417572 start codon ATG was selected as AGB1 promoter to be amplified by PCR (polymerase chain reaction). The primers shown in SEQ ID NO: 7 and 8 were then designed to amplify by PCR the putative full length 1431 bp AGB1 promoter from soybean genomic DNA (SEQ ID NO: 1). SEQ ID NO: 7 contains a recognition site for the restriction enzyme XmaI. SEQ ID NO: 8 contains a recognition site for the restriction enzyme NcoI. The 2 bp "TC" proceeding the ATG start codon of PSO417572 cDNA (SEQ ID NO: 15) were changed to "CC" by the PCR cloning. The XmaI and NcoI sites were included for subsequent cloning.

Figure 3A:
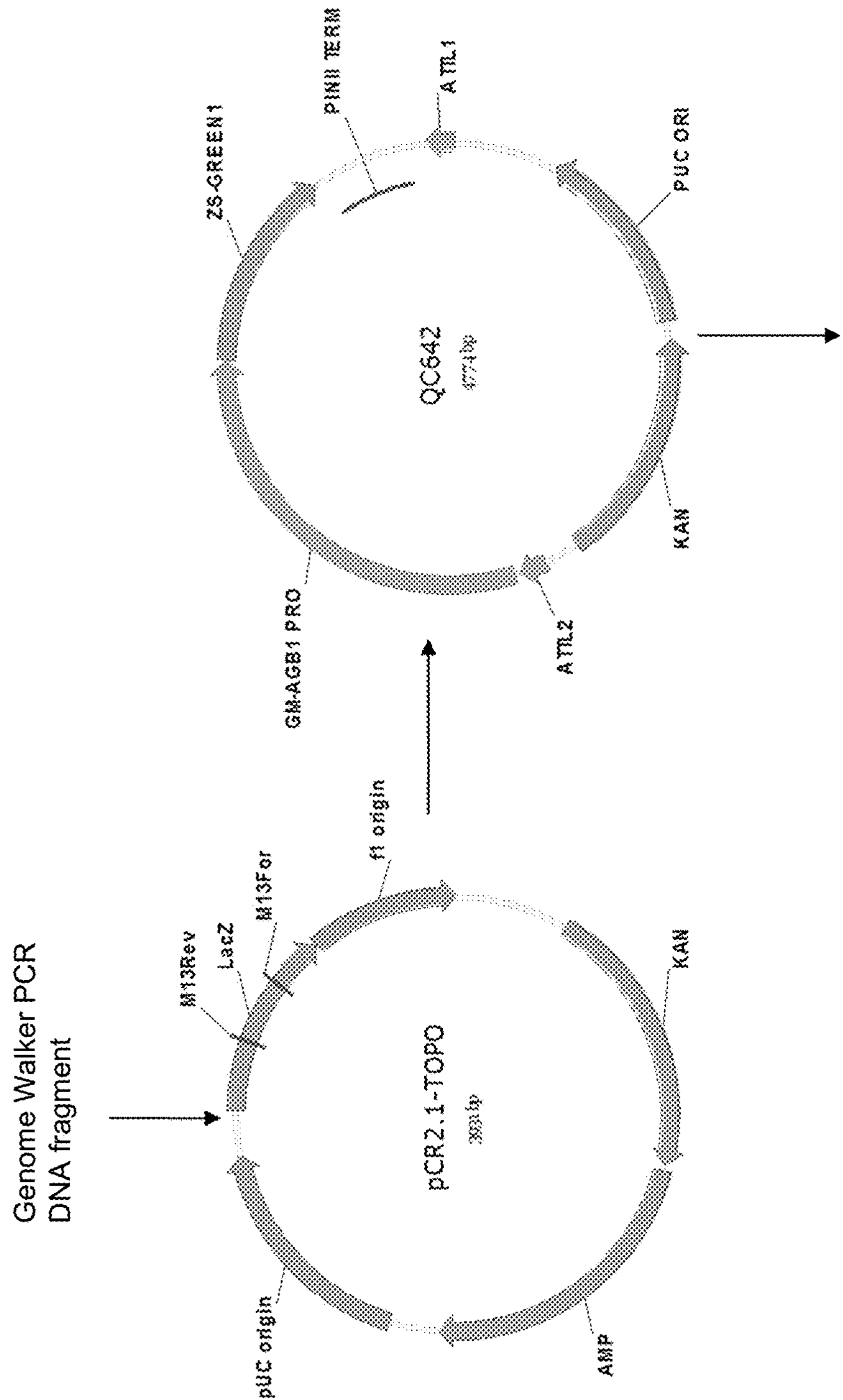
FIG. 3A-3B shows the maps of plasmids pCR2.1-TOPO, QC642, QC478i, and QC651. The 6859 bp AscI-AscI fragment of QC651 is used to produce transgenic soybean plants.

PCR cycle conditions were 94° C. for 4 minutes; 35 cycles of 94° C. for 30 seconds, 60° C. for 1 minute, and 68° C. for 2 minutes; and a final 68° C. for 5 minutes before holding at 4° C. using the Platinum high fidelity Taq DNA polymerase (Invitrogen). The PCR reaction was resolved using agarose gel electrophoresis to identify the right size PCR product representing the ~1.6 Kb AGB1 promoter. The PCR fragment was first cloned into pCR2.1-TOPO vector by TA cloning (Invitrogen). Several clones containing the ~1.6 Kb DNA insert were sequenced and only one clone with the correct AGB1 promoter sequence was selected for further cloning. The plasmid DNA of the selected clone was digested with XmaI and NcoI restriction enzymes to move the AGB1 promoter upstream of the ZS-GREEN1 (GFP) fluorescent reporter gene in QC642 (FIG. 3A, SEQ ID NO: 19). Construct QC642 contains the recombination sites AttL1 and AttL2 (SEQ ID NO: 34 and 35) to qualify as a GATEWAY® cloning entry vector (Invitrogen). The 1431 bp sequence upstream of the AGB1 gene PSO417572 start codon ATG including the XmaI and NcoI sites is herein designated as soybean AGB1 promoter GM-AGB1 PRO of SEQ ID NO: 1.

Comparison of PSO417572 cDNA sequence SEQ ID NO: 15 to soybean genome sequences revealed that SEQ ID NO: 15 comprised a 5' untranslated region (5' UTR) of at least 17 base pairs (SEQ ID NO: 42). The 17 bp 5' UTR is included in AGB1 promoter at its 3' end (SEQ ID NO: 1). It is known to one of skilled in the art that a 5' UTR region can be altered (deletion or substitutions of bases) or replaced by an alternative 5' UTR while maintaining promoter activity.

Example 3

AGB1 Promoter Copy Number Analysis

Figure 2:
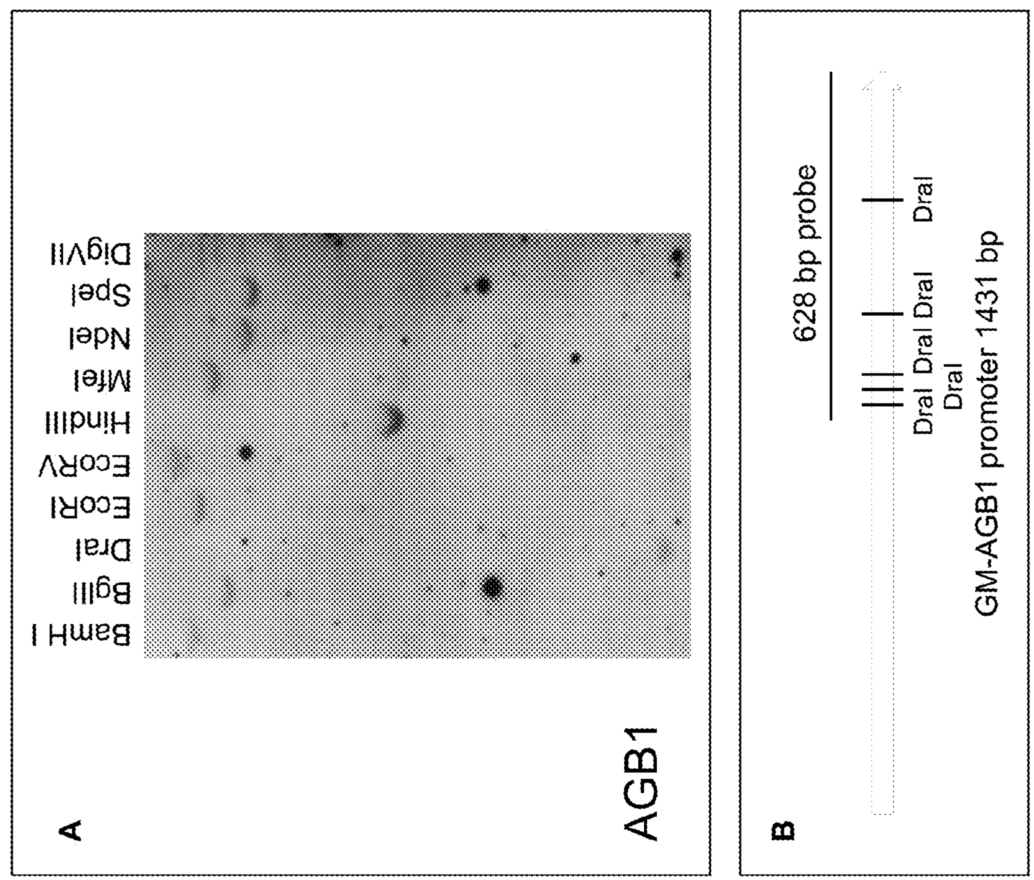

Southern hybridization analysis was performed to examine whether additional copies or sequences with significant similarity to the AGB1 promoter exist in the soybean genome. Soybean 'Jack' wild type genomic DNA was digested with nine different restriction enzymes, BamHI, BglII, DraI, EcoRI, EcoRV, HindIII, MfeI, NdeI, and SpeI and distributed in a 0.7% agarose gel by electrophoresis. The DNA was blotted onto Nylon membrane and hybridized at 60° C. with digoxigenin labeled AGB1 promoter DNA probe in Easy-Hyb Southern hybridization solution, and then sequentially washed 10 minutes with 2×SSC/0.1% SDS at room temperature and 3×10 minutes at 65° C. with 0.1× SSC/0.1% SDS according to the protocol provided by the manufacturer (Roche Applied Science, Indianapolis, Ind.). The AGB1 promoter probe was labeled by PCR using the DIG DNA labeling kit (Roche Applied Science) with primers QC642-S3 (SEQ ID NO: 12) and PSO360340Nco (SEQ ID NO: 8) and QC642 plasmid DNA (SEQ ID NO: 17) as the template to make a 628 bp long probe covering the 3' half of the AGB1 promoter (FIG. 2B).

Only one of the nine restriction enzymes DraI would cut the 628 bp AGB1 promoter probe region and only the resulted 3' end 239 bp fragment of the AGB1 probe would be large enough to hybridize stably to the genomic target sequence. A single AGB1 promoter fragment corresponding to the 3' portion of the 628 bp AGB1 probe downstream of the most 3' end DraI restriction site would be readily detected by Southern hybridization (FIG. 2B). None of the other eight restriction enzymes BamHI, BglII, EcoRI, EcoRV, HindIII, MfeI, NdeI, and SpeI would cut the AGB1 promoter probe region. Therefore, only one band would be expected to be hybridized for each of the nine digestions if only one copy of AGB1 promoter sequence exists in soybean genome (FIG. 2B). The observation that only one primary band was detected in each digestion with the nine enzymes suggested that there is only one copy of the AGB1 promoter sequence in soybean genome (FIG. 2A). The extra faint bands detected in MfeI digestion lane are likely non-specifically hybridized DNA fragments. The DIGVII molecular markers used on the Southern blot are 8576, 7427, 6106, 4899, 3639, 2799, 1953, 1882, 1515, 1482, 1164, 992, 718 and 710 bp.

Since the whole soybean genome sequence is now publically available (Schmutz J, et al., Nature 463:178-183 (2010)), the AGB1 promoter copy numbers can also be evaluated by searching the soybean genome with the 1431 bp promoter sequence (SEQ ID NO: 1). Consistent with above Southern analysis, only one sequence Gm11: 11529579-11531009 matching the AGB1 promoter sequence 1-1431 bp was identified (FIG. 8). The 5' end 6 bp and 3' end 6 bp of the 1431 bp AGB1 promoter may not match the genomic Gm011 sequence since they are artificially added XmaI and NcoI sites. No other sequences with significant homology to the AGB1 promoter sequence was found in soybean genome.

FIG. 8 shows a nucleotide sequence alignment of SEQ ID NO: 1, comprising the full length AGB1 promoter of the disclosure, and SEQ ID NO: 41, comprising a 1431 bp native soybean genomic DNA from Gm11:11529579-11531009 (Schmutz J. et al., Nature 463:178-183, 2010). As shown in the figure, the AGB1 promoter of SEQ ID NO: 1 is 99.7% identical to SEQ ID NO: 41, based on the Clustal Vmethod of alignment with pairwise alignment default parameters (KTUPLE=2, GAP PENALTY=5, WINDOW=4 and DIAGONALS SAVED=4). Based on the data described in Examples 1-7, it is believed that SEQ ID NO: 41 has promoter activity.

Example 4

AGB1:GFP Reporter Gene Constructs and Soybean Transformation

Figure 3B:
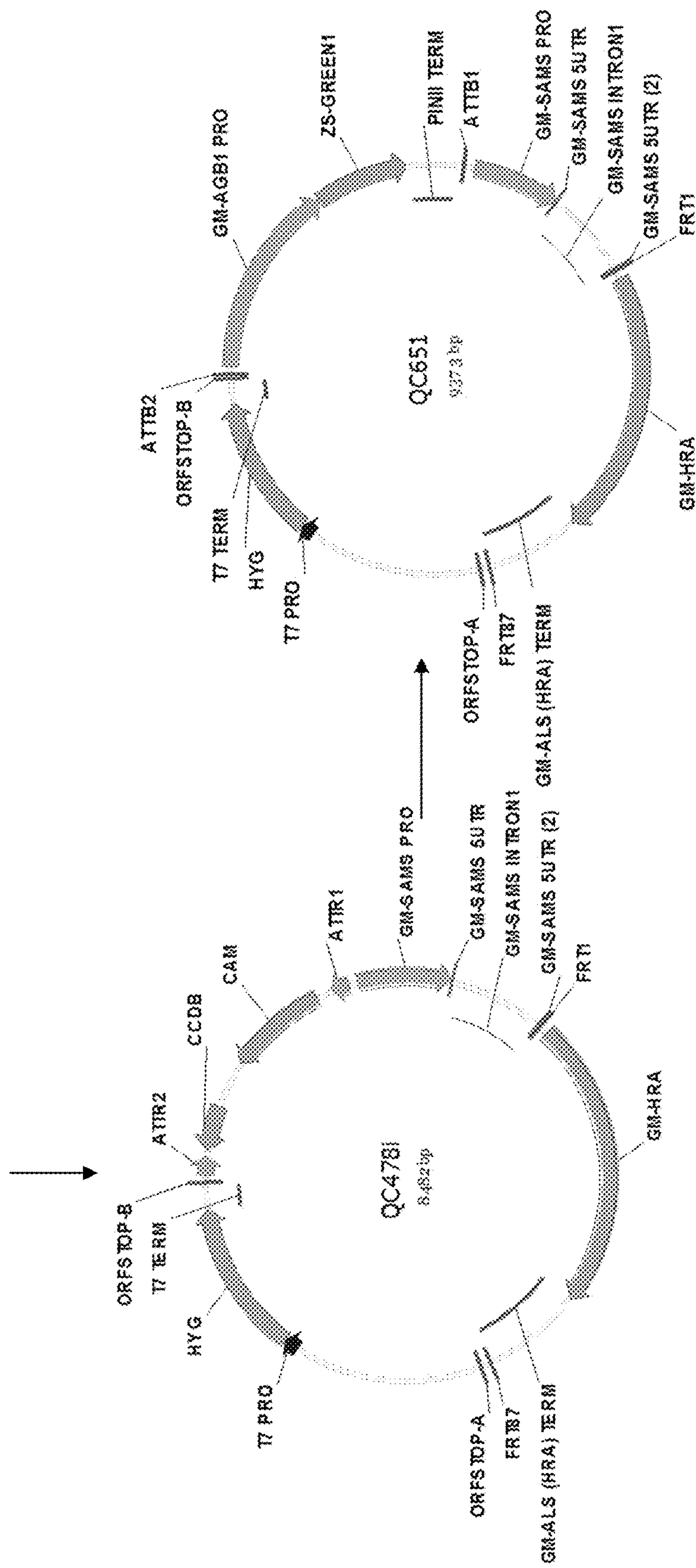

The AGB1:GFP cassette was moved from DNA construct QC642 (SEQ ID NO: 17) into a GATEWAY® destination vector QC478i (SEQ ID NO: 18) by LR Clonase® (Invitrogen) mediated DNA recombination between the attL1 and attL2 recombination sites (SEQ ID NO: 34, and 35, respectively) in QC642 and the attR1-attR2 recombination sites (SEQ ID NO: 36, and 37, respectively) in QC478i to make the final transformation construct QC651 (SEQ ID NO: 19; FIG. 3B).

Since the GATEWAY® destination vector QC478i already contains a soybean transformation selectable marker gene SAMS:HRA, the resulting DNA construct QC651 has the AGB1:GFP gene expression cassette linked to the SAMS:HRA cassette (FIG. 3B). Two 21 bp recombination sites attB1 and attB2 (SEQ ID NO: 38, and 39, respectively) were newly created recombination sites resulting from DNA recombination between attL1 and attR1, and between attL2 and attR2, respectively. The 6859 bp DNA fragment containing the linked AGB1:GFP and SAMS:HRA expression cassettes was isolated from plasmid QC651 (SEQ ID NO: 19) with AscI digestion, separated from the vector backbone fragment by agarose gel electrophoresis, and purified from the gel with a DNA gel extraction kit (QIAGEN®, Valencia, Calif.). The purified DNA fragment was transformed to soybean cultivar Jack by the method of particle gun bombardment (Klein et al., Nature 327:70-73 (1987); U.S. Pat. No. 4,945,050) as described in detail below to study the AGB1 promoter activity in stably transformed soybean plants.

The same methodology as outlined above for the AGB1:GFP expression cassette construction and transformation can be used with other heterologous nucleic acid sequences encoding for example a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 μl of a 60 mg/ml 1.0 mm gold particle suspension were added (in order): 30 μl of 30 ng/μl QC589 DNA fragment AGB1:GFP+SAMS:HRA, 20 μl of 0.1 M spermidine, and 25 μl of 5 M $CaCl_2$. The particle preparation was then agitated for 3 minutes, spun in a centrifuge for 10 seconds and the supernatant removed. The DNA-coated particles were then washed once in 400 μl 100% ethanol and resuspended in 45 μl of 100% ethanol. The DNA/particle suspension was sonicated three times for one second each. Then 5 μl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production.

Genomic DNA were extracted from somatic embryo samples and analyzed by quantitative PCR using a 7500 real time PCR system (Applied Biosystems, Foster City, Calif.) with gene-specific primers and FAM-labeled fluorescence probes to check copy numbers of both the SAMS:HRA expression cassette and the AGB1:GFP expression cassette. The qPCR analysis was done in duplex reactions with a heat shock protein (HSP) gene as the endogenous controls and a transgenic DNA sample with a known single copy of SAMS:HRA or GFP transgene as the calibrator. The endogenous control HSP probe was labeled with VIC and the target gene SAMS:HRA or GFP probe was labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

The primers and probes used in the qPCR analysis are listed below.

SAMS forward primer: SEQ ID NO: 20
FAM labeled ALS probe: SEQ ID NO: 26
ALS reverse primer: SEQ ID NO: 27
GFP forward primer: SEQ ID NO: 28
FAM labeled GFP probe: SEQ ID NO: 29
GFP reverse primer: SEQ ID NO: 30
HSP forward primer: SEQ ID NO: 31
VIC labeled HSP probe: SEQ ID NO: 32
HSP reverse primer: SEQ ID NO: 33

Only transgenic soybean events containing 1 or 2 copies of both the SAMS:HRA expression cassette and the AGB1:GFP expression cassette were selected for further gene expression evaluation and seed production (see Table 1). Events negative for GFP qPCR or with more than 2 copies for the SAMS:HRA qPCR were not further followed. GFP expressions are described in detail in EXAMPLE 7.

TABLE 1

Relative transgene copy numbers and GFP expression of AGB1:GFP transgenic plants

| Event ID | GFP expression | GFP qPCR | SAMS:HRA qPCR |
|---|---|---|---|
| 8831.1.1 | + | 0.9 | 0.3 |
| 8831.1.2 | + | 1.2 | 0.6 |
| 8831.1.3 | + | 1.7 | 0.7 |
| 8831.1.4 | + | 1.5 | 0.3 |
| 8831.1.5 | + | 0.8 | 0.8 |
| 8831.1.6 | − | 1.0 | 0.8 |
| 8831.1.7 | + | 1.7 | 1.3 |
| 8831.1.8 | + | 1.5 | 0.9 |
| 8831.1.9 | + | 1.1 | 0.6 |
| 8831.1.10 | + | 1.0 | 0.7 |
| 8831.1.12 | + | 1.0 | 0.7 |
| 8831.2.1 | + | 1.2 | 0.6 |
| 8831.2.3 | + | 1.8 | 0.3 |
| 8831.2.4 | + | 1.0 | 0.8 |
| 8831.2.6 | + | 1.1 | 0.5 |
| 8831.2.7 | + | 0.9 | 0.6 |
| 8831.2.8 | + | 2.2 | 2.0 |
| 8831.2.9 | + | 1.2 | 0.8 |
| 8831.2.10 | + | 1.0 | 0.5 |
| 8831.2.12 | + | 1.0 | 0.4 |
| 8831.2.13 | + | 0.9 | 0.7 |
| 8831.2.16 | + | 1.6 | 0.4 |
| 8831.2.17 | + | 1.7 | 0.8 |
| 8831.2.19 | + | 1.1 | 0.8 |

Example 5

Construction of AGB1 Promoter Deletion Constructs

Figure 4A:
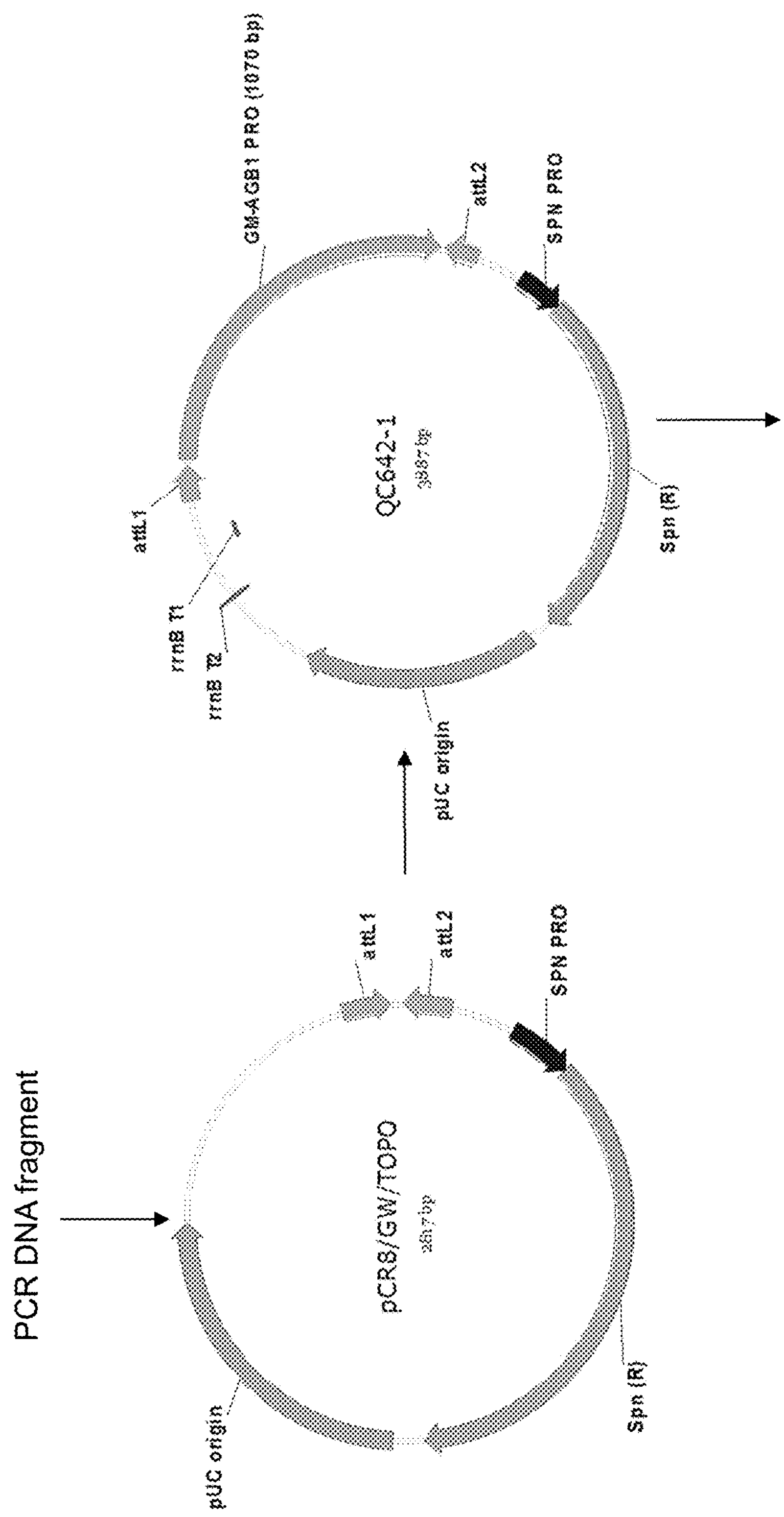

To define the transcriptional elements controlling the AGB1 promoter activity, seven 5' unidirectional deletion fragments 1075 bp, 816 bp, 628 bp, 417 bp, and 207 bp in length corresponding to SEQ ID NO: 2, 3, 4, 5, and 6, respectively, were made by PCR amplification from the full length soybean AGB1 promoter contained in the original construct QC642 (FIG. 3A). The 3' end restriction site NcoI sequence CCATGG is counted in the promoter lengths. The same antisense primer PSO360340Nco (SEQ ID NO: 8) was used in the amplification by PCR of all the five AGB1 promoter fragments (SEQ ID NOs: 2, 3, 4, 5, and 6) by pairing with different sense primers SEQ ID NOs: 10, 11, 12, 13, and 14, respectively. Each of the PCR amplified promoter DNA fragments was cloned into the GATEWAY® cloning entry vector pCR/GW/TOPO (Invitrogen, Carlsbad, Calif.) and confirmed by sequencing. The map of construct QC642-1 (SEQ ID NO: 20) containing the 1075 bp AGB1 promoter fragment (SEQ ID NO: 2) is shown in FIG. 4A. The maps of constructs QC642-2, 3, 4, and 5 containing the truncated AGB1 promoter fragments SEQ ID NOs: 2, 3, 4, 5, and 6 are similar to QC642-1 map and are not showed. Each AGB1 promoter fragment was subsequently cloned into a GATEWAY® destination vector QC330 (SEQ ID NO: 21) by GATEWAY® LR Clonase® reaction (Invitrogen). A 21 bp GATEWAY® recombination site attB2 (SEQ ID NO: 39) was left between the AGB1 promoter and YFP reporter gene cassette as a result of the GATEWAY® cloning process (FIG. 4B). The maps and sequences of constructs QC642-2Y, 3Y, 4Y, and 5Y containing the AGB1 promoter fragments SEQ ID NOs: 3, 4, 5, and 6 are similar to QC642-1Y map and are not showed.

The AGB1:YFP promoter deletion constructs were delivered into germinating soybean cotyledons by gene gun bombardment for transient gene expression study.

Figure 5:
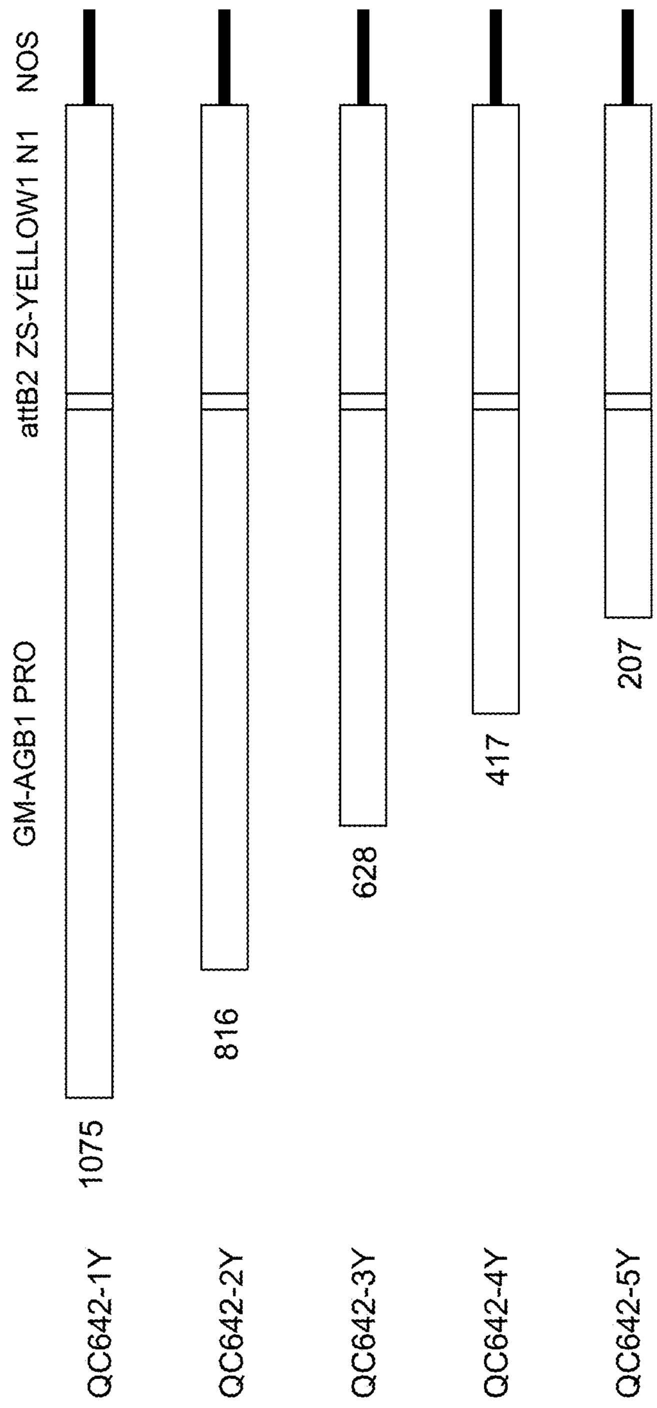
FIG. 5 is the schematic descriptions of the progressive truncations of the AGB1 promoter in constructs QC642-1Y, QC642-2Y, QC642-3Y, QC642-4Y, and QC642-5Y. The size of each promoter truncation including the 3' end NcoI cloning site is given at the left end of each drawing.

A similar construct pZSL90 with a synthetic constitutive promoter SCP1 driving YFP expression was used as positive control. A promoter-less construct QC330-Y was used as negative control (FIG. 4C). The five AGB1 promoter fragments analyzed are schematically described in FIG. 5.

Example 6

Transient Expression Analysis of AGB1:GFP Constructs

The constructs containing the full length and truncated AGB1 promoter fragments QC642, QC642-1Y, 2Y, 3Y, 4Y, and 5Y were tested by transiently expressing the ZS-YELLOW1 N1 (YFP) reporter gene in germinating soybean cotyledons. Soybean seeds were rinsed with 10% TWEEN® 20 in sterile water, surface sterilized with 70% ethanol for 2 minutes and then by 6% sodium hypochloride for 15 minutes. After rinsing the seeds were placed on wet filter paper in Petri dish to germinate for 4-6 days under light at 26° C. Green cotyledons were excised and placed inner side up on a 0.7% agar plate containing Murashige and Skoog media for particle gun bombardment. The DNA and gold particle mixtures were prepared similarly as described in EXAMPLE 4 except with more DNA (100 ng/μl). The bombardments were also carried out under similar parameters as described in EXAMPLE 4. YFP expression was checked under a Leica MZFLIII stereo microscope equipped with UV light source and appropriate light filters (Leica Microsystems Inc., Bannockburn, Ill.) and pictures were taken approximately 24 hours after bombardment with 8× magnification using a Leica DFC500 camera with settings as 0.60 gamma, 1.0 gain, 0.70 saturation, 61 color hue, 56 color saturation, and 0.51 second exposure.

The full length AGB1 promoter construct QC642 had similar fluorescence signals in transient expression assay compared to the positive control PZSL90 by showing similarly strong yellow dots in red background. Each dot represented a single cotyledon cell which appeared larger if the fluorescence signal was strong or smaller if the fluorescence signal was weak even under the same magnification (FIG. 6). Deletion constructs QC642-1Y and 2Y had more but slightly weaker yellow dots while QC642-3Y had fewer and also weaker yellow dots compared to the full length promoter construct QC642 (FIG. 6). QC642-4Y with a longer fragment deleted, however, had strong yellow dots than QC642-3Y. The shortest deletion construct QC642-5Y still showed similar yellow dots as QC642-3Y indicating that these promoter fragments including the shortest 207 bp AGB1 promoter in QC642-5Y are all functional as a promoter. The promoter-less negative control construct QC330-Y did not produce any yellow dots.

Example 7

AGB1:GFP Expression in Stable Transgenic Soybean Plants

The stable expression of the fluorescent protein reporter gene ZS-GREEN1 (GFP) driven by the full length AGB1 promoter (SEQ ID NO: 1) in transgenic soybean plants is shown in FIG. 7A-P.

ZS-GREEN1 (GFP) gene expression was tested at different stages of transgenic plant development for green fluorescence emission under a Leica MZFLIII stereo microscope equipped with appropriate fluorescent light filters. Green fluorescence was detected in embryogenic callus from which the somatic embryos originating but not in the embryos during early somatic embryo development period of soybean transformation (FIG. 7A). The negative section of a positive embryo cluster emitted dull red color due to auto fluorescence from the chlorophyll contained in soybean green tissues including embryos. The reddish green fluorescence indicated that the GFP expression was moderate since everything would be bright green if the GFP gene was driven by a strong promoter. Shortly afterwards, GFP expression was detected in the cotyledon base of differentiating somatic embryos placed on solid medium and throughout all later stages of somatic embryo development (FIG. 7B). Expression was strong fully developed and drying down somatic embryos as shown by the bright bluish green color and some parts so strong shown as white color (FIG. 7C-D).

When transgenic plants regenerated, YFP expression was not detected in any vegetative tissues such as leaf, stem, leaf petiole, and root (FIG. 7I-L). Other tissues are not shown.

No YFP expression was either detected in many reproductive tissues such as flower, pistil, stamen, and ovules (FIG. 7E-H). A soybean flower consists of five sepals, five petals including one standard large upper petal, two large side petals, and two small lower petals called kneel to enclose ten stamens and one pistil. The pistil consists of a stigma, a style, and an ovary in which there are 2-4 ovules. A stamen consists of a filament, and an anther on its tip. The filaments of nine of the stamens are fused and elevated as a single structure with a posterior stamen remaining separate. Pollen grains reside inside anther chambers and are released during pollination the day before the fully opening of the flower.

Green fluorescence signals were first detected in young developing seeds and getting stronger in older seeds from young R3 pod of ~5 mm long, to R4 full length pod of ~20 mm long and R5-R6 filled pod (FIG. 7M-O). No fluorescence signals were detected in any part of the pod coat. It was clear that the fluorescent signals were detected with increasing strengths in only the developing embryos rather than in seed coats when the developing seeds were crossly sectioned (FIG. 7P). The seed and pod development stages were defined according to descriptions in Fehr and Caviness, IWSRBC 80:1-12 (1977).

In conclusion, in addition to expression in embryonic callus during tissue culture, AGB1:YFP expression was detected strongly but only in developing somatic or zygotic embryos indicating that the soybean AGB1 promoter is a strong embryo-specific promoter.

What is claimed is:

1. A recombinant DNA construct comprising:

(a) a nucleotide sequence comprising any of the sequences set forth in SEQ ID NO:1, SEQ ID NO:2, SEQ ID NO:3, SEQ ID NO:4, SEQ ID NO:5, SEQ ID NO:6, or SEQ ID NO:41; or, (b) a full-length complement of (a); or, (c) a nucleotide sequence comprising a sequence having at least 99% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of (a);

operably linked to at least one heterologous sequence, wherein said nucleotide sequence is a tissue-specific promoter.

2. A recombinant DNA construct comprising a fragment of SEQ ID NO: 1 having at least 200 consecutive nucleotides of SEQ ID NO: 1 wherein said fragment is a tissue-specific promoter and wherein said fragment is operably linked to at least one heterologous nucleotide sequence.

3. The recombinant DNA construct of claim 1, wherein the nucleotide sequence of (c) has at least 99% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:1.

4. The recombinant DNA construct of claim 1, wherein the nucleotide sequence is SEQ ID NO: 41.

5. A recombinant DNA construct comprising a promoter region of the AGB1 *Glycine max* gene as set forth in SEQ ID NO:1, wherein said promoter region comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 100 6, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, or 1224 consecutive nucleotides, wherein the first nucleotide deleted is the cytosine nucleotide [C] at position 1 of SEQ ID NO: 1, operably linked to at least one heterologous sequence.

6. A vector comprising the recombinant DNA construct of claim 1.

7. A cell comprising the recombinant DNA construct of claim 1.

8. The cell of claim 7, wherein the cell is a plant cell.

9. A transgenic plant having stably incorporated into its genome the recombinant DNA construct of claim 1 or 2.

10. The transgenic plant of claim 9 wherein said plant is a dicot plant.

11. The transgenic plant of claim 10 wherein the plant is soybean.

12. A transgenic seed produced by the transgenic plant of claim 9 wherein the transgenic seed comprises the recombinant DNA construct.

13. The recombinant DNA construct according to claim 1, wherein the at least one heterologous nucleotide sequence comprises a nucleotide sequence selected from the group consisting of: a reporter nucleotide sequence, a selection marker nucleotide sequence, a disease resistance conferring nucleotide sequence, a herbicide resistance conferring nucleotide sequence, an insect resistance conferring nucleotide sequence; a nucleotide sequence involved in carbohydrate metabolism, a nucleotide sequence involved in fatty acid metabolism, a nucleotide sequence involved in amino acid metabolism, a nucleotide sequence involved in plant development, a nucleotide sequence involved in plant growth regulation, a nucleotide sequence involved in yield improvement, a nucleotide sequence involved in drought resistance, a nucleotide sequence involved in cold resistance, a nucleotide sequence involved in heat resistance and a nucleotide sequence involved in salt resistance in plants.

14. The recombinant DNA construct according to claim 1, wherein the at least one heterologous nucleotide sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

15. A method of expressing a coding sequence or a functional RNA in a plant comprising:

a) introducing the recombinant DNA construct of claim 1 into at least one plant cell, wherein the at least one heterologous nucleotide sequence comprises a coding sequence or encodes a functional RNA;

b) growing at least one plant from the at least one plant cell of step a); and, c) selecting a plant displaying expression of the coding sequence or the functional RNA of the recombinant DNA construct.

16. A method of transgenically altering a plant trait, comprising:

a) introducing the recombinant DNA construct of claim 1 into at least one plant cell;

b) growing at least one fertile, mature plant from the at least one plant cell of step a); and, c) selecting a plant expressing the at least one heterologous nucleotide sequence in at least one plant tissue based on the altered trait.

17. The method of claim 16 wherein the trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

18. A method for altering expression of at least one heterologous nucleic acid fragment in a plant comprising:

(a) transforming at least one plant cell with the recombinant DNA construct of claim 1;

(b) growing at least one fertile mature plant from transformed plant cell of step (a); and, (c) selecting a plant containing the transformed plant cell wherein the expression of the heterologous nucleic acid fragment is increased or decreased.

19. The method of claim 18 wherein the plant is a soybean plant.

20. A method for expressing a green fluorescent protein in a host cell comprising:

(a) transforming a host cell with the recombinant DNA construct of claim 1; and, (b) growing the transformed host cell under conditions that are suitable for expression of the recombinant DNA construct, wherein expression of the recombinant DNA construct results in production of increased levels of green fluorescent protein in the transformed host cell when compared to a corresponding non-transformed host cell.

21. A plant stably transformed with a recombinant DNA construct comprising a soybean tissue-specific promoter and a heterologous nucleic acid fragment operably linked to said tissue-specific promoter, wherein said tissue-specific promoter is a capable of controlling expression of said heterologous nucleic acid fragment in a plant cell, and further wherein said tissue-specific promoter comprises any of the sequences set forth in SEQ ID NO:1, SEQ ID NO:2, SEQ ID NO:3, SEQ ID NO:4, SEQ ID NO:5, SEQ ID NO:6, or SEQ ID NO: 41.

22. The recombinant DNA construct of claim 2 wherein the fragment is contained within a polynucleotide having at least 72% identify to SEQ ID NO: 1.

* * * * *

SEQUENCE LISTING

```
<160> NUMBER OF SEQ ID NOS: 42

<210> SEQ ID NO 1
<211> LENGTH: 1431
<212> TYPE: DNA
<213> ORGANISM: Glycine max

<400> SEQUENCE: 1

cccgggttgc gattgcttcg cgtcttgttc aaccttcaca cacacagatt caaacacgca     60

tctcttgctc ttcacagaga cacgatcttc ttttcttttt cgcataggca aaatcttggt    120

tgggataatc gaataaatta aatcaaaata atatggatta catattttaa tgttaaagaa    180

tctgaccgtt tgacgtctct aatctgctat aattaacttt caaaaattaa ctctgcataa    240

tgtgtaaaag ccactcaaaa aactaaggta acaataaaat gcatatagga ctaatatact    300

aacattaatt gaaacaattg atagtgattt ttgtctttta aacaagtgtt tcagtttttc    360

aatcatgtct taggtatgaa gcagattata aatcatattg gataaaaaat attcaaattt    420

attaattcac gaaggagatt tagtcacagt tatatggaac tttgttaatt ttgctcataa    480

ttttaacatt aaacttcttt agagggaggg ggttaattaa atgcaagagt atcttttgtg    540

ttaattgatt ttactctcca gtatacttat actactatta tatacgatta tgcaatataa    600

ttaattttta attaacagat aaaaattcat ttaagaatta tcaaacatcg tgtaaatagt    660

ttttcttttt cgcaagtata ctttatagga agtaactcta tttttcttaa aataacataa    720

aaagaaaaga aactcatttt ataagataat aagatgctaa atgtgagtag ctttagacat    780

ccacgaaatt tgaaccttga ttctctattt cacagtaaat tagtctatta aattcaacac    840

tattaatatg tgagaggatt taaatctttc tctattttat tttcattttt taaatggaat    900

attattttgc atttaaaatg aaaaatatat atggtggatt tgagtgtgtg cacacatgta    960

tctttcttaa gttgacaggt agcatagttt taaataagtt tttgtctttt ataacaaata   1020

attttccgtc tacacaacta ttatattcaa caaaaaataa aattaacaca gttccacata   1080

taaacgttaa aaatttaact aaagaaagaa aatcataaac gttacgttac attcctattg   1140

gaattgatat gataagccta gcccaagaga aaagggaaaa tttccaaaat ttaaagggaa   1200

gaagataaga agacgctgat gttagagaat ttcaagcaga ctttgaatgt gtcactgtgt   1260

ttgtgtcttt gatccgaagt ttctcactga acctcaacat gtctacacat tacatcgcca   1320

gcaaacccct caagctctac atgcacgaca cgtgtctcta cattctcttc acactccctt   1380

cataaataaa ccaccctttc ttccatcctc atccctcaaa cacagccatg g             1431


<210> SEQ ID NO 2
<211> LENGTH: 1075
<212> TYPE: DNA
<213> ORGANISM: Glycine max

<400> SEQUENCE: 2

tttcaatcat gtcttaggta tgaagcagat tataaatcat attggataaa aaatattcaa     60

atttattaat tcacgaagga gatttagtca cagttatatg gaactttgtt aattttgctc    120

ataattttaa cattaaactt ctttagaggg agggggttaa ttaaatgcaa gagtatcttt    180
```

```
tgtgttaatt gattttactc tccagtatac ttatactact attatatacg attatgcaat    240

ataattaatt tttaattaac agataaaaat tcatttaaga attatcaaac atcgtgtaaa    300

tagtttttct ttttcgcaag tatactttat aggaagtaac tctattttc ttaaaataac    360

ataaaaagaa aagaaactca ttttataaga taataagatg ctaaatgtga gtagctttag    420

acatccacga aatttgaacc ttgattctct atttcacagt aaattagtct attaaattca    480

acactattaa tatgtgagag gatttaaatc tttctctatt ttattttcat tttttaaatg    540

gaatattatt ttgcatttaa aatgaaaaat atatatggtg gatttgagtg tgtgcacaca    600

tgtatctttc ttaagttgac aggtagcata gttttaaata agtttttgtc ttttataaca    660

aataattttc cgtctacaca actattatat tcaacaaaaa ataaaattaa cacagttcca    720

catataaacg ttaaaaattt aactaaagaa agaaaatcat aaacgttacg ttacattcct    780

attggaattg atatgataag cctagcccaa gagaaaaggg aaaatttcca aaatttaaag    840

ggaagaagat aagaagacgc tgatgttaga gaatttcaag cagactttga atgtgtcact    900

gtgtttgtgt ctttgatccg aagtttctca ctgaacctca acatgtctac acattacatc    960

gccagcaaac ccctcaagct ctacatgcac gacacgtgtc tctacattct cttcacactc   1020

ccttcataaa taaaccaccc tttcttccat cctcatccct caaacacagc catgg        1075


<210> SEQ ID NO 3
<211> LENGTH: 816
<212> TYPE: DNA
<213> ORGANISM: Glycine max

<400> SEQUENCE: 3

cagataaaaa ttcatttaag aattatcaaa catcgtgtaa atagtttttc tttttcgcaa     60

gtatacttta taggaagtaa ctctattttt cttaaaataa cataaaaaga aaagaaactc    120

attttataag ataataagat gctaaatgtg agtagcttta gacatccacg aaatttgaac    180

cttgattctc tatttcacag taaattagtc tattaaattc aacactatta atatgtgaga    240

ggatttaaat ctttctctat tttattttca tttttaaat ggaatattat tttgcattta    300

aaatgaaaaa tatatatggt ggatttgagt gtgtgcacac atgtatcttt cttaagttga    360

caggtagcat agttttaaat aagtttttgt cttttataac aaataatttt ccgtctacac    420

aactattata ttcaacaaaa aataaaatta acacagttcc acatataaac gttaaaaatt    480

taactaaaga aagaaaatca taaacgttac gttacattcc tattggaatt gatatgataa    540

gcctagccca agagaaaagg gaaaatttcc aaaatttaaa gggaagaaga taagaagacg    600

ctgatgttag agaatttcaa gcagactttg aatgtgtcac tgtgtttgtg tctttgatcc    660

gaagtttctc actgaacctc aacatgtcta cacattacat cgccagcaaa cccctcaagc    720

tctacatgca cgacacgtgt ctctacattc tcttcacact cccttcataa ataaaccacc    780

ctttcttcca tcctcatccc tcaaacacag ccatgg                              816


<210> SEQ ID NO 4
<211> LENGTH: 628
<212> TYPE: DNA
<213> ORGANISM: Glycine max

<400> SEQUENCE: 4

tctatttcac agtaaattag tctattaaat tcaacactat taatatgtga gaggatttaa     60

atctttctct attttatttt catttttaa atggaatatt attttgcatt taaaatgaaa    120

aatatatatg gtggatttga gtgtgtgcac acatgtatct ttcttaagtt gacaggtagc    180
```

```
atagttttaa ataagttttt gtcttttata acaaataatt ttccgtctac acaactatta    240

tattcaacaa aaaataaaat taacacagtt ccacatataa acgttaaaaa tttaactaaa    300

gaaagaaaat cataaacgtt acgttacatt cctattggaa ttgatatgat aagcctagcc    360

caagagaaaa gggaaaattt ccaaaattta aagggaagaa gataagaaga cgctgatgtt    420

agagaatttc aagcagactt tgaatgtgtc actgtgtttg tgtctttgat ccgaagtttc    480

tcactgaacc tcaacatgtc tacacattac atcgccagca aaccccctcaa gctctacatg    540

cacgacacgt gtctctacat tctcttcaca ctcccttcat aaataaacca ccctttcttc    600

catcctcatc cctcaaacac agccatgg                                        628

<210> SEQ ID NO 5
<211> LENGTH: 417
<212> TYPE: DNA
<213> ORGANISM: Glycine max

<400> SEQUENCE: 5

caaataattt tccgtctaca caactattat attcaacaaa aaataaaatt aacacagttc     60

cacatataaa cgttaaaaat ttaactaaag aaagaaaatc ataaacgtta cgttacattc    120

ctattggaat tgatatgata agcctagccc aagagaaaag ggaaaatttc caaaatttaa    180

agggaagaag ataagaagac gctgatgtta gagaatttca agcagacttt gaatgtgtca    240

ctgtgtttgt gtctttgatc cgaagtttct cactgaacct caacatgtct acacattaca    300

tcgccagcaa acccctcaag ctctacatgc acgacacgtg tctctacatt ctcttcacac    360

tcccttcata aataaaccac cctttcttcc atcctcatcc ctcaaacaca gccatgg       417

<210> SEQ ID NO 6
<211> LENGTH: 207
<212> TYPE: DNA
<213> ORGANISM: Glycine max

<400> SEQUENCE: 6

gagaatttca agcagacttt gaatgtgtca ctgtgtttgt gtctttgatc cgaagtttct     60

cactgaacct caacatgtct acacattaca tcgccagcaa acccctcaag ctctacatgc    120

acgacacgtg tctctacatt ctcttcacac tcccttcata aataaaccac cctttcttcc    180

atcctcatcc ctcaaacaca gccatgg                                         207

<210> SEQ ID NO 7
<211> LENGTH: 22
<212> TYPE: DNA
<213> ORGANISM: Artificial sequence
<220> FEATURE:
<223> OTHER INFORMATION: Primer, PSO360340Xma

<400> SEQUENCE: 7

cccgggttgc gattgcttcg cg                                               22

<210> SEQ ID NO 8
<211> LENGTH: 29
<212> TYPE: DNA
<213> ORGANISM: Artificial sequence
<220> FEATURE:
<223> OTHER INFORMATION: Primer, PSO360340Nco

<400> SEQUENCE: 8

ccatggctgt gtttgaggga tgaggatgg                                        29
```

<210> SEQ ID NO 9
<211> LENGTH: 23
<212> TYPE: DNA
<213> ORGANISM: Artificial sequence
<220> FEATURE:
<223> OTHER INFORMATION: Primer, QC642-A

<400> SEQUENCE: 9
gctgtgtttg agggatgagg atg 23

<210> SEQ ID NO 10
<211> LENGTH: 28
<212> TYPE: DNA
<213> ORGANISM: Artificial sequence
<220> FEATURE:
<223> OTHER INFORMATION: Primer, QC642-S1

<400> SEQUENCE: 10
tttcaatcat gtcttaggta tgaagcag 28

<210> SEQ ID NO 11
<211> LENGTH: 34
<212> TYPE: DNA
<213> ORGANISM: Artificial sequence
<220> FEATURE:
<223> OTHER INFORMATION: Primer, QC642-S2

<400> SEQUENCE: 11
cagataaaaa ttcatttaag aattatcaaa catc 34

<210> SEQ ID NO 12
<211> LENGTH: 37
<212> TYPE: DNA
<213> ORGANISM: Artificial sequence
<220> FEATURE:
<223> OTHER INFORMATION: Primer, QC642-S3

<400> SEQUENCE: 12
tctatttcac agtaaattag tctattaaat tcaacac 37

<210> SEQ ID NO 13
<211> LENGTH: 34
<212> TYPE: DNA
<213> ORGANISM: Artificial sequence
<220> FEATURE:
<223> OTHER INFORMATION: Primer, QC642-S4

<400> SEQUENCE: 13
caaataattt tccgtctaca caactattat attc 34

<210> SEQ ID NO 14
<211> LENGTH: 27
<212> TYPE: DNA
<213> ORGANISM: Artificial sequence
<220> FEATURE:
<223> OTHER INFORMATION: Primer, QC642-S5

<400> SEQUENCE: 14
gagaatttca agcagacttt gaatgtg 27

<210> SEQ ID NO 15
<211> LENGTH: 1594
<212> TYPE: DNA
<213> ORGANISM: Glycine max

<400> SEQUENCE: 15

```
atccctcaaa cacagtcatg ggaaacaaaa ctacccttt gcttttgctc tttgttcttt     60
gtcatggagt ggccacaaca acaatggcct tccgtgatga tgagggtggt gataaaaagt    120
caccaaaaag tttgttttg atgagcaact ccacgagggt tttcaagact gatgcagggg    180
aaatgcgtgt gctgaaaagc catggtggta ggatatttta taggcacatg cacattggct    240
tcatctctat ggaaccaaag tccttgtttg ttcctcagta cctcgactcc aatctcatca    300
tattcatccg tagaggggaa gcaaagctgg gattcatata tgatgatgaa ctagcggaaa    360
ggagattgaa gacaggggac ttgtacatga ttccatctgg ttcagcattc tatttggtga    420
acataggaga aggtcagaga cttcacgtta tctgcagcat tgacccctct acaagcttgg    480
gattagagac cttccagtcc ttctatattg ggggaggagc caattcgcac tcggtgcttt    540
ctggattcga acctgccatc cttgaaactg catttaatga atcaagaacg gtggtagagg    600
aaatcttctc caaggaacta gatgggccaa ttatgttcgt ggatgattct catgcaccta    660
gcttatggac taaattcctt caactgaaga aggatgacaa agagcaacag ctgaagaaaa    720
tgatgcaaga ccaagaggag gatgaggagg agaagcaaac aagtaggtca tggaggaagc    780
tcttggaaac cgtatttggg aaggtgaatg agaagataga gaacaaagac actgctggtt    840
cccctgcctc ttacaacctc tacgatgaca aaaaagccga tttcaaaaac gcttatggtt    900
ggagcaaggc actgcatgga ggcgagtatc ctccactcag cgaaccggat attggagttt    960
tacttgtcaa actctcagcg ggatccatgt tggcacctca tgtgaatcca atatcagatg   1020
agtataccat agtgctgagt ggttatggtg aactgcatat agggtatcca aacggaagca   1080
aagcaatgaa aactaaaatc aaacaagggg acgtgtttgt tgtgccaaga tacttcccct   1140
tctgtcaagt agcatcaagg gatggaccct tagagttctt tggcttctcc acttctgcaa   1200
ggaagaacaa gccacagttt ctggctggtg ctgcgtccct tctaaggacc ttgatggggc   1260
cggagctttc ggcggcgttc ggagtgagcg aggacacgtt gcggcgcgct gttgatgctc   1320
agcatgaggc tgtgatactg ccatcagcat gggctgcacc accggaaaat gcagggaagc   1380
tgaagatgga agaagagcca aatgctatta gaagctttgc caatgatgtg gttatggatg   1440
tttttaatt tgaacacttg atttggaata ggggttattt ggtagtgcta gtgcctagtg   1500
gaattctgtg ttgagttttt tgttctttat atttagttga gatgtgtgtt gtgttcttga   1560
gttgtgaata aaaatctact ttctttgtgc attg                                1594
```

<210> SEQ ID NO 16
<211> LENGTH: 476
<212> TYPE: PRT
<213> ORGANISM: Glycine max

<400> SEQUENCE: 16

```
Met Gly Asn Lys Thr Thr Leu Leu Leu Leu Leu Phe Val Leu Cys His
1               5                   10                  15

Gly Val Ala Thr Thr Thr Met Ala Phe Arg Asp Asp Glu Gly Gly Asp
            20                  25                  30

Lys Lys Ser Pro Lys Ser Leu Phe Leu Met Ser Asn Ser Thr Arg Val
        35                  40                  45

Phe Lys Thr Asp Ala Gly Glu Met Arg Val Leu Lys Ser His Gly Gly
    50                  55                  60

Arg Ile Phe Tyr Arg His Met His Ile Gly Phe Ile Ser Met Glu Pro
65                  70                  75                  80

Lys Ser Leu Phe Val Pro Gln Tyr Leu Asp Ser Asn Leu Ile Ile Phe
```

```
                85                  90                  95

Ile Arg Arg Gly Glu Ala Lys Leu Gly Phe Ile Tyr Asp Asp Glu Leu
            100                 105                 110

Ala Glu Arg Arg Leu Lys Thr Gly Asp Leu Tyr Met Ile Pro Ser Gly
        115                 120                 125

Ser Ala Phe Tyr Leu Val Asn Ile Gly Glu Gly Gln Arg Leu His Val
    130                 135                 140

Ile Cys Ser Ile Asp Pro Ser Thr Ser Leu Gly Leu Glu Thr Phe Gln
145                 150                 155                 160

Ser Phe Tyr Ile Gly Gly Gly Ala Asn Ser His Ser Val Leu Ser Gly
                165                 170                 175

Phe Glu Pro Ala Ile Leu Glu Thr Ala Phe Asn Glu Ser Arg Thr Val
            180                 185                 190

Val Glu Glu Ile Phe Ser Lys Glu Leu Asp Gly Pro Ile Met Phe Val
        195                 200                 205

Asp Asp Ser His Ala Pro Ser Leu Trp Thr Lys Phe Leu Gln Leu Lys
    210                 215                 220

Lys Asp Asp Lys Glu Gln Gln Leu Lys Lys Met Met Gln Asp Gln Glu
225                 230                 235                 240

Glu Asp Glu Glu Glu Lys Gln Thr Ser Arg Ser Trp Arg Lys Leu Leu
                245                 250                 255

Glu Thr Val Phe Gly Lys Val Asn Glu Lys Ile Glu Asn Lys Asp Thr
            260                 265                 270

Ala Gly Ser Pro Ala Ser Tyr Asn Leu Tyr Asp Asp Lys Lys Ala Asp
        275                 280                 285

Phe Lys Asn Ala Tyr Gly Trp Ser Lys Ala Leu His Gly Gly Glu Tyr
    290                 295                 300

Pro Pro Leu Ser Glu Pro Asp Ile Gly Val Leu Leu Val Lys Leu Ser
305                 310                 315                 320

Ala Gly Ser Met Leu Ala Pro His Val Asn Pro Ile Ser Asp Glu Tyr
                325                 330                 335

Thr Ile Val Leu Ser Gly Tyr Gly Glu Leu His Ile Gly Tyr Pro Asn
            340                 345                 350

Gly Ser Lys Ala Met Lys Thr Lys Ile Lys Gln Gly Asp Val Phe Val
        355                 360                 365

Val Pro Arg Tyr Phe Pro Phe Cys Gln Val Ala Ser Arg Asp Gly Pro
    370                 375                 380

Leu Glu Phe Phe Gly Phe Ser Thr Ser Ala Arg Lys Asn Lys Pro Gln
385                 390                 395                 400

Phe Leu Ala Gly Ala Ala Ser Leu Leu Arg Thr Leu Met Gly Pro Glu
                405                 410                 415

Leu Ser Ala Ala Phe Gly Val Ser Glu Asp Thr Leu Arg Arg Ala Val
            420                 425                 430

Asp Ala Gln His Glu Ala Val Ile Leu Pro Ser Ala Trp Ala Ala Pro
        435                 440                 445

Pro Glu Asn Ala Gly Lys Leu Lys Met Glu Glu Glu Pro Asn Ala Ile
    450                 455                 460

Arg Ser Phe Ala Asn Asp Val Val Met Asp Val Phe
465                 470                 475
```

<210> SEQ ID NO 17
<211> LENGTH: 4774
<212> TYPE: DNA
<213> ORGANISM: Artificial sequence

```
<220> FEATURE:
<223> OTHER INFORMATION: Plasmid, QC642

<400> SEQUENCE: 17

gggttgcgat tgcttcgcgt cttgttcaac cttcacacac acagattcaa acacgcatct     60

cttgctcttc acagagacac gatcttcttt tctttttcgc ataggcaaaa tcttggttgg    120

gataatcgaa taaattaaat caaaataata tggattacat attttaatgt taaagaatct    180

gaccgtttga cgtctctaat ctgctataat taactttcaa aaattaactc tgcataatgt    240

gtaaaagcca ctcaaaaaac taaggtaaca ataaaatgca tataggacta atatactaac    300

attaattgaa acaattgata gtgatttttg tcttttaaac aagtgtttca gtttttcaat    360

catgtcttag gtatgaagca gattataaat catattggat aaaaaatatt caaatttatt    420

aattcacgaa ggagatttag tcacagttat atggaacttt gttaattttg ctcataattt    480

taacattaaa cttctttaga gggagggggt taattaaatg caagagtatc ttttgtgtta    540

attgatttta ctctccagta tacttatact actattatat acgattatgc aatataatta    600

atttttaatt aacagataaa aattcattta agaattatca aacatcgtgt aaatagtttt    660

tctttttcgc aagtatactt tataggaagt aactctattt ttcttaaaat aacataaaaa    720

gaaaagaaac tcattttata agataataag atgctaaatg tgagtagctt tagacatcca    780

cgaaatttga accttgattc tctatttcac agtaaattag tctattaaat tcaacactat    840

taatatgtga gaggatttaa atctttctct attttatttt catttttaa atggaatatt     900

attttgcatt taaaatgaaa aatatatatg gtggatttga gtgtgtgcac acatgtatct    960

ttcttaagtt gacaggtagc atagttttaa ataagttttt gtcttttata acaaataatt   1020

ttccgtctac acaactatta tattcaacaa aaaataaaat taacacagtt ccacatataa   1080

acgttaaaaa tttaactaaa gaaagaaaat cataaacgtt acgttacatt cctattggaa   1140

ttgatatgat aagcctagcc caagagaaaa gggaaaattt ccaaaattta aagggaagaa   1200

gataagaaga cgctgatgtt agagaatttc aagcagactt tgaatgtgtc actgtgtttg   1260

tgtctttgat ccgaagtttc tcactgaacc tcaacatgtc tacacattac atcgccagca   1320

aacccctcaa gctctacatg cacgacacgt gtctctacat tctcttcaca ctcccttcat   1380

aaataaacca ccctttcttc catcctcatc cctcaaacac agccatggcc cagtccaagc   1440

acggcctgac caaggagatg accatgaagt accgcatgga gggctgcgtg gacggccaca   1500

agttcgtgat caccggcgag ggcatcggct accccttcaa gggcaagcag gccatcaacc   1560

tgtgcgtggt ggagggcggc cccttgccct tcgccgagga catcttgtcc gccgccttca   1620

tgtacggcaa ccgcgtgttc accgagtacc cccaggacat cgtcgactac ttcaagaact   1680

cctgccccgc cggctacacc tgggaccgct ccttcctgtt cgaggacggc gccgtgtgca   1740

tctgcaacgc cgacatcacc gtgagcgtgg aggagaactg catgtaccac gagtccaagt   1800

tctacggcgt gaacttcccc gccgacggcc ccgtgatgaa gaagatgacc gacaactggg   1860

agccctcctg cgagaagatc atccccgtgc ccaagcaggg catcttgaag ggcgacgtga   1920

gcatgtacct gctgctgaag gacggtggcc gcttgcgctg ccagttcgac accgtgtaca   1980

aggccaagtc cgtgccccgc aagatgcccg actggcactt catccagcac aagctgaccc   2040

gcgaggaccg cagcgacgcc aagaaccaga agtggcacct gaccgagcac gccatcgcct   2100

ccggctccgc cttgccctcc ggactcagat ctcgactaga gtcgaaccta gacttgtcca   2160

tcttctggat tggccaactt aattaatgta tgaaataaaa ggatgcacac atagtgacat   2220
```

```
gctaatcact ataatgtggg catcaaagtt gtgtgttatg tgtaattact agttatctga   2280
ataaaagaga aagagatcat ccatatttct tatcctaaat gaatgtcacg tgtctttata   2340
attctttgat gaaccagatg catttcatta accaaatcca tatacatata aatattaatc   2400
atatataatt aatatcaatt gggttagcaa aacaaatcta gtctaggtgt gttttgcgaa   2460
ttctagtggc cggcccagct gatatccatc acactggcgg ccgcactcga ctgaattggt   2520
tccggcgcca gcctgctttt ttgtacaaag ttggcattat aaaaaagcat tgcttatcaa   2580
tttgttgcaa cgaacaggtc actatcagtc aaaataaaat cattatttgg ggcccgagct   2640
taagtaacta actaacagga agagtttgta gaaacgcaaa aaggccatcc gtcaggatgg   2700
ccttctgctt agtttgatgc ctggcagttt atggcgggcg tcctgcccgc caccctccgg   2760
gccgttgctt cacaacgttc aaatccgctc ccggcggatt tgtcctactc aggagagcgt   2820
tcaccgacaa acaacagata aaacgaaagg cccagtcttc cgactgagcc tttcgtttta   2880
tttgatgcct ggcagttccc tactctcgct tagtagttag acgtccccga gatccatgct   2940
agcggtaata cggttatcca cagaatcagg ggataacgca ggaaagaaca tgtgagcaaa   3000
aggccagcaa aaggccagga accgtaaaaa ggccgcgttg ctggcgtttt tccataggct   3060
ccgcccccct gacgagcatc acaaaaatcg acgctcaagt cagaggtggc gaaacccgac   3120
aggactataa agataccagg cgtttccccc tggaagctcc ctcgtgcgct ctcctgttcc   3180
gaccctgccg cttaccggat acctgtccgc ctttctccct tcgggaagcg tggcgctttc   3240
tcatagctca cgctgtaggt atctcagttc ggtgtaggtc gttcgctcca agctgggctg   3300
tgtgcacgaa ccccccgttc agcccgaccg ctgcgcctta tccggtaact atcgtcttga   3360
gtccaacccg gtaagacacg acttatcgcc actggcagca gccactggta acaggattag   3420
cagagcgagg tatgtaggcg gtgctacaga gttcttgaag tggtggccta actacggcta   3480
cactagaaga acagtatttg gtatctgcgc tctgctgaag ccagttacct tcggaaaaag   3540
agttggtagc tcttgatccg gcaaacaaac caccgctggt agcggtggtt tttttgtttg   3600
caagcagcag attacgcgca gaaaaaaagg atctcaagaa gatcctttga tcttttctac   3660
ggggtctgac gctcagtgga acggggccca atctgaataa tgttacaacc aattaaccaa   3720
ttctgattag aaaaactcat cgagcatcaa atgaaactgc aatttattca tatcaggatt   3780
atcaatacca tatttttgaa aaagccgttt ctgtaatgaa ggagaaaact caccgaggca   3840
gttccatagg atggcaagat cctggtatcg gtctgcgatt ccgactcgtc caacatcaat   3900
acaacctatt aatttcccct cgtcaaaaat aaggttatca agtgagaaat caccatgagt   3960
gacgactgaa tccggtgaga atggcaaaag tttatgcatt tctttccaga cttgttcaac   4020
aggccagcca ttacgctcgt catcaaaatc actcgcatca accaaaccgt tattcattcg   4080
tgattgcgcc tgagcgagac gaaatacgcg atcgctgtta aaaggacaat tacaaacagg   4140
aatcgaatgc aaccggcgca ggaacactgc cagcgcatca acaatatttt cacctgaatc   4200
aggatattct tctaatacct ggaatgctgt tttccgggg atcgcagtgg tgagtaacca   4260
tgcatcatca ggagtacgga taaaatgctt gatggtcgga agaggcataa attccgtcag   4320
ccagtttagt ctgaccatct catctgtaac atcattggca acgctacctt tgccatgttt   4380
cagaaacaac tctggcgcat cgggcttccc atacaagcga tagattgtcg cacctgattg   4440
cccgacatta tcgcgagccc atttataccc atataaatca gcatccatgt tggaatttaa   4500
tcgcggcctc gacgtttccc gttgaatatg gctcataaca ccccttgtat tactgtttat   4560
gtaagcagac agttttattg ttcatgatga tatattttta tcttgtgcaa tgtaacatca   4620
```

gagattttga gacacgggcc agagctgcag ctggatggca aataatgatt ttattttgac 4680
tgatagtgac ctgttcgttg caacaaattg ataagcaatg ctttcttata atgccaactt 4740
tgtacaagaa agctgggtct agatatctcg accc 4774

<210> SEQ ID NO 18
<211> LENGTH: 8482
<212> TYPE: DNA
<213> ORGANISM: Artificial sequence
<220> FEATURE:
<223> OTHER INFORMATION: Plasmid, QC478i

<400> SEQUENCE: 18
atcgaaccac tttgtacaag aaagctgaac gagaaacgta aaatgatata aatatcaata 60
tattaaatta gattttgcat aaaaaacaga ctacataata ctgtaaaaca caacatatcc 120
agtcactatg gtcgacctgc agactggctg tgtataaggg agcctgacat ttatattccc 180
cagaacatca ggttaatggc gtttttgatg tcattttcgc ggtggctgag atcagccact 240
tcttccccga taacggagac cggcacactg gccatatcgg tggtcatcat gcgccagctt 300
tcatccccga tatgcaccac cgggtaaagt tcacggggga ctttatctga cagcagacgt 360
gcactggcca gggggatcac catccgtcgc ccgggcgtgt caataatatc actctgtaca 420
tccacaaaca gacgataacg gctctctctt ttataggtgt aaaccttaaa ctgcatttca 480
ccagcccctg ttctcgtcag caaaagagcc gttcatttca ataaaccggg cgacctcagc 540
catcccttcc tgattttccg ctttccagcg ttcggcacgc agacgacggg cttcattctg 600
catggttgtg cttaccagac cggagatatt gacatcatat atgccttgag caactgatag 660
ctgtcgctgt caactgtcac tgtaatacgc tgcttcatag catacctctt tttgacatac 720
ttcgggtata catatcagta tatattctta taccgcaaaa atcagcgcgc aaatacgcat 780
actgttatct ggcttttagt aagccggatc ctctagatta cgccccgcct gccactcatc 840
gcagtactgt tgtaattcat taagcattct gccgacatgg aagccatcac aaacggcatg 900
atgaacctga atcgccagcg gcatcagcac cttgtcgcct tgcgtataat atttgcccat 960
ggtgaaaacg ggggcgaaga agttgtccat attggccacg tttaaatcaa aactggtgaa 1020
actcacccag ggattggctg agacgaaaaa catattctca ataaaccctt tagggaaata 1080
ggccaggttt tcaccgtaac acgccacatc ttgcgaatat atgtgtagaa actgccggaa 1140
atcgtcgtgg tattcactcc agagcgatga aaacgtttca gtttgctcat ggaaaacggt 1200
gtaacaaggg tgaacactat cccatatcac cagctcaccg tctttcattg ccatacggaa 1260
ttccggatga gcattcatca ggcgggcaag aatgtgaata aaggccggat aaaacttgtg 1320
cttatttttc tttacggtct ttaaaaaggc cgtaatatcc agctgaacgg tctggttata 1380
ggtacattga gcaactgact gaaatgcctc aaaatgttct ttacgatgcc attgggatat 1440
atcaacggtg gtatatccag tgattttttt ctccatttta gcttccttag ctcctgaaaa 1500
tctcgacgga tcctaactca aaatccacac attatacgag ccggaagcat aaagtgtaaa 1560
gcctggggtg cctaatgcgg ccgccatagt gactggatat gttgtgtttt acagtattat 1620
gtagtctgtt ttttatgcaa aatctaattt aatatattga tatttatatc attttacgtt 1680
tctcgttcag ctttttttgta caaacttgtt tgataaacac tagtaacggc cgccagtgtg 1740
ctggaattcg cccttcccaa gctttgctct agatcaaact cacatccaaa cataacatgg 1800
atatcttcct taccaatcat actaattatt ttgggttaaa tattaatcat tatttttaag 1860

-continued

```
atattaatta agaaattaaa agattttttta aaaaaatgta taaaattata ttattcatga   1920
tttttcatac atttgatttt gataataaat atattttttt taatttctta aaaaatgttg   1980
caagacactt attagacata gtcttgttct gtttacaaaa gcattcatca tttaatacat   2040
taaaaaatat ttaatactaa cagtagaatc ttcttgtgag tggtgtggga gtaggcaacc   2100
tggcattgaa acgagagaaa gagagtcaga accagaagac aaataaaaag tatgcaacaa   2160
acaaatcaaa atcaaagggc aaaggctggg gttggctcaa ttggttgcta cattcaattt   2220
tcaactcagt caacggttga gattcactct gacttcccca atctaagccg cggatgcaaa   2280
cggttgaatc taacccacaa tccaatctcg ttacttaggg gcttttccgt cattaactca   2340
cccctgccac ccggtttccc tataaattgg aactcaatgc tcccctctaa actcgtatcg   2400
cttcagagtt gagaccaaga cacactcgtt catatatctc tctgctcttc tcttctcttc   2460
tacctctcaa ggtacttttc ttctccctct accaaatcct agattccgtg gttcaatttc   2520
ggatcttgca cttctggttt gctttgcctt gctttttcct caactgggtc catctaggat   2580
ccatgtgaaa ctctactctt tctttaatat ctgcggaata cgcgtttgac tttcagatct   2640
agtcgaaatc atttcataat tgcctttctt tcttttagct tatgagaaat aaaatcactt   2700
ttttttatt tcaaaataaa ccttgggcct tgtgctgact gagatggggt ttggtgatta   2760
cagaatttta gcgaattttg taattgtact tgtttgtctg tagttttgtt ttgttttctt   2820
gtttctcata cattccttag gcttcaattt tattcgagta taggtcacaa taggaattca   2880
aactttgagc aggggaatta atcccttcct tcaaatccag tttgtttgta tatatgttta   2940
aaaaatgaaa cttttgcttt aaattctatt ataacttttt ttatggctga aatttttgca   3000
tgtgtctttg ctctctgttg taaatttact gtttaggtac taactctagg cttgttgtgc   3060
agtttttgaa gtataacaac agaagttcct attccgaagt tcctattctc tagaaagtat   3120
aggaacttcc accacacaac acaatggcgg ccaccgcttc cagaaccacc cgattctctt   3180
cttcctcttc acaccccacc ttccccaaac gcattactag atccaccctc cctctctctc   3240
atcaaaccct caccaaaccc aaccacgctc tcaaaatcaa atgttccatc tccaaacccc   3300
ccacggcggc gcccttcacc aaggaagcgc cgaccacgga gcccttcgtg tcacggttcg   3360
cctccggcga acctcgcaag ggcgcggaca tccttgtgga ggcgctggag aggcagggcg   3420
tgacgacggt gttcgcgtac cccggcggtg cgtcgatgga gatccaccag gcgctcacgc   3480
gctccgccgc catccgcaac gtgctcccgc gccacgagca gggcggcgtc ttcgccgccg   3540
aaggctacgc gcgttcctcc ggcctccccg gcgtctgcat tgccacctcc ggccccggcg   3600
ccaccaacct cgtgagcggc ctcgccgacg ctttaatgga cagcgtccca gtcgtcgcca   3660
tcaccggcca ggtcgcccgc cggatgatcg gcaccgacgc cttccaagaa accccgatcg   3720
tggaggtgag cagatccatc acgaagcaca actacctcat cctcgacgtc gacgacatcc   3780
cccgcgtcgt cgccgaggct ttcttcgtcg ccacctccgg ccgcccccggt ccggtcctca   3840
tcgacattcc caaagacgtt cagcagcaac tcgccgtgcc taattgggac gagcccgtta   3900
acctccccgg ttacctcgcc aggctgccca ggcccccgc cgaggcccaa ttggaacaca   3960
ttgtcagact catcatggag gcccaaaagc ccgttctcta cgtcggcggt ggcagtttga   4020
attccagtgc tgaattgagg cgctttgttg aactcactgg tattcccgtt gctagcactt   4080
taatgggtct tggaactttt cctattggtg atgaatattc ccttcagatg ctgggtatgc   4140
atggtactgt ttatgctaac tatgctgttg acaatagtga tttgttgctt gcctttgggg   4200
taaggtttga tgaccgtgtt actgggaagc ttgaggcttt tgctagtagg gctaagattg   4260
```

```
ttcacattga tattgattct gccgagattg ggaagaacaa gcaggcgcac gtgtcggttt   4320
gcgcggattt gaagttggcc ttgaagggaa ttaatatgat tttggaggag aaaggagtgg   4380
agggtaagtt tgatcttgga ggttggagag aagagattaa tgtgcagaaa cacaagtttc   4440
cattgggtta caagacattc caggacgcga tttctccgca gcatgctatc gaggttcttg   4500
atgagttgac taatggagat gctattgtta gtactggggt tgggcagcat caaatgtggg   4560
ctgcgcagtt ttacaagtac aagagaccga ggcagtggtt gacctcaggg ggtcttggag   4620
ccatgggttt tggattgcct gcggctattg gtgctgctgt tgctaaccct ggggctgttg   4680
tggttgacat tgatggggat ggtagtttca tcatgaatgt tcaggagttg gccactataa   4740
gagtggagaa tctcccagtt aagatattgt tgttgaacaa tcagcatttg ggtatggtgg   4800
ttcagttgga ggataggttc tacaagtcca atagagctca cacctatctt ggagatccgt   4860
ctagcgagag cgagatattc ccaaacatgc tcaagtttgc tgatgcttgt gggataccgg   4920
cagcgcgagt gacgaagaag gaagagctta gagcggcaat tcagagaatg ttggacaccc   4980
ctggccccta ccttcttgat gtcattgtgc cccatcagga gcatgtgttg ccgatgattc   5040
ccagtaatgg atccttcaag gatgtgataa ctgagggtga tggtagaacg aggtactgat   5100
tgcctagacc aaatgttcct tgatgcttgt tttgtacaat atatataaga taatgctgtc   5160
ctagttgcag gatttggcct gtggtgagca tcatagtctg tagtagtttt ggtagcaaga   5220
cattttattt tccttttatt taacttacta catgcagtag catctatcta tctctgtagt   5280
ctgatatctc ctgttgtctg tattgtgccg ttggattttt tgctgtagtg agactgaaaa   5340
tgatgtgcta gtaataatat ttctgttaga aatctaagta gagaatctgt tgaagaagtc   5400
aaaagctaat ggaatcaggt tacatattca atgtttttct ttttttagcg gttggtagac   5460
gtgtagattc aacttctctt ggagctcacc taggcaatca gtaaaatgca tattcctttt   5520
ttaacttgcc atttatttac ttttagtgga aattgtgacc aatttgttca tgtagaacgg   5580
atttggacca ttgcgtccac aaaacgtctc ttttgctcga tcttcacaaa gcgataccga   5640
aatccagaga tagttttcaa aagtcagaaa tggcaaagtt ataaatagta aaacagaata   5700
gatgctgtaa tcgacttcaa taacaagtgg catcacgttt ctagttctag acccatcagc   5760
tgggccggcc cagctgatga tcccggtgaa gttcctattc cgaagttcct attctccaga   5820
aagtatagga acttcactag agcttgcggc cgcgcatgct gacttaatca gctaacgcca   5880
ctcgaggggg ggcccggtac cggcgcgccg ttctatagtg tcacctaaat cgtatgtgta   5940
tgatacataa ggttatgtat taattgtagc cgcgttctaa cgacaatatg tccatatggt   6000
gcactctcag tacaatctgc tctgatgccg catagttaag ccagccccga cacccgccaa   6060
cacccgctga cgcgccctga cgggcttgtc tgctcccggc atccgcttac agacaagctg   6120
tgaccgtctc cgggagctgc atgtgtcaga ggttttcacc gtcatcaccg aaacgcgcga   6180
gacgaaaggg cctcgtgata cgcctatttt tataggttaa tgtcatgacc aaaatccctt   6240
aacgtgagtt ttcgttccac tgagcgtcag accccgtaga aaagatcaaa ggatcttctt   6300
gagatccttt ttttctgcgc gtaatctgct gcttgcaaac aaaaaaacca ccgctaccag   6360
cggtggtttg tttgccggat caagagctac caactctttt tccgaaggta actggcttca   6420
gcagagcgca gataccaaat actgtccttc tagtgtagcc gtagttaggc caccacttca   6480
agaactctgt agcaccgcct acatacctcg ctctgctaat cctgttacca gtggctgctg   6540
ccagtggcga taagtcgtgt cttaccgggt tggactcaag acgatagtta ccggataagg   6600
```

```
cgcagcggtc gggctgaacg gggggttcgt gcacacagcc cagcttggag cgaacgacct   6660

acaccgaact gagataccta cagcgtgagc attgagaaag cgccacgctt cccgaaggga   6720

gaaaggcgga caggtatccg gtaagcggca gggtcggaac aggagagcgc acgagggagc   6780

ttccaggggg aaacgcctgg tatctttata gtcctgtcgg gtttcgccac ctctgacttg   6840

agcgtcgatt tttgtgatgc tcgtcagggg ggcggagcct atggaaaaac gccagcaacg   6900

cggccttttt acggttcctg gccttttgct ggccttttgc tcacatgttc tttcctgcgt   6960

tatcccctga ttctgtggat aaccgtatta ccgcctttga gtgagctgat accgctcgcc   7020

gcagccgaac gaccgagcgc agcgagtcag tgagcgagga agcggaagag cgcccaatac   7080

gcaaaccgcc tctccccgcg cgttggccga ttcattaatg caggttgatc agatctcgat   7140

cccgcgaaat taatacgact cactataggg agaccacaac ggtttccctc tagaaataat   7200

tttgtttaac tttaagaagg agatataccc atggaaaagc ctgaactcac cgcgacgtct   7260

gtcgagaagt ttctgatcga aaagttcgac agcgtctccg acctgatgca gctctcggag   7320

ggcgaagaat ctcgtgcttt cagcttcgat gtaggagggc gtggatatgt cctgcgggta   7380

aatagctgcg ccgatggttt ctacaaagat cgttatgttt atcggcactt tgcatcggcc   7440

gcgctcccga ttccggaagt gcttgacatt ggggaattca gcgagagcct gacctattgc   7500

atctcccgcc gtgcacaggg tgtcacgttg caagacctgc ctgaaaccga actgcccgct   7560

gttctgcagc cggtcgcgga ggctatggat gcgatcgctg cggccgatct tagccagacg   7620

agcgggttcg gcccattcgg accgcaagga atcggtcaat acactacatg gcgtgatttc   7680

atatgcgcga ttgctgatcc ccatgtgtat cactggcaaa ctgtgatgga cgacaccgtc   7740

agtgcgtccg tcgcgcaggc tctcgatgag ctgatgcttt gggccgagga ctgccccgaa   7800

gtccggcacc tcgtgcacgc ggatttcggc tccaacaatg tcctgacgga caatggccgc   7860

ataacagcgg tcattgactg gagcgaggcg atgttcgggg attcccaata cgaggtcgcc   7920

aacatcttct tctggaggcc gtggttggct tgtatggagc agcagacgcg ctacttcgag   7980

cggaggcatc cggagcttgc aggatcgccg cggctccggg cgtatatgct ccgcattggt   8040

cttgaccaac tctatcagag cttggttgac ggcaatttcg atgatgcagc ttgggcgcag   8100

ggtcgatgcg acgcaatcgt ccgatccgga gccgggactg tcgggcgtac acaaatcgcc   8160

cgcagaagcg cggccgtctg gaccgatggc tgtgtagaag tactcgccga tagtggaaac   8220

cgacgcccca gcactcgtcc gagggcaaag gaatagtgag gtacagcttg gatcgatccg   8280

gctgctaaca aagcccgaaa ggaagctgag ttggctgctg ccaccgctga gcaataacta   8340

gcataacccc ttggggcctc taaacgggtc ttgaggggtt ttttgctgaa aggaggaact   8400

atatccggat gctcgggcgc gccggtaccc gggtaccgag ctcactagac gcggtgaaat   8460

tacctaatta acaccggtgt tt                                            8482
```

<210> SEQ ID NO 19
<211> LENGTH: 9373
<212> TYPE: DNA
<213> ORGANISM: Artificial sequence
<220> FEATURE:
<223> OTHER INFORMATION: Plasmid, QC651

<400> SEQUENCE: 19

```
cccgggttgc gattgcttcg cgtcttgttc aaccttcaca cacacagatt caaacacgca     60

tctcttgctc ttcacagaga cacgatcttc ttttcttttt cgcataggca aaatcttggt    120

tgggataatc gaataaatta aatcaaaata atatggatta catattttaa tgttaaagaa    180
```

```
tctgaccgtt tgacgtctct aatctgctat aattaacttt caaaaattaa ctctgcataa    240
tgtgtaaaag ccactcaaaa aactaaggta acaataaaat gcatatagga ctaatatact    300
aacattaatt gaaacaattg atagtgattt ttgtctttta aacaagtgtt tcagtttttc    360
aatcatgtct taggtatgaa gcagattata aatcatattg gataaaaaat attcaaattt    420
attaattcac gaaggagatt tagtcacagt tatatggaac tttgttaatt ttgctcataa    480
ttttaacatt aaacttcttt agagggaggg ggttaattaa atgcaagagt atcttttgtg    540
ttaattgatt ttactctcca gtatacttat actactatta tatacgatta tgcaatataa    600
ttaattttta attaacagat aaaaattcat ttaagaatta tcaaacatcg tgtaaatagt    660
ttttcttttt cgcaagtata ctttatagga agtaactcta tttttcttaa aataacataa    720
aaagaaaaga aactcatttt ataagataat aagatgctaa atgtgagtag ctttagacat    780
ccacgaaatt tgaaccttga ttctctattt cacagtaaat tagtctatta aattcaacac    840
tattaatatg tgagaggatt taaatctttc tctattttat tttcattttt taaatggaat    900
attattttgc atttaaaatg aaaaatatat atggtggatt tgagtgtgtg cacacatgta    960
tctttcttaa gttgacaggt agcatagttt taaataagtt tttgtctttt ataacaaata   1020
attttccgtc tacacaacta ttatattcaa caaaaaataa aattaacaca gttccacata   1080
taaacgttaa aaatttaact aaagaaagaa aatcataaac gttacgttac attcctattg   1140
gaattgatat gataagccta gcccaagaga aaagggaaaa tttccaaaat ttaaagggaa   1200
gaagataaga agacgctgat gttagagaat ttcaagcaga ctttgaatgt gtcactgtgt   1260
ttgtgtcttt gatccgaagt ttctcactga acctcaacat gtctacacat tacatcgcca   1320
gcaaacccct caagctctac atgcacgaca cgtgtctcta cattctcttc acactccctt   1380
cataaataaa ccaccctttc ttccatcctc atccctcaaa cacagccatg gcccagtcca   1440
agcacggcct gaccaaggag atgaccatga agtaccgcat ggagggctgc gtggacggcc   1500
acaagttcgt gatcaccggc gagggcatcg gctacccctt caagggcaag caggccatca   1560
acctgtgcgt ggtggagggc ggccccttgc ccttcgccga ggacatcttg tccgccgcct   1620
tcatgtacgg caaccgcgtg ttcaccgagt acccccagga catcgtcgac tacttcaaga   1680
actcctgccc cgccggctac acctgggacc gctccttcct gttcgaggac ggcgccgtgt   1740
gcatctgcaa cgccgacatc accgtgagcg tggaggagaa ctgcatgtac cacgagtcca   1800
agttctacgg cgtgaacttc cccgccgacg gccccgtgat gaagaagatg accgacaact   1860
gggagccctc ctgcgagaag atcatccccg tgcccaagca gggcatcttg aagggcgacg   1920
tgagcatgta cctgctgctg aaggacggtg gccgcttgcg ctgccagttc gacaccgtgt   1980
acaaggccaa gtccgtgccc cgcaagatgc ccgactggca cttcatccag cacaagctga   2040
cccgcgagga ccgcagcgac gccaagaacc agaagtggca cctgaccgag cacgccatcg   2100
cctccggctc cgccttgccc tccggactca gatctcgact agagtcgaac ctagacttgt   2160
ccatcttctg gattggccaa cttaattaat gtatgaaata aaaggatgca cacatagtga   2220
catgctaatc actataatgt gggcatcaaa gttgtgtgtt atgtgtaatt actagttatc   2280
tgaataaaag agaaagagat catccatatt tcttatccta aatgaatgtc acgtgtcttt   2340
ataattcttt gatgaaccag atgcatttca ttaaccaaat ccatatacat ataaatatta   2400
atcatatata attaatatca attgggttag caaaacaaat ctagtctagg tgtgttttgc   2460
gaattctagt ggccggccca gctgatatcc atcacactgg cggccgcact cgactgaatt   2520
```

```
ggttccggcg ccagcctgct tttttgtaca aacttgtttg ataaacacta gtaacggccg   2580
ccagtgtgct ggaattcgcc cttcccaagc tttgctctag atcaaactca catccaaaca   2640
taacatggat atcttcctta ccaatcatac taattatttt gggttaaata ttaatcatta   2700
tttttaagat attaattaag aaattaaaag attttttaaa aaaatgtata aaattatatt   2760
attcatgatt tttcatacat ttgattttga taataaatat atttttttta atttcttaaa   2820
aaatgttgca agacacttat tagacatagt cttgttctgt ttacaaaagc attcatcatt   2880
taatacatta aaaaatattt aatactaaca gtagaatctt cttgtgagtg gtgtgggagt   2940
aggcaacctg gcattgaaac gagagaaaga gagtcagaac cagaagacaa ataaaaagta   3000
tgcaacaaac aaatcaaaat caaagggcaa aggctggggt tggctcaatt ggttgctaca   3060
ttcaattttc aactcagtca acggttgaga ttcactctga cttccccaat ctaagccgcg   3120
gatgcaaacg gttgaatcta acccacaatc caatctcgtt acttaggggc ttttccgtca   3180
ttaactcacc cctgccaccc ggtttcccta taaattggaa ctcaatgctc ccctctaaac   3240
tcgtatcgct tcagagttga gaccaagaca cactcgttca tatatctctc tgctcttctc   3300
ttctcttcta cctctcaagg tacttttctt ctccctctac caaatcctag attccgtggt   3360
tcaatttcgg atcttgcact tctggtttgc tttgccttgc tttttcctca actgggtcca   3420
tctaggatcc atgtgaaact ctactctttc tttaatatct gcggaatacg cgtttgactt   3480
tcagatctag tcgaaatcat ttcataattg cctttctttc ttttagctta tgagaaataa   3540
aatcactttt tttttatttc aaaataaacc ttgggccttg tgctgactga gatggggttt   3600
ggtgattaca gaattttagc gaattttgta attgtacttg tttgtctgta gttttgtttt   3660
gttttcttgt ttctcataca ttccttaggc ttcaatttta ttcgagtata ggtcacaata   3720
ggaattcaaa ctttgagcag gggaattaat cccttccttc aaatccagtt tgtttgtata   3780
tatgtttaaa aaatgaaact tttgctttaa attctattat aacttttttt atggctgaaa   3840
tttttgcatg tgtctttgct ctctgttgta aatttactgt ttaggtacta actctaggct   3900
tgttgtgcag tttttgaagt ataacaacag aagttcctat tccgaagttc ctattctcta   3960
gaaagtatag gaacttccac cacacaacac aatggcggcc accgcttcca gaaccacccg   4020
attctcttct tcctcttcac accccacctt ccccaaacgc attactagat ccaccctccc   4080
tctctctcat caaaccctca ccaaacccaa ccacgctctc aaaatcaaat gttccatctc   4140
caaacccccc acggcggcgc ccttcaccaa ggaagcgccg accacggagc ccttcgtgtc   4200
acggttcgcc tccggcgaac ctcgcaaggg cgcggacatc cttgtggagg cgctggagag   4260
gcagggcgtg acgacggtgt tcgcgtaccc cggcggtgcg tcgatggaga tccaccaggc   4320
gctcacgcgc tccgccgcca tccgcaacgt gctcccgcgc cacgagcagg gcggcgtctt   4380
cgccgccgaa ggctacgcgc gttcctccgg cctccccggc gtctgcattg ccacctccgg   4440
ccccggcgcc accaacctcg tgagcggcct cgccgacgct ttaatggaca gcgtcccagt   4500
cgtcgccatc accggccagg tcgcccgccg gatgatcggc accgacgcct tccaagaaac   4560
cccgatcgtg gaggtgagca gatccatcac gaagcacaac tacctcatcc tcgacgtcga   4620
cgacatcccc cgcgtcgtcg ccgaggcttt cttcgtcgcc acctccggcc gccccggtcc   4680
ggtcctcatc gacattccca aagacgttca gcagcaactc gccgtgccta attgggacga   4740
gcccgttaac ctccccggtt acctcgccag gctgcccagg ccccccgccg aggcccaatt   4800
ggaacacatt gtcagactca tcatggaggc ccaaaagccc gttctctacg tcggcggtgg   4860
cagtttgaat tccagtgctg aattgaggcg ctttgttgaa ctcactggta ttcccgttgc   4920
```

```
tagcacttta atgggtcttg gaacttttcc tattggtgat gaatattccc ttcagatgct   4980
gggtatgcat ggtactgttt atgctaacta tgctgttgac aatagtgatt tgttgcttgc   5040
ctttggggta aggtttgatg accgtgttac tgggaagctt gaggcttttg ctagtagggc   5100
taagattgtt cacattgata ttgattctgc cgagattggg aagaacaagc aggcgcacgt   5160
gtcggtttgc gcggatttga agttggcctt gaagggaatt aatatgattt tggaggagaa   5220
aggagtggag ggtaagtttg atcttggagg ttggagagaa gagattaatg tgcagaaaca   5280
caagtttcca ttgggttaca agacattcca ggacgcgatt tctccgcagc atgctatcga   5340
ggttcttgat gagttgacta atggagatgc tattgttagt actggggttg ggcagcatca   5400
aatgtgggct gcgcagtttt acaagtacaa gagaccgagg cagtggttga cctcaggggg   5460
tcttggagcc atgggttttg gattgcctgc ggctattggt gctgctgttg ctaaccctgg   5520
ggctgttgtg gttgacattg atggggatgg tagtttcatc atgaatgttc aggagttggc   5580
cactataaga gtggagaatc tcccagttaa gatattgttg ttgaacaatc agcatttggg   5640
tatggtggtt cagttggagg ataggttcta caagtccaat agagctcaca cctatcttgg   5700
agatccgtct agcgagagcg agatattccc aaacatgctc aagtttgctg atgcttgtgg   5760
gataccggca gcgcgagtga cgaagaagga agagcttaga gcggcaattc agagaatgtt   5820
ggacacccct ggcccctacc ttcttgatgt cattgtgccc catcaggagc atgtgttgcc   5880
gatgattccc agtaatggat ccttcaagga tgtgataact gagggtgatg gtagaacgag   5940
gtactgattg cctagaccaa atgttccttg atgcttgttt tgtacaatat atataagata   6000
atgctgtcct agttgcagga tttggcctgt ggtgagcatc atagtctgta gtagttttgg   6060
tagcaagaca ttttattttc cttttattta acttactaca tgcagtagca tctatctatc   6120
tctgtagtct gatatctcct gttgtctgta ttgtgccgtt ggattttttg ctgtagtgag   6180
actgaaaatg atgtgctagt aataatattt ctgttagaaa tctaagtaga gaatctgttg   6240
aagaagtcaa aagctaatgg aatcaggtta catattcaat gtttttcttt ttttagcggt   6300
tggtagacgt gtagattcaa cttctcttgg agctcaccta ggcaatcagt aaaatgcata   6360
ttcctttttt aacttgccat ttatttactt ttagtggaaa ttgtgaccaa tttgttcatg   6420
tagaacggat ttggaccatt gcgtccacaa aacgtctctt ttgctcgatc ttcacaaagc   6480
gataccgaaa tccagagata gttttcaaaa gtcagaaatg gcaaagttat aaatagtaaa   6540
acagaataga tgctgtaatc gacttcaata acaagtggca tcacgtttct agttctagac   6600
ccatcagctg ggccggccca gctgatgatc ccggtgaagt tcctattccg aagttcctat   6660
tctccagaaa gtataggaac ttcactagag cttgcggccg cgcatgctga cttaatcagc   6720
taacgccact cgaggggggg cccggtaccg gcgcgccgtt ctatagtgtc acctaaatcg   6780
tatgtgtatg atacataagg ttatgtatta attgtagccg cgttctaacg acaatatgtc   6840
catatggtgc actctcagta caatctgctc tgatgccgca tagttaagcc agccccgaca   6900
cccgccaaca cccgctgacg cgccctgacg ggcttgtctg ctcccggcat ccgcttacag   6960
acaagctgtg accgtctccg ggagctgcat gtgtcagagg ttttcaccgt catcaccgaa   7020
acgcgcgaga cgaaagggcc tcgtgatacg cctattttta taggttaatg tcatgaccaa   7080
aatcccttaa cgtgagtttt cgttccactg agcgtcagac cccgtagaaa agatcaaagg   7140
atcttcttga gatccttttt ttctgcgcgt aatctgctgc ttgcaaacaa aaaaaccacc   7200
gctaccagcg gtggtttgtt tgccggatca agagctacca actctttttc cgaaggtaac   7260
```

```
tggcttcagc agagcgcaga taccaaatac tgtccttcta gtgtagccgt agttaggcca   7320

ccacttcaag aactctgtag caccgcctac atacctcgct ctgctaatcc tgttaccagt   7380

ggctgctgcc agtggcgata agtcgtgtct taccgggttg gactcaagac gatagttacc   7440

ggataaggcg cagcggtcgg gctgaacggg gggttcgtgc acacagccca gcttggagcg   7500

aacgacctac accgaactga gatacctaca gcgtgagcat tgagaaagcg ccacgcttcc   7560

cgaagggaga aaggcggaca ggtatccggt aagcggcagg gtcggaacag gagagcgcac   7620

gagggagctt ccagggggaa acgcctggta tctttatagt cctgtcgggt ttcgccacct   7680

ctgacttgag cgtcgatttt tgtgatgctc gtcagggggg cggagcctat ggaaaaacgc   7740

cagcaacgcg gcctttttac ggttcctggc cttttgctgg ccttttgctc acatgttctt   7800

tcctgcgtta tcccctgatt ctgtggataa ccgtattacc gcctttgagt gagctgatac   7860

cgctcgccgc agccgaacga ccgagcgcag cgagtcagtg agcgaggaag cggaagagcg   7920

cccaatacgc aaaccgcctc tccccgcgcg ttggccgatt cattaatgca ggttgatcag   7980

atctcgatcc cgcgaaatta atacgactca ctatagggag accacaacgg tttccctcta   8040

gaaataattt tgtttaactt taagaaggag atatacccat ggaaaagcct gaactcaccg   8100

cgacgtctgt cgagaagttt ctgatcgaaa agttcgacag cgtctccgac ctgatgcagc   8160

tctcggaggg cgaagaatct cgtgctttca gcttcgatgt aggagggcgt ggatatgtcc   8220

tgcgggtaaa tagctgcgcc gatggtttct acaaagatcg ttatgtttat cggcactttg   8280

catcggccgc gctcccgatt ccggaagtgc ttgacattgg ggaattcagc gagagcctga   8340

cctattgcat ctcccgccgt gcacagggtg tcacgttgca agacctgcct gaaaccgaac   8400

tgcccgctgt tctgcagccg gtcgcggagg ctatggatgc gatcgctgcg gccgatctta   8460

gccagacgag cgggttcggc ccattcggac cgcaaggaat cggtcaatac actacatggc   8520

gtgatttcat atgcgcgatt gctgatcccc atgtgtatca ctggcaaact gtgatggacg   8580

acaccgtcag tgcgtccgtc gcgcaggctc tcgatgagct gatgctttgg gccgaggact   8640

gccccgaagt ccggcacctc gtgcacgcgg atttcggctc caacaatgtc ctgacggaca   8700

atggccgcat aacagcggtc attgactgga gcgaggcgat gttcggggat tcccaatacg   8760

aggtcgccaa catcttcttc tggaggccgt ggttggcttg tatggagcag cagacgcgct   8820

acttcgagcg gaggcatccg gagcttgcag gatcgccgcg gctccgggcg tatatgctcc   8880

gcattggtct tgaccaactc tatcagagct tggttgacgg caatttcgat gatgcagctt   8940

gggcgcaggg tcgatgcgac gcaatcgtcc gatccggagc cgggactgtc gggcgtacac   9000

aaatcgcccg cagaagcgcg gccgtctgga ccgatggctg tgtagaagta ctcgccgata   9060

gtggaaaccg acgccccagc actcgtccga gggcaaagga atagtgaggt acagcttgga   9120

tcgatccggc tgctaacaaa gcccgaaagg aagctgagtt ggctgctgcc accgctgagc   9180

aataactagc ataacccctt ggggcctcta aacgggtctt gaggggtttt ttgctgaaag   9240

gaggaactat atccggatgc tcgggcgcgc cggtacccgg gtaccgagct cactagacgc   9300

ggtgaaatta cctaattaac accggtgttt atcgaaccac tttgtacaag aaagctgggt   9360

ctagatatct cga                                                      9373
```

<210> SEQ ID NO 20
<211> LENGTH: 3887
<212> TYPE: DNA
<213> ORGANISM: Artificial sequence
<220> FEATURE:
<223> OTHER INFORMATION: Plasmid, QC642-1

<400> SEQUENCE: 20

```
tttcaatcat gtcttaggta tgaagcagat tataaatcat attggataaa aaatattcaa      60
atttattaat tcacgaagga gatttagtca cagttatatg gaactttgtt aattttgctc     120
ataattttaa cattaaactt ctttagaggg agggggttaa ttaaatgcaa gagtatcttt     180
tgtgttaatt gattttactc tccagtatac ttatactact attatatacg attatgcaat     240
ataattaatt tttaattaac agataaaaat tcatttaaga attatcaaac atcgtgtaaa     300
tagtttttct ttttcgcaag tatactttat aggaagtaac tctatttttc ttaaaataac     360
ataaaaagaa aagaaactca ttttataaga taataagatg ctaaatgtga gtagctttag     420
acatccacga aatttgaacc ttgattctct atttcacagt aaattagtct attaaattca     480
acactattaa tatgtgagag gatttaaatc tttctctatt ttattttcat tttttaaatg     540
gaatattatt ttgcatttaa aatgaaaaat atatatggtg gatttgagtg tgtgcacaca     600
tgtatctttc ttaagttgac aggtagcata gttttaaata agtttttgtc ttttataaca     660
aataattttc cgtctacaca actattatat tcaacaaaaa ataaaattaa cacagttcca     720
catataaacg ttaaaaattt aactaaagaa agaaaatcat aaacgttacg ttacattcct     780
attggaattg atatgataag cctagcccaa gagaaaaggg aaaatttcca aaatttaaag     840
ggaagaagat aagaagacgc tgatgttaga gaatttcaag cagactttga atgtgtcact     900
gtgtttgtgt ctttgatccg aagtttctca ctgaacctca acatgtctac acattacatc     960
gccagcaaac ccctcaagct ctacatgcac gacacgtgtc tctacattct cttcacactc    1020
ccttcataaa taaaccaccc tttcttccat cctcatccct caaacacagc aagggcgaat    1080
tcgacccagc tttcttgtac aaagttggca ttataaaaaa taattgctca tcaatttgtt    1140
gcaacgaaca ggtcactatc agtcaaaata aaatcattat ttgccatcca gctgatatcc    1200
cctatagtga gtcgtattac atggtcatag ctgtttcctg gcagctctgg cccgtgtctc    1260
aaaatctctg atgttacatt gcacaagata aaaatatatc atcatgcctc ctctagacca    1320
gccaggacag aaatgcctcg acttcgctgc tgcccaaggt tgccgggtga cgcacaccgt    1380
ggaaacggat gaaggcacga acccagtgga cataagcctg ttcggttcgt aagctgtaat    1440
gcaagtagcg tatgcgctca cgcaactggt ccagaacctt gaccgaacgc agcggtggta    1500
acggcgcagt ggcggttttc atggcttgtt atgactgttt ttttggggta cagtctatgc    1560
ctcgggcatc caagcagcaa gcgcgttacg ccgtgggtcg atgtttgatg ttatggagca    1620
gcaacgatgt tacgcagcag ggcagtcgcc ctaaaacaaa gttaaacatc atgagggaag    1680
cggtgatcgc cgaagtatcg actcaactat cagaggtagt tggcgtcatc gagcgccatc    1740
tcgaaccgac gttgctggcc gtacatttgt acggctccgc agtggatggc ggcctgaagc    1800
cacacagtga tattgatttg ctggttacgg tgaccgtaag gcttgatgaa acaacgcggc    1860
gagctttgat caacgacctt ttggaaactt cggcttcccc tggagagagc gagattctcc    1920
gcgctgtaga agtcaccatt gttgtgcacg acgacatcat tccgtggcgt tatccagcta    1980
agcgcgaact gcaatttgga gaatggcagc gcaatgacat tcttgcaggt atcttcgagc    2040
cagccacgat cgacattgat ctggctatct tgctgacaaa agcaagagaa catagcgttg    2100
ccttggtagg tccagcggcg gaggaactct ttgatccggt tcctgaacag gatctatttg    2160
aggcgctaaa tgaaacctta acgctatgga actcgccgcc cgactgggct ggcgatgagc    2220
gaaatgtagt gcttacgttg tcccgcattt ggtacagcgc agtaaccggc aaaatcgcgc    2280
```

```
cgaaggatgt cgctgccgac tgggcaatgg agcgcctgcc ggcccagtat cagcccgtca   2340

tacttgaagc tagacaggct tatcttggac aagaagaaga tcgcttggcc tcgcgcgcag   2400

atcagttgga agaatttgtc cactacgtga aaggcgagat caccaaggta gtcggcaaat   2460

aaccctcgag ccacccatga ccaaaatccc ttaacgtgag ttacgcgtcg ttccactgag   2520

cgtcagaccc cgtagaaaag atcaaaggat cttcttgaga tccttttttt ctgcgcgtaa   2580

tctgctgctt gcaaacaaaa aaaccaccgc taccagcggt ggtttgtttg ccggatcaag   2640

agctaccaac tctttttccg aaggtaactg gcttcagcag agcgcagata ccaaatactg   2700

tccttctagt gtagccgtag ttaggccacc acttcaagaa ctctgtagca ccgcctacat   2760

acctcgctct gctaatcctg ttaccagtgg ctgctgccag tggcgataag tcgtgtctta   2820

ccgggttgga ctcaagacga tagttaccgg ataaggcgca gcggtcgggc tgaacggggg   2880

gttcgtgcac acagcccagc ttggagcgaa cgacctacac cgaactgaga tacctacagc   2940

gtgagcattg agaaagcgcc acgcttcccg aagggagaaa ggcggacagg tatccggtaa   3000

gcggcagggt cggaacagga gagcgcacga gggagcttcc agggggaaac gcctggtatc   3060

tttatagtcc tgtcgggttt cgccacctct gacttgagcg tcgatttttg tgatgctcgt   3120

caggggggcg gagcctatgg aaaaacgcca gcaacgcggc ctttttacgg ttcctggcct   3180

tttgctggcc ttttgctcac atgttctttc ctgcgttatc ccctgattct gtggataacc   3240

gtattaccgc ctttgagtga gctgataccg ctcgccgcag ccgaacgacc gagcgcagcg   3300

agtcagtgag cgaggaagcg gaagagcgcc caatacgcaa accgcctctc cccgcgcgtt   3360

ggccgattca ttaatgcagc tggcacgaca ggtttcccga ctggaaagcg ggcagtgagc   3420

gcaacgcaat taatacgcgt accgctagcc aggaagagtt tgtagaaacg caaaaaggcc   3480

atccgtcagg atggccttct gcttagtttg atgcctggca gtttatggcg ggcgtcctgc   3540

ccgccaccct ccgggccgtt gcttcacaac gttcaaatcc gctcccggcg gatttgtcct   3600

actcaggaga gcgttcaccg acaaacaaca gataaaacga aaggcccagt cttccgactg   3660

agcctttcgt tttatttgat gcctggcagt tccctactct cgcgttaacg ctagcatgga   3720

tgttttccca gtcacgacgt tgtaaaacga cggccagtct taagctcggg ccccaaataa   3780

tgattttatt ttgactgata gtgacctgtt cgttgcaaca aattgatgag caatgctttt   3840

ttataatgcc aactttgtac aaaaaagcag gctccgaatt cgcccctt                 3887
```

<210> SEQ ID NO 21
<211> LENGTH: 5286
<212> TYPE: DNA
<213> ORGANISM: Artificial sequence
<220> FEATURE:
<223> OTHER INFORMATION: Plasmid, QC330

<400> SEQUENCE: 21

```
atcaacaagt ttgtacaaaa aagctgaacg agaaacgtaa aatgatataa atatcaatat     60

attaaattag attttgcata aaaaacagac tacataatac tgtaaaacac aacatatcca    120

gtcatattgg cggccgcatt aggcacccca ggctttacac tttatgcttc cggctcgtat    180

aatgtgtgga ttttgagtta ggatccgtcg agattttcag gagctaagga agctaaaatg    240

gagaaaaaaa tcactggata taccaccgtt gatatatccc aatggcatcg taaagaacat    300

tttgaggcat ttcagtcagt tgctcaatgt acctataacc agaccgttca gctggatatt    360

acggcctttt taaagaccgt aaagaaaaat aagcacaagt tttatccggc ctttattcac    420

attcttgccc gcctgatgaa tgctcatccg gaattccgta tggcaatgaa agacggtgag    480
```

```
ctggtgatat gggatagtgt tcacccttgt tacaccgttt tccatgagca aactgaaacg    540
ttttcatcgc tctggagtga ataccacgac gatttccggc agtttctaca catatattcg    600
caagatgtgg cgtgttacgg tgaaaacctg gcctatttcc ctaaagggtt tattgagaat    660
atgtttttcg tctcagccaa tccctgggtg agtttcacca gttttgattt aaacgtggcc    720
aatatggaca acttcttcgc ccccgttttc accatgggca aatattatac gcaaggcgac    780
aaggtgctga tgccgctggc gattcaggtt catcatgccg tttgtgatgg cttccatgtc    840
ggcagaatgc ttaatgaatt acaacagtac tgcgatgagt ggcagggcgg ggcgtaaaga    900
tctggatccg gcttactaaa agccagataa cagtatgcgt atttgcgcgc tgatttttgc    960
ggtataagaa tatatactga tatgtatacc cgaagtatgt caaaaagagg tatgctatga   1020
agcagcgtat tacagtgaca gttgacagcg acagctatca gttgctcaag gcatatatga   1080
tgtcaatatc tccggtctgg taagcacaac catgcagaat gaagcccgtc gtctgcgtgc   1140
cgaacgctgg aaagcggaaa atcaggaagg gatggctgag gtcgcccggt ttattgaaat   1200
gaacggctct tttgctgacg agaacagggg ctggtgaaat gcagtttaag gtttacacct   1260
ataaaagaga gagccgttat cgtctgtttg tggatgtaca gagtgatatt attgacacgc   1320
ccgggcgacg gatggtgatc cccctggcca gtgcacgtct gctgtcagat aaagtctccc   1380
gtgaacttta cccggtggtg catatcgggg atgaaagctg gcgcatgatg accaccgata   1440
tggccagtgt gccggtctcc gttatcgggg aagaagtggc tgatctcagc caccgcgaaa   1500
atgacatcaa aaacgccatt aacctgatgt tctggggaat ataaatgtca ggctccctta   1560
tacacagcca gtctgcaggt cgaccatagt gactggatat gttgtgtttt acagtattat   1620
gtagtctgtt ttttatgcaa aatctaattt aatatattga tatttatatc attttacgtt   1680
tctcgttcag ctttcttgta caaagtggtt gatgggatcc atggcccaca gcaagcacgg   1740
cctgaaggag gagatgacca tgaagtacca catggagggc tgcgtgaacg gccacaagtt   1800
cgtgatcacc ggcgagggca tcggctaccc cttcaagggc aagcagacca tcaacctgtg   1860
cgtgatcgag ggcggccccc tgcccttcag cgaggacatc ctgagcgccg gcttcaagta   1920
cggcgaccgg atcttcaccg agtacccccca ggacatcgtg gactacttca agaacagctg   1980
ccccgccggc tacacctggg gccggagctt cctgttcgag gacggcgccg tgtgcatctg   2040
taacgtggac atcaccgtga gcgtgaagga gaactgcatc taccacaaga gcatcttcaa   2100
cggcgtgaac ttccccgccg acggccccgt gatgaagaag atgaccacca actgggaggc   2160
cagctgcgag aagatcatgc ccgtgcctaa gcagggcatc ctgaagggcg acgtgagcat   2220
gtacctgctg ctgaaggacg gcggccggta ccggtgccag ttcgacaccg tgtacaaggc   2280
caagagcgtg cccagcaaga tgcccgagtg gcacttcatc cagcacaagc tgctgcggga   2340
ggaccggagc gacgccaaga accagaagtg gcagctgacc gagcacgcca tcgccttccc   2400
cagcgccctg gcctgagagc tcgaatttcc ccgatcgttc aaacatttgg caataaagtt   2460
tcttaagatt gaatcctgtt gccggtcttg cgatgattat catataattt ctgttgaatt   2520
acgttaagca tgtaataatt aacatgtaat gcatgacgtt atttatgaga tgggttttta   2580
tgattagagt cccgcaatta tacatttaat acgcgataga aaacaaaata tagcgcgcaa   2640
actaggataa attatcgcgc gcggtgtcat ctatgttact agatcgggaa ttctagtggc   2700
cggcccagct gatatccatc acactggcgg ccgctcgagt tctatagtgt cacctaaatc   2760
gtatgtgtat gatacataag gttatgtatt aattgtagcc gcgttctaac gacaatatgt   2820
```

```
ccatatggtg cactctcagt acaatctgct ctgatgccgc atagttaagc cagccccgac   2880
acccgccaac acccgctgac gcgccctgac gggcttgtct gctcccggca tccgcttaca   2940
gacaagctgt gaccgtctcc gggagctgca tgtgtcagag gttttcaccg tcatcaccga   3000
aacgcgcgag acgaaagggc ctcgtgatac gcctattttt ataggttaat gtcatgacca   3060
aaatccctta acgtgagttt tcgttccact gagcgtcaga ccccgtagaa aagatcaaag   3120
gatcttcttg agatcctttt tttctgcgcg taatctgctg cttgcaaaca aaaaaaccac   3180
cgctaccagc ggtggtttgt ttgccggatc aagagctacc aactcttttt ccgaaggtaa   3240
ctggcttcag cagagcgcag ataccaaata ctgtccttct agtgtagccg tagttaggcc   3300
accacttcaa gaactctgta gcaccgccta catacctcgc tctgctaatc ctgttaccag   3360
tggctgctgc cagtggcgat aagtcgtgtc ttaccgggtt ggactcaaga cgatagttac   3420
cggataaggc gcagcggtcg ggctgaacgg ggggttcgtg cacacagccc agcttggagc   3480
gaacgaccta caccgaactg agatacctac agcgtgagca ttgagaaagc gccacgcttc   3540
ccgaagggag aaaggcggac aggtatccgg taagcggcag ggtcggaaca ggagagcgca   3600
cgagggagct tccaggggga aacgcctggt atctttatag tcctgtcggg tttcgccacc   3660
tctgacttga gcgtcgattt ttgtgatgct cgtcaggggg gcggagccta tggaaaaacg   3720
ccagcaacgc ggccttttta cggttcctgg ccttttgctg gccttttgct cacatgttct   3780
ttcctgcgtt atcccctgat tctgtggata accgtattac cgcctttgag tgagctgata   3840
ccgctcgccg cagccgaacg accgagcgca gcgagtcagt gagcgaggaa gcggaagagc   3900
gcccaatacg caaaccgcct ctccccgcgc gttggccgat tcattaatgc aggttgatca   3960
gatctcgatc ccgcgaaatt aatacgactc actataggga gaccacaacg gtttccctct   4020
agaaataatt ttgtttaact ttaagaagga gatataccca tggaaaagcc tgaactcacc   4080
gcgacgtctg tcgagaagtt tctgatcgaa aagttcgaca gcgtctccga cctgatgcag   4140
ctctcggagg gcgaagaatc tcgtgctttc agcttcgatg taggagggcg tggatatgtc   4200
ctgcgggtaa atagctgcgc cgatggtttc tacaaagatc gttatgttta tcggcacttt   4260
gcatcggccg cgctcccgat tccggaagtg cttgacattg gggaattcag cgagagcctg   4320
acctattgca tctcccgccg tgcacagggt gtcacgttgc aagacctgcc tgaaaccgaa   4380
ctgcccgctg ttctgcagcc ggtcgcggag gctatggatg cgatcgctgc ggccgatctt   4440
agccagacga gcgggttcgg cccattcgga ccgcaaggaa tcggtcaata cactacatgg   4500
cgtgatttca tatgcgcgat tgctgatccc catgtgtatc actggcaaac tgtgatggac   4560
gacaccgtca gtgcgtccgt cgcgcaggct ctcgatgagc tgatgctttg ggccgaggac   4620
tgccccgaag tccggcacct cgtgcacgcg gatttcggct ccaacaatgt cctgacggac   4680
aatggccgca taacagcggt cattgactgg agcgaggcga tgttcgggga ttcccaatac   4740
gaggtcgcca acatcttctt ctggaggccg tggttggctt gtatggagca gcagacgcgc   4800
tacttcgagc ggaggcatcc ggagcttgca ggatcgccgc ggctccgggc gtatatgctc   4860
cgcattggtc ttgaccaact ctatcagagc ttggttgacg gcaatttcga tgatgcagct   4920
tgggcgcagg gtcgatgcga cgcaatcgtc cgatccggag ccgggactgt cgggcgtaca   4980
caaatcgccc gcagaagcgc ggccgtctgg accgatggct gtgtagaagt actcgccgat   5040
agtggaaacc gacgccccag cactcgtccg agggcaaagg aatagtgagg tacagcttgg   5100
atcgatccgg ctgctaacaa agcccgaaag gaagctgagt tggctgctgc caccgctgag   5160
caataactag cataacccct tggggcctct aaacgggtct tgaggggttt tttgctgaaa   5220
```

ggaggaacta tatccggatg atcgtcgagg cctcacgtgt taacaagctt gcatgcctgc 5280
aggttt 5286

<210> SEQ ID NO 22
<211> LENGTH: 4728
<212> TYPE: DNA
<213> ORGANISM: Artificial sequence
<220> FEATURE:
<223> OTHER INFORMATION: Plasmid, QC642-1Y

<400> SEQUENCE: 22
tttcaatcat gtcttaggta tgaagcagat tataaatcat attggataaa aaatattcaa 60
atttattaat tcacgaagga gatttagtca cagttatatg gaactttgtt aattttgctc 120
ataattttaa cattaaactt ctttagaggg agggggttaa ttaaatgcaa gagtatcttt 180
tgtgttaatt gattttactc tccagtatac ttatactact attatatacg attatgcaat 240
ataattaatt tttaattaac agataaaaat tcatttaaga attatcaaac atcgtgtaaa 300
tagtttttct ttttcgcaag tatactttat aggaagtaac tctatttttc ttaaaataac 360
ataaaaagaa aagaaactca ttttataaga taataagatg ctaaatgtga gtagctttag 420
acatccacga aatttgaacc ttgattctct atttcacagt aaattagtct attaaattca 480
acactattaa tatgtgagag gatttaaatc tttctctatt ttattttcat tttttaaatg 540
gaatattatt ttgcatttaa aatgaaaaat atatatggtg gatttgagtg tgtgcacaca 600
tgtatctttc ttaagttgac aggtagcata gttttaaata agtttttgtc ttttataaca 660
aataattttc cgtctacaca actattatat tcaacaaaaa ataaaattaa cacagttcca 720
catataaacg ttaaaaattt aactaaagaa agaaaatcat aaacgttacg ttacattcct 780
attggaattg atatgataag cctagcccaa gagaaaaggg aaaatttcca aaatttaaag 840
ggaagaagat aagaagacgc tgatgttaga gaatttcaag cagactttga atgtgtcact 900
gtgtttgtgt ctttgatccg aagtttctca ctgaacctca acatgtctac acattacatc 960
gccagcaaac ccctcaagct ctacatgcac gacacgtgtc tctacattct cttcacactc 1020
ccttcataaa taaaccaccc tttcttccat cctcatccct caaacacagc aagggcgaat 1080
tcgacccagc tttcttgtac aaagtggttg atgggatcca tggcccacag caagcacggc 1140
ctgaaggagg agatgaccat gaagtaccac atggagggct gcgtgaacgg ccacaagttc 1200
gtgatcaccg gcgagggcat cggctacccc ttcaagggca agcagaccat caacctgtgc 1260
gtgatcgagg gcggccccct gcccttcagc gaggacatcc tgagcgccgg cttcaagtac 1320
ggcgaccgga tcttcaccga gtacccccag gacatcgtgg actacttcaa gaacagctgc 1380
cccgccggct acacctgggg ccggagcttc ctgttcgagg acggcgccgt gtgcatctgt 1440
aacgtggaca tcaccgtgag cgtgaaggag aactgcatct accacaagag catcttcaac 1500
ggcgtgaact tccccgccga cggccccgtg atgaagaaga tgaccaccaa ctgggaggcc 1560
agctgcgaga agatcatgcc cgtgcctaag cagggcatcc tgaagggcga cgtgagcatg 1620
tacctgctgc tgaaggacgg cggccggtac cggtgccagt tcgacaccgt gtacaaggcc 1680
aagagcgtgc ccagcaagat gcccgagtgg cacttcatcc agcacaagct gctgcgggag 1740
gaccggagcg acgccaagaa ccagaagtgg cagctgaccg agcacgccat cgccttcccc 1800
agcgccctgg cctgagagct cgaatttccc cgatcgttca aacatttggc aataaagttt 1860
cttaagattg aatcctgttg ccggtcttgc gatgattatc atataatttc tgttgaatta 1920

```
cgttaagcat gtaataatta acatgtaatg catgacgtta tttatgagat gggtttttat   1980
gattagagtc ccgcaattat acatttaata cgcgatagaa aacaaaatat agcgcgcaaa   2040
ctaggataaa ttatcgcgcg cggtgtcatc tatgttacta gatcgggaat tctagtggcc   2100
ggcccagctg atatccatca cactggcggc cgctcgagtt ctatagtgtc acctaaatcg   2160
tatgtgtatg atacataagg ttatgtatta attgtagccg cgttctaacg acaatatgtc   2220
catatggtgc actctcagta caatctgctc tgatgccgca tagttaagcc agccccgaca   2280
cccgccaaca cccgctgacg cgccctgacg ggcttgtctg ctcccggcat ccgcttacag   2340
acaagctgtg accgtctccg ggagctgcat gtgtcagagg ttttcaccgt catcaccgaa   2400
acgcgcgaga cgaaagggcc tcgtgatacg cctattttta taggttaatg tcatgaccaa   2460
aatcccttaa cgtgagtttt cgttccactg agcgtcagac cccgtagaaa agatcaaagg   2520
atcttcttga gatccttttt ttctgcgcgt aatctgctgc ttgcaaacaa aaaaaccacc   2580
gctaccagcg gtggtttgtt tgccggatca agagctacca actctttttc cgaaggtaac   2640
tggcttcagc agagcgcaga taccaaatac tgtccttcta gtgtagccgt agttaggcca   2700
ccacttcaag aactctgtag caccgcctac atacctcgct ctgctaatcc tgttaccagt   2760
ggctgctgcc agtggcgata agtcgtgtct taccgggttg gactcaagac gatagttacc   2820
ggataaggcg cagcggtcgg gctgaacggg gggttcgtgc acacagccca gcttggagcg   2880
aacgacctac accgaactga gatacctaca gcgtgagcat tgagaaagcg ccacgcttcc   2940
cgaagggaga aaggcggaca ggtatccggt aagcggcagg gtcggaacag gagagcgcac   3000
gagggagctt ccagggggaa acgcctggta tctttatagt cctgtcgggt ttcgccacct   3060
ctgacttgag cgtcgatttt tgtgatgctc gtcagggggg cggagcctat ggaaaaacgc   3120
cagcaacgcg gcctttttac ggttcctggc cttttgctgg ccttttgctc acatgttctt   3180
tcctgcgtta tcccctgatt ctgtggataa ccgtattacc gcctttgagt gagctgatac   3240
cgctcgccgc agccgaacga ccgagcgcag cgagtcagtg agcgaggaag cggaagagcg   3300
cccaatacgc aaaccgcctc tccccgcgcg ttggccgatt cattaatgca ggttgatcag   3360
atctcgatcc cgcgaaatta atacgactca ctatagggag accacaacgg tttccctcta   3420
gaaataattt tgtttaactt taagaaggag atatacccat ggaaaagcct gaactcaccg   3480
cgacgtctgt cgagaagttt ctgatcgaaa agttcgacag cgtctccgac ctgatgcagc   3540
tctcggaggg cgaagaatct cgtgctttca gcttcgatgt aggagggcgt ggatatgtcc   3600
tgcgggtaaa tagctgcgcc gatggtttct acaaagatcg ttatgtttat cggcactttg   3660
catcggccgc gctcccgatt ccggaagtgc ttgacattgg ggaattcagc gagagcctga   3720
cctattgcat ctcccgccgt gcacagggtg tcacgttgca agacctgcct gaaaccgaac   3780
tgcccgctgt tctgcagccg gtcgcggagg ctatggatgc gatcgctgcg gccgatctta   3840
gccagacgag cgggttcggc ccattcggac cgcaaggaat cggtcaatac actacatggc   3900
gtgatttcat atgcgcgatt gctgatcccc atgtgtatca ctggcaaact gtgatggacg   3960
acaccgtcag tgcgtccgtc gcgcaggctc tcgatgagct gatgctttgg gccgaggact   4020
gccccgaagt ccggcacctc gtgcacgcgg atttcggctc caacaatgtc ctgacggaca   4080
atggccgcat aacagcggtc attgactgga gcgaggcgat gttcggggat tcccaatacg   4140
aggtcgccaa catcttcttc tggaggccgt ggttggcttg tatggagcag cagacgcgct   4200
acttcgagcg gaggcatccg gagcttgcag gatcgccgcg gctccgggcg tatatgctcc   4260
gcattggtct tgaccaactc tatcagagct tggttgacgg caatttcgat gatgcagctt   4320
```

```
gggcgcaggg tcgatgcgac gcaatcgtcc gatccggagc cgggactgtc gggcgtacac   4380
aaatcgcccg cagaagcgcg gccgtctgga ccgatggctg tgtagaagta ctcgccgata   4440
gtggaaaccg acgccccagc actcgtccga gggcaaagga atagtgaggt acagcttgga   4500
tcgatccggc tgctaacaaa gcccgaaagg aagctgagtt ggctgctgcc accgctgagc   4560
aataactagc ataacccctt ggggcctcta aacgggtctt gaggggtttt ttgctgaaag   4620
gaggaactat atccggatga tcgtcgaggc ctcacgtgtt aacaagcttg catgcctgca   4680
ggtttatcaa caagtttgta caaaaaagca ggctccgaat tcgccctt                4728
```

```
<210> SEQ ID NO 23
<211> LENGTH: 4157
<212> TYPE: DNA
<213> ORGANISM: Artificial sequence
<220> FEATURE:
<223> OTHER INFORMATION: Plasmid, pZSL90

<400> SEQUENCE: 23

agatccgtca acatggtgga gcacgacact ctcgtctact ccaagaatat caaagataca     60
gtctcagaag accaaagggc tattgagact tttcaacaaa gggtaatatc gggaaacctc    120
ctcggattcc attgcccagc tatctgtcac ttcatcaaaa ggacagtaga aaaggaaggt    180
ggcacctaca aatgccatca ttgcgataaa ggaaaggcta tcgttcaaga tgcctctgcc    240
gacagtggtc ccaaagatgg acccccaccc acgaggagca tcgtggaaaa agaagacgtt    300
ccaaccacgt cttcaaagca agtggattga tgtgatgatc ctatgcgtat ggtatgacgt    360
gtgttcaaga tgatgacttc aaacctacct atgacgtatg gtatgacgtg tgtcgactga    420
tgacttagat ccactcgagc ggctataaat acgtacctac gcaccctgcg ctaccatccc    480
tagagctgca gcttattttt acaacaatta ccaacaacaa caaacaacaa acaacattac    540
aattactatt tacaattaca gtcgacccgg gatccatggc ccacagcaag cacggcctga    600
aggaggagat gaccatgaag taccacatgg agggctgcgt gaacggccac aagttcgtga    660
tcaccggcga gggcatcggc taccccttca agggcaagca gaccatcaac ctgtgcgtga    720
tcgagggcgg cccccctgccc ttcagcgagg acatcctgag cgccggcttc aagtacggcg    780
accggatctt caccgagtac ccccaggaca tcgtggacta cttcaagaac agctgccccg    840
ccggctacac ctggggccgg agcttcctgt tcgaggacgg cgccgtgtgc atctgtaacg    900
tggacatcac cgtgagcgtg aaggagaact gcatctacca caagagcatc ttcaacggcg    960
tgaacttccc cgccgacggc cccgtgatga agaagatgac caccaactgg gaggccagct   1020
gcgagaagat catgcccgtg cctaagcagg gcatcctgaa gggcgacgtg agcatgtacc   1080
tgctgctgaa ggacggcggc cggtaccggt gccagttcga caccgtgtac aaggccaaga   1140
gcgtgcccag caagatgccc gagtggcact tcatccagca caagctgctg cgggaggacc   1200
ggagcgacgc caagaaccag aagtggcagc tgaccgagca cgccatcgcc ttccccagcg   1260
ccctggcctg agagctcgaa tttccccgat cgttcaaaca tttggcaata aagtttctta   1320
agattgaatc ctgttgccgg tcttgcgatg attatcatat aatttctgtt gaattacgtt   1380
aagcatgtaa taattaacat gtaatgcatg acgttattta tgagatgggt ttttatgatt   1440
agagtcccgc aattatacat ttaatacgcg atagaaaaca aaatatagcg cgcaaactag   1500
gataaattat cgcgcgcggt gtcatctatg ttactagatc gggaattcta gtggccggcc   1560
cagctgatat ccatcacact ggcggccgct cgagttctat agtgtcacct aaatcgtatg   1620
```

-continued

```
tgtatgatac ataaggttat gtattaattg tagccgcgtt ctaacgacaa tatgtccata   1680
tggtgcactc tcagtacaat ctgctctgat gccgcatagt taagccagcc ccgacacccg   1740
ccaacacccg ctgacgcgcc ctgacgggct tgtctgctcc cggcatccgc ttacagacaa   1800
gctgtgaccg tctccgggag ctgcatgtgt cagaggtttt caccgtcatc accgaaacgc   1860
gcgagacgaa agggcctcgt gatacgccta tttttatagg ttaatgtcat gaccaaaatc   1920
ccttaacgtg agttttcgtt ccactgagcg tcagaccccg tagaaaagat caaaggatct   1980
tcttgagatc ctttttttct gcgcgtaatc tgctgcttgc aaacaaaaaa accaccgcta   2040
ccagcggtgg tttgtttgcc ggatcaagag ctaccaactc tttttccgaa ggtaactggc   2100
ttcagcagag cgcagatacc aaatactgtc cttctagtgt agccgtagtt aggccaccac   2160
ttcaagaact ctgtagcacc gcctacatac ctcgctctgc taatcctgtt accagtggct   2220
gctgccagtg gcgataagtc gtgtcttacc gggttggact caagacgata gttaccggat   2280
aaggcgcagc ggtcgggctg aacggggggt tcgtgcacac agcccagctt ggagcgaacg   2340
acctacaccg aactgagata cctacagcgt gagcattgag aaagcgccac gcttcccgaa   2400
gggagaaagg cggacaggta tccggtaagc ggcagggtcg gaacaggaga gcgcacgagg   2460
gagcttccag ggggaaacgc ctggtatctt tatagtcctg tcgggtttcg ccacctctga   2520
cttgagcgtc gatttttgtg atgctcgtca ggggggcgga gcctatggaa aaacgccagc   2580
aacgcggcct ttttacggtt cctggccttt tgctggcctt ttgctcacat gttctttcct   2640
gcgttatccc ctgattctgt ggataaccgt attaccgcct ttgagtgagc tgataccgct   2700
cgccgcagcc gaacgaccga gcgcagcgag tcagtgagcg aggaagcgga agagcgccca   2760
atacgcaaac cgcctctccc cgcgcgttgg ccgattcatt aatgcaggtt gatcagatct   2820
cgatcccgcg aaattaatac gactcactat agggagacca caacggtttc cctctagaaa   2880
taattttgtt taactttaag aaggagatat acccatggaa aagcctgaac tcaccgcgac   2940
gtctgtcgag aagtttctga tcgaaaagtt cgacagcgtc tccgacctga tgcagctctc   3000
ggagggcgaa gaatctcgtg ctttcagctt cgatgtagga gggcgtggat atgtcctgcg   3060
ggtaaatagc tgcgccgatg gtttctacaa agatcgttat gtttatcggc actttgcatc   3120
ggccgcgctc ccgattccgg aagtgcttga cattggggaa ttcagcgaga gcctgaccta   3180
ttgcatctcc cgccgtgcac agggtgtcac gttgcaagac ctgcctgaaa ccgaactgcc   3240
cgctgttctg cagccggtcg cggaggctat ggatgcgatc gctgcggccg atcttagcca   3300
gacgagcggg ttcggcccat tcggaccgca aggaatcggt caatacacta catggcgtga   3360
tttcatatgc gcgattgctg atccccatgt gtatcactgg caaactgtga tggacgacac   3420
cgtcagtgcg tccgtcgcgc aggctctcga tgagctgatg ctttgggccg aggactgccc   3480
cgaagtccgg cacctcgtgc acgcggattt cggctccaac aatgtcctga cggacaatgg   3540
ccgcataaca gcggtcattg actggagcga ggcgatgttc ggggattccc aatacgaggt   3600
cgccaacatc ttcttctgga ggccgtggtt ggcttgtatg gagcagcaga cgcgctactt   3660
cgagcggagg catccggagc ttgcaggatc gccgcggctc cgggcgtata tgctccgcat   3720
tggtcttgac caactctatc agagcttggt tgacggcaat ttcgatgatg cagcttgggc   3780
gcagggtcga tgcgacgcaa tcgtccgatc cggagccggg actgtcgggc gtacacaaat   3840
cgcccgcaga agcgcggccg tctggaccga tggctgtgta gaagtactcg ccgatagtgg   3900
aaaccgacgc cccagcactc gtccgagggc aaaggaatag tgaggtacag cttggatcga   3960
tccggctgct aacaaagccc gaaaggaagc tgagttggct gctgccaccg ctgagcaata   4020
```

actagcataa ccccttgggg cctctaaacg ggtcttgagg ggttttttgc tgaaaggagg 4080
aactatatcc ggatgatcgt cgaggcctca cgtgttaaca agcttgcatg cctgcaggtt 4140
taaacagtcg actctag 4157

<210> SEQ ID NO 24
<211> LENGTH: 3640
<212> TYPE: DNA
<213> ORGANISM: Artificial sequence
<220> FEATURE:
<223> OTHER INFORMATION: Plasmid, QC330-Y

<400> SEQUENCE: 24
ttgtacaaag tggttgatgg gatccatggc ccacagcaag cacggcctga aggaggagat 60
gaccatgaag taccacatgg agggctgcgt gaacggccac aagttcgtga tcaccggcga 120
gggcatcggc taccccttca agggcaagca gaccatcaac ctgtgcgtga tcgagggcgg 180
ccccctgccc ttcagcgagg acatcctgag cgccggcttc aagtacggcg accggatctt 240
caccgagtac ccccaggaca tcgtggacta cttcaagaac agctgccccg ccggctacac 300
ctggggccgg agcttcctgt tcgaggacgg cgccgtgtgc atctgtaacg tggacatcac 360
cgtgagcgtg aaggagaact gcatctacca caagagcatc ttcaacggcg tgaacttccc 420
cgccgacggc cccgtgatga agaagatgac caccaactgg gaggccagct gcgagaagat 480
catgcccgtg cctaagcagg gcatcctgaa gggcgacgtg agcatgtacc tgctgctgaa 540
ggacggcggc cggtaccggt gccagttcga caccgtgtac aaggccaaga gcgtgcccag 600
caagatgccc gagtggcact tcatccagca caagctgctg cgggaggacc ggagcgacgc 660
caagaaccag aagtggcagc tgaccgagca cgccatcgcc ttccccagcg ccctggcctg 720
agagctcgaa tttccccgat cgttcaaaca tttggcaata aagtttctta agattgaatc 780
ctgttgccgg tcttgcgatg attatcatat aatttctgtt gaattacgtt aagcatgtaa 840
taattaacat gtaatgcatg acgttattta tgagatgggt ttttatgatt agagtcccgc 900
aattatacat ttaatacgcg atagaaaaca aaatatagcg cgcaaactag gataaattat 960
cgcgcgcggt gtcatctatg ttactagatc gggaattcta gtggccggcc cagctgatat 1020
ccatcacact ggcggccgct cgagttctat agtgtcacct aaatcgtatg tgtatgatac 1080
ataaggttat gtattaattg tagccgcgtt ctaacgacaa tatgtccata tggtgcactc 1140
tcagtacaat ctgctctgat gccgcatagt taagccagcc ccgacacccg ccaacacccg 1200
ctgacgcgcc ctgacgggct tgtctgctcc cggcatccgc ttacagacaa gctgtgaccg 1260
tctccgggag ctgcatgtgt cagaggtttt caccgtcatc accgaaacgc gcgagacgaa 1320
agggcctcgt gatacgccta tttttatagg ttaatgtcat gaccaaaatc ccttaacgtg 1380
agttttcgtt ccactgagcg tcagaccccg tagaaaagat caaaggatct tcttgagatc 1440 cttttttttct gcgcgtaatc tgctgcttgc aaacaaaaaa accaccgcta ccagcggtgg 1500
tttgtttgcc ggatcaagag ctaccaactc tttttccgaa ggtaactggc ttcagcagag 1560
cgcagatacc aaatactgtc cttctagtgt agccgtagtt aggccaccac ttcaagaact 1620
ctgtagcacc gcctacatac ctcgctctgc taatcctgtt accagtggct gctgccagtg 1680
gcgataagtc gtgtcttacc gggttggact caagacgata gttaccggat aaggcgcagc 1740
ggtcgggctg aacggggggt tcgtgcacac agcccagctt ggagcgaacg acctacaccg 1800
aactgagata cctacagcgt gagcattgag aaagcgccac gcttcccgaa gggagaaagg 1860

```
cggacaggta tccggtaagc ggcagggtcg gaacaggaga gcgcacgagg gagcttccag   1920

ggggaaacgc ctggtatctt tatagtcctg tcgggtttcg ccacctctga cttgagcgtc   1980

gatttttgtg atgctcgtca ggggggcgga gcctatggaa aaacgccagc aacgcggcct   2040

ttttacggtt cctggccttt tgctggcctt ttgctcacat gttctttcct gcgttatccc   2100

ctgattctgt ggataaccgt attaccgcct ttgagtgagc tgataccgct cgccgcagcc   2160

gaacgaccga gcgcagcgag tcagtgagcg aggaagcgga agagcgccca atacgcaaac   2220

cgcctctccc cgcgcgttgg ccgattcatt aatgcaggtt gatcagatct cgatcccgcg   2280

aaattaatac gactcactat agggagacca caacggtttc cctctagaaa taattttgtt   2340

taactttaag aaggagatat acccatggaa aagcctgaac tcaccgcgac gtctgtcgag   2400

aagtttctga tcgaaaagtt cgacagcgtc tccgacctga tgcagctctc ggagggcgaa   2460

gaatctcgtg ctttcagctt cgatgtagga gggcgtggat atgtcctgcg ggtaaatagc   2520

tgcgccgatg gtttctacaa agatcgttat gtttatcggc actttgcatc ggccgcgctc   2580

ccgattccgg aagtgcttga cattggggaa ttcagcgaga gcctgaccta ttgcatctcc   2640

cgccgtgcac agggtgtcac gttgcaagac ctgcctgaaa ccgaactgcc cgctgttctg   2700

cagccggtcg cggaggctat ggatgcgatc gctgcggccg atcttagcca gacgagcggg   2760

ttcggcccat tcggaccgca aggaatcggt caatacacta catggcgtga tttcatatgc   2820

gcgattgctg atccccatgt gtatcactgg caaactgtga tggacgacac cgtcagtgcg   2880

tccgtcgcgc aggctctcga tgagctgatg ctttgggccg aggactgccc cgaagtccgg   2940

cacctcgtgc acgcggattt cggctccaac aatgtcctga cggacaatgg ccgcataaca   3000

gcggtcattg actggagcga ggcgatgttc ggggattccc aatacgaggt cgccaacatc   3060

ttcttctgga ggccgtggtt ggcttgtatg gagcagcaga cgcgctactt cgagcggagg   3120

catccggagc ttgcaggatc gccgcggctc cgggcgtata tgctccgcat tggtcttgac   3180

caactctatc agagcttggt tgacggcaat ttcgatgatg cagcttgggc gcagggtcga   3240

tgcgacgcaa tcgtccgatc cggagccggg actgtcgggc gtacacaaat cgcccgcaga   3300

agcgcggccg tctggaccga tggctgtgta gaagtactcg ccgatagtgg aaaccgacgc   3360

cccagcactc gtccgagggc aaaggaatag tgaggtacag cttggatcga tccggctgct   3420

aacaaagccc gaaaggaagc tgagttggct gctgccaccg ctgagcaata actagcataa   3480

ccccttgggg cctctaaacg ggtcttgagg ggttttttgc tgaaaggagg aactatatcc   3540

ggatgatcgt cgaggcctca cgtgttaaca agcttgcatg cctgcaggtt tatcaacaag   3600

tttgtacaaa aaagcaggct ccgaattcga cccagctttc                         3640
```

<210> SEQ ID NO 25
<211> LENGTH: 22
<212> TYPE: DNA
<213> ORGANISM: Artificial sequence
<220> FEATURE:
<223> OTHER INFORMATION: SAMS forward primer SAMS-76F

<400> SEQUENCE: 25

```
aggcttgttg tgcagttttt ga                                              22
```

<210> SEQ ID NO 26
<211> LENGTH: 22
<212> TYPE: DNA
<213> ORGANISM: Artificial sequence
<220> FEATURE:
<223> OTHER INFORMATION: FAM labeled ALS probe ALS-100T

<400> SEQUENCE: 26
ccacacaaca caatggcggc ca 22

<210> SEQ ID NO 27
<211> LENGTH: 22
<212> TYPE: DNA
<213> ORGANISM: Artificial sequence
<220> FEATURE:
<223> OTHER INFORMATION: ALS reverse primer ALS-163R

<400> SEQUENCE: 27
ggaagaagag aatcgggtgg tt 22

<210> SEQ ID NO 28
<211> LENGTH: 24
<212> TYPE: DNA
<213> ORGANISM: Artificial sequence
<220> FEATURE:
<223> OTHER INFORMATION: GFP forward primer GFP-24F

<400> SEQUENCE: 28
gaccaaggag atgaccatga agta 24

<210> SEQ ID NO 29
<211> LENGTH: 14
<212> TYPE: DNA
<213> ORGANISM: Artificial sequence
<220> FEATURE:
<223> OTHER INFORMATION: FAM labeled GFP probe GFP-51T

<400> SEQUENCE: 29
catggagggc tgcg 14

<210> SEQ ID NO 30
<211> LENGTH: 20
<212> TYPE: DNA
<213> ORGANISM: Artificial sequence
<220> FEATURE:
<223> OTHER INFORMATION: GFP reverse primer GFP-92R

<400> SEQUENCE: 30
ccggtgatca cgaacttgtg 20

<210> SEQ ID NO 31
<211> LENGTH: 24
<212> TYPE: DNA
<213> ORGANISM: Artificial sequence
<220> FEATURE:
<223> OTHER INFORMATION: HSP forward primer HSP-F1

<400> SEQUENCE: 31
caaacttgac aaagccacaa ctct 24

<210> SEQ ID NO 32
<211> LENGTH: 20
<212> TYPE: DNA
<213> ORGANISM: Artificial sequence
<220> FEATURE:
<223> OTHER INFORMATION: VIC labeled HSP probe HSP probe

<400> SEQUENCE: 32
ctctcatctc atataaatac 20

<210> SEQ ID NO 33

```
<211> LENGTH: 21
<212> TYPE: DNA
<213> ORGANISM: Artificial sequence
<220> FEATURE:
<223> OTHER INFORMATION: HSP reverse primer HSP-R1

<400> SEQUENCE: 33

ggagaaattg gtgtcgtgga a                                                21


<210> SEQ ID NO 34
<211> LENGTH: 100
<212> TYPE: DNA
<213> ORGANISM: Artificial sequence
<220> FEATURE:
<223> OTHER INFORMATION: ATTL1

<400> SEQUENCE: 34

caaataatga ttttattttg actgatagtg acctgttcgt tgcaacaaat tgataagcaa      60

tgctttttta taatgccaac tttgtacaaa aaagcaggct                           100


<210> SEQ ID NO 35
<211> LENGTH: 100
<212> TYPE: DNA
<213> ORGANISM: Artificial sequence
<220> FEATURE:
<223> OTHER INFORMATION: ATTL2

<400> SEQUENCE: 35

caaataatga ttttattttg actgatagtg acctgttcgt tgcaacaaat tgataagcaa      60

tgctttctta taatgccaac tttgtacaag aaagctgggt                           100


<210> SEQ ID NO 36
<211> LENGTH: 125
<212> TYPE: DNA
<213> ORGANISM: Artificial sequence
<220> FEATURE:
<223> OTHER INFORMATION: ATTR1

<400> SEQUENCE: 36

acaagtttgt acaaaaaagc tgaacgagaa acgtaaaatg atataaatat caatatatta      60

aattagattt tgcataaaaa acagactaca taatactgta aaacacaaca tatccagtca     120

ctatg                                                                 125


<210> SEQ ID NO 37
<211> LENGTH: 125
<212> TYPE: DNA
<213> ORGANISM: Artificial sequence
<220> FEATURE:
<223> OTHER INFORMATION: ATTR2

<400> SEQUENCE: 37

accactttgt acaagaaagc tgaacgagaa acgtaaaatg atataaatat caatatatta      60

aattagattt tgcataaaaa acagactaca taatactgta aaacacaaca tatccagtca     120

ctatg                                                                 125


<210> SEQ ID NO 38
<211> LENGTH: 21
<212> TYPE: DNA
<213> ORGANISM: Artificial sequence
<220> FEATURE:
<223> OTHER INFORMATION: ATTB1

<400> SEQUENCE: 38
```

```
caagtttgta caaaaaagca g                                              21


<210> SEQ ID NO 39
<211> LENGTH: 21
<212> TYPE: DNA
<213> ORGANISM: Artificial sequence
<220> FEATURE:
<223> OTHER INFORMATION: ATTB2

<400> SEQUENCE: 39

ccactttgta caagaaagct g                                              21


<210> SEQ ID NO 40
<211> LENGTH: 1593
<212> TYPE: DNA
<213> ORGANISM: Glycine max

<400> SEQUENCE: 40

atccctcaaa cacagtcatg ggaaacaaaa ctaccctttt gcttttgctc tttgttcttt      60

gccatggagt ggccacaaca acaatggcct tccatgatga tgagggtggt gataaaaagt     120

caccaaaaag tttgtttttg atgagcaact ccacgagggt tttcaagact gatgcagggg     180

aaatgcgtgt gctgaaaagc catggtggta ggatatttta taggcacatg cacattggct     240

tcatctctat ggaaccaaag tccttgtttg ttcctcagta cctcgactcc aatctcatca     300

tattcatccg tagaggggaa gcaaagctgg gattcatata tgatgatgaa ctagcggaaa     360

ggagattgaa gacaggggac ttgtacatga ttccatctgg ttcagcattc tatttggtga     420

acataggaga aggtcagaga cttcacgtta tctgcagcat tgacccctct acaagcttgg     480

gattagagac cttccagtcc ttctatattg ggggaggagc caattcgcac tcggtgcttt     540

ctggattcga acctgccatc cttgaaactg catttaatga atcaagaacg gtggtagagg     600

aaatcttctc caaggaacta gatgggccaa ttatgttcgt ggatgattct catgcaccta     660

gcttatggac taaattcctt caactgaaga aggatgacaa agagcaacag ctgaagaaaa     720

tgatgcaaga ccaagaggag gatgaggagg agaagcaaac aagtaggtca tggaggaagc     780

tcttggaaac cgtatttggg aaggtgaatg agaagataga gaacaaagac actgctggtt     840

cccctgcctc ttacaacctc tacgatgaca aaaaagccga tttcaaaaac gcttatggtt     900

ggagcaaggc actgcatgga ggcgagtatc ctccactcag cgaaccggat attggagttt     960

tacttgtcaa actctcagcg ggatccatgt tggcacctca tgtgaatcca atatcagatg    1020

agtataccat agtgctgagt ggttatggtg aactgcatat agggtatcca aacggaagca    1080

aagcaatgaa aactaaaatc aaacaagggg acgtgtttgt tgtgccaaga tacttcccct    1140

tctgtcaagt agcatcaagg gatggaccct tagagttctt tggcttctcc acttctgcaa    1200

ggaagaacaa gccacagttt ctggctggtg ctgcgtccct tctaaggacc ttgatggggc    1260

cggagctttc ggcggcgttc ggagtgagcg aggacacgtt gcggcgcgct gttgatgctc    1320

agcatgaggc tgtgatactg ccatcagcat gggctgcacc accggaaaat gcagggaagc    1380

tgaagatgga agaagagcca aatgctatta gaagctttgc caatgatgtg gttatggatg    1440

tttttaatt tgaacacttg atttggaata ggggttattt ggtagtgcta gtgcctagtg    1500

gaattctgtg ttgagttttt tgttctttat atttagttga gatgtgtgtt gtgttcttga    1560

gttgtgaata aaaatctact ttctttgtgc att                                1593


<210> SEQ ID NO 41
```

-continued

```
<211> LENGTH: 1431
<212> TYPE: DNA
<213> ORGANISM: Glycine max

<400> SEQUENCE: 41

tgggggttgc gattgcttcg cgtcttgttc aaccttcaca cacacagatt caaacacgca     60

tctcttgctc ttcacagaga cacgatcttc ttttcttttt cgcataggca aaatcttggt    120

tgggataatc gaataaatta aatcaaaata atatggatta catattttaa tgttaaagaa    180

tctgaccgtt tgacgtctct aatctgctat aattaacttt caaaaattaa ctctgcataa    240

tgtgtaaaag ccactcaaaa aactaaggta acaataaaat gcatatagga ctaatatact    300

aacattaatt gaaacaattg atagtgattt ttgtctttta aacaagtgtt tcagtttttc    360

aatcatgtct taggtatgaa gcagattata aatcatattg gataaaaaat attcaaattt    420

attaattcac gaaggagatt tagtcacagt tatatggaac tttgttaatt ttgctcataa    480

ttttaacatt aaacttcttt agagggaggg ggttaattaa atgcaagagt atcttttgtg    540

ttaattgatt ttactctcca gtatacttat actactatta tatacgatta tgcaatataa    600

ttaattttta attaacagat aaaaattcat ttaagaatta tcaaacatcg tgtaaatagt    660

ttttcttttt cgcaagtata ctttatagga agtaactcta tttttcttaa aataacataa    720

aaagaaaaga aactcatttt ataagataat aagatgctaa atgtgagtag ctttagacat    780

ccacgaaatt tgaaccttga ttctctattt cacagtaaat tagtctatta aattcaacac    840

tattaatatg tgagaggatt taaatctttc tctattttat tttcattttt taaatggaat    900

attattttgc atttaaaatg aaaaatatat atggtggatt tgagtgtgtg cacacatgta    960

tctttcttaa gttgacaggt agcatagttt taaataagtt tttgtctttt ataacaaata   1020

attttccgtc tacacaacta ttatattcaa caaaaaataa aattaacaca gttccacata   1080

taaacgttaa aaatttaact aaagaaagaa aatcataaac gttacgttac attcctattg   1140

gaattgatat gataagccta gcccaagaga aaagggaaaa tttccaaaat ttaaagggaa   1200

gaagataaga agacgctgat gttagagaat ttcaagcaga ctttgaatgt gtcactgtgt   1260

ttgtgtcttt gatccgaagt ttctcactga acctcaacat gtctacacat tacatcgcca   1320

gcaaacccct caagctctac atgcacgaca cgtgtctcta cattctcttc acactccctt   1380

cataaataaa ccaccctttc ttccatcctc atccctcaaa cacagtcatg g            1431


<210> SEQ ID NO 42
<211> LENGTH: 17
<212> TYPE: DNA
<213> ORGANISM: Glycine max

<400> SEQUENCE: 42

atccctcaaa cacagcc                                                     17
```